United States Patent
Tahara et al.

(10) Patent No.: US 11,311,568 B2
(45) Date of Patent: Apr. 26, 2022

(54) THERAPEUTIC PHARMACEUTICAL COMPOSITION FOR CANCER INCLUDING MIRNA

(71) Applicant: Purmx Therapeutics, Inc., Hiroshima (JP)

(72) Inventors: Hidetoshi Tahara, Hiroshima (JP); Masaki Kinehara, Hiroshima (JP); Yuki Yamamoto, Hiroshima (JP)

(73) Assignee: PURMX THERAPEUTICS, INC., Hiroshima (JP)

( * ) Notice: Subject to any disclaimer, the term of this patent is extended or adjusted under 35 U.S.C. 154(b) by 0 days.

(21) Appl. No.: 16/760,817

(22) PCT Filed: Nov. 6, 2018

(86) PCT No.: PCT/JP2018/041139
§ 371 (c)(1),
(2) Date: Apr. 30, 2020

(87) PCT Pub. No.: WO2019/093308
PCT Pub. Date: May 16, 2019

(65) Prior Publication Data
US 2020/0254001 A1 Aug. 13, 2020

(30) Foreign Application Priority Data

Nov. 9, 2017 (JP) .............................. JP2017-216336

(51) Int. Cl.
| C07H 21/02 | (2006.01) |
| C07H 21/04 | (2006.01) |
| A61K 31/713 | (2006.01) |
| A61P 35/00 | (2006.01) |
| A61K 47/42 | (2017.01) |
| C12N 15/113 | (2010.01) |
| A61K 45/06 | (2006.01) |

(52) U.S. Cl.
CPC ............ *A61K 31/713* (2013.01); *A61K 47/42* (2013.01); *A61P 35/00* (2018.01); *C12N 15/113* (2013.01); *A61K 45/06* (2013.01); *C12N 2310/141* (2013.01)

(58) Field of Classification Search
CPC ........................ C12N 15/113; C12N 2310/141
See application file for complete search history.

(56) References Cited

U.S. PATENT DOCUMENTS

| 2009/0202624 A1 | 8/2009 | Inazawa et al. |
| 2009/0246875 A1* | 10/2009 | Yamanaka ............ C12N 5/0696 435/455 |
| 2010/0227909 A1 | 9/2010 | Cleary et al. |
| 2011/0076768 A1 | 3/2011 | Inazawa et al. |
| 2012/0157334 A1 | 6/2012 | Beaudenon-Huibregtse et al. |
| 2012/0315640 A1 | 12/2012 | Tahara |
| 2014/0154303 A1 | 6/2014 | Tan et al. |
| 2015/0147384 A1* | 5/2015 | Koutsopoulos ........ A61K 38/08 424/450 |

FOREIGN PATENT DOCUMENTS

| CA | 2977624 A1 | 9/2016 | |
| WO | WO 2011/057003 A2 * | 5/2011 | ....... C12N 2310/141 |
| WO | 2012108843 A1 | 8/2012 | |
| WO | WO 2014/125277 A1 * | 8/2014 | ....... C12N 2310/141 |

OTHER PUBLICATIONS

Godbole et al. (Cancer Biology & Therapy, Sep. 2017, 8, 10, 801-805).*
Mohammed et al. (Nature, 2015, 523, 313-317).*
Zou et al. (The Journal of Biological Chemistry, 287, 6, 4148-4156, 2012).*
Stenvang et al. (Seminars in Cancer Biology, 18, 2, 2008, 89-102).*
International Preliminary Report on Patentability, PCTJP18041139, dated May 12, 2020, 5 pages.
International Search Report and Written Opinion corresponding to PCTJP18041139, dated Feb. 5, 2019, 7 pages.
He et al. "MiR-137 silencing of BRD4 suppresses oral squamous cell carcinoma cells proliferation, migration and invasion" Int. J. Clin. Exp. Pathol., 10(1):409-416 2017.
Kinehara et al. "Growth suppression of cancer cells by senescence-inducible miRNA" Tissue Culture Research Communication, 35(1):85 2016.
Tonouchi et al. "miR-3140 suppresses tumor cell growth by targeting BRD4 via its coding sequence and downregulates the BRD4-NUT fusion oncoprotein" Scientific Reports, 8:4482, 13 pages 2018.
Fu Dewang et al.: "MiR 631/ZAP70: A novel axis in the migration and invasion of prostate cancer cells" Biochemical and Biophysical Research Commuinications, 469(3):345-351 2016.
Lisheng Zhang et al.: "MicroRNA 657 promotes tumorigenesis in a hepatocellular carcinoma by targeting transducin-like enhancer protein 1 through nuclear factor kappa B pathways" Hepatology, 57(5):1919-1930 2013.
Xi Hao et al.: "hsa-miR-631 resensitizes bortezomib resistant multiple myeloma cell lines by inhibiting UbcH10" Oncology Reports, 37(2):961-968 2016.

* cited by examiner

Primary Examiner — Amy H Bowman
(74) Attorney, Agent, or Firm — Myers Bigel, P.A.

(57) ABSTRACT

The object of the present invention is to find a pharmaceutical having strong cancer therapeutic effect. The present invention provides a pharmaceutical composition for cancer therapy comprising a transcription or processing product of a gene encoding a miRNA, wherein said miRNA is one or more miRNAs selected from the group consisting of miR-3140, miR-137, miR-631, and miR-657, pharmaceutical composition.

11 Claims, 33 Drawing Sheets
Specification includes a Sequence Listing.

SEQUENCE LISTING

<160> NUMBER OF SEQ ID NOS: 32

<210> SEQ ID NO 1
<211> LENGTH: 21
<212> TYPE: RNA
<213> ORGANISM: Homo sapiens

<400> SEQUENCE: 1
accugaauua ccaaaagcuu u                                                  21

<210> SEQ ID NO 2
<211> LENGTH: 22
<212> TYPE: RNA
<213> ORGANISM: Homo sapiens

<400> SEQUENCE: 2
agcuuuuggg aauucaggua gu                                                 22

<210> SEQ ID NO 3
<211> LENGTH: 90
<212> TYPE: RNA
<213> ORGANISM: Homo sapiens

<400> SEQUENCE: 3
ccucuugagg uaccugaauu accaaaagcu uuauguauuc ugaaguuauu gaaaauaaga        60
gcuuuuggga auucagguag uucaggagug                                         90

<210> SEQ ID NO 4
<211> LENGTH: 123068
<212> TYPE: DNA
<213> ORGANISM: Homo sapiens

<400> SEQUENCE: 4
gtgagtggcc ccgggagagg gaattgaggg ggagaaagtg ggaggatgcc ggcgcttcct        60
cctggagttt tgctgatgtt ctccagtagt gttgggagtc tatcaatgag ggagtctagc       120
tttattcacg gaggggggaa ggtgttaggg aggcctgtat tttgtaactt tttagctctt       180
tgtacgagta atgcaagtat gcaggtttct gtcggaggag tcttttctcc aaagtgaata       240
ctcgcacctt tctggccagc agttggcaaa gggaaattga ggaagccaga gcatatgtgc       300
gcacagaggc catctgtatc tgtaaccttt tcctggtact gtgggtgtgt gcggtgtact       360
ttttgtttcg ggggtactct catataggtt cccgaatgag aactacttaa cctgtggacc       420
cctgaaagta aaattccttt tttaaaaaac aacaacaaac ctgttttgag agaggttcat       480
ttcagtacct attggtacag gagttaacct tctcagttac tgggtccaat ttcatgtgtg       540
tcaggaggac actgtaacag atgtcagtta ctcaggaact tgagttgtta ggaatcacaa       600
cttacttggg gaagagcatt tatcacatta atcattttat aaaagttgtg atttttttccc      660 tttcaccccc ccctttttt ttttagagta acaaattaca gcactttttt atttggtttg        720
aggctttgct tttttgaatt atctttattt ctgtatcaat ttaggataca tctttgatat       780
ttaagtcagg aatgatttttt tccttccatt atttttaaagc tgaagtttat aaaacctttg    840 acttgtatttt taggtatctt gtcagagtac caaattaaag gtttatgaaa gtaattaata     900
tttcatatac agaccttaag ggttaaacat agagcagaat tttatgtaag aagacataga      960
cagtagtata ctgagaattg tggtccgtct agacaactgt gggctcgttc tgtctgaagc     1020
cactgctgag agatactttg tgggaatgaa tgtaagcctg gggttatctc tcttttcgaa     1080
gttctccatt caggatcttg attagattaa tttaaaactt tctcaaactt aacaatgttt     1140

```
ggtccttttt tttaaagtaa tgagttctgc aagtttatta gcctgtgtat tatgtgacag    1200
ttcatttaca tattccatac ctgtgtccct aaactttcag gacacagtca gagtttgtgt    1260
ttcaagaatt atcaggacaa gcctcagttc atcttttctt aattttatgg actttcatta    1320
tttctaccat cagtttctcc aactgttgtc ttagaataat gtctttcatt tgaccacttt    1380
tccctcctct ggaacttctc ccactgaatt gttttctttt agttgccttg ttatgctttg    1440
gtaaggaact ttaaattctg tcctttaaat gtgtactgac atgaaaatac tgaatagtgg    1500
atgtaatgtt agaatcagag tcacgtattc tgttttcac taagatattg caaagagaaa     1560
tgtagtcatt ttctaaaata ctgtacccaa aatacagtag aagctgtatt tgggaagga    1620 ggggaggaca aactaagaaa caaactatag tttgaatgta ggttgcactc tgtcaaagtt    1680
gcttactaac tttaggacct acttttattg cttatggatt ggttaaaaat tacggtattt    1740
tttttttttt tgagacagag tcttgctctg tcacccaggc tggagtgcaa tggagcgatc    1800
ttggctcact gcaacctccg cctcccaggt tcaagcgatt ctcatgcctc agcctcccaa    1860
atagctggga ctacaggcat gtgctaccac gcctggctaa ttttttttgt attttagta    1920 gagatggggt ttcaccatgt gggtcaggct ggtctagaac tcctgacctc aaatgatctg    1980
cccacctcgg cctcccaaag tgctgggatt acaggcgttg agacaccgcg tcctgccaaa    2040
aaattatggt aatgttttat tgcacgtttg ggtagaaatg acaaagtttt tggggtccct    2100
gcctttgaga tgcttttact tgtaggtggt ggagacaatc aaacacaaat tgcacaaagc    2160
tataggagag gggggataga ccaatatttta tctaagaccg cactggatgt tagatattgt    2220
caacttatag atgtgaatat atttttacat ttttcactag ggaaatgttg cttttggacg    2280
tgtacatata gaactaattg aagtattgaa gccaaatctg ggaaggtttc ttttaggaag    2340
aaaagagcaa gtggagacac aatatttaag acttttggaa ttgaaaggca taagggacag    2400
ataaaattac gaagctggtt tgaagggaat acagatagag gttgttgagt agtgttaggg    2460
tcagttgtgt ttgtgtagac acatgattac agttcaaaga agcaactgag aagagtgttc    2520
ctgagagtaa tttcagatga ctggggagaa attacatttt aggtaaaagc tgtatgcctg    2580
gattaggatt ttgttttct agggaaccaa cattttatt atatcgtggc tatccagggc     2640
tatacagaag gaggagtgaa aaagaagatg cttagtgtgt tgaaagtggc ttcttacaaa    2700
aaagagttta gaaatgggac agtagacttt gctttgatg tgaaattta gggcaacaat      2760 tggatactgg tgcagtttca aaacagcaaa atagtttagc aggtaatata ctgaaaatgt    2820
aaagttggaa ttattttcaa agtatttagg tttcccagag tactgatgga aagtgaagag    2880
ctgaaaagtg ggtattttta gttaggggga aaatctgaat gaatgagaca ctacctaaaa    2940
tagatgtttt agaagtggat aagagttgaa gttaaaagg aatgagcagg ctttaaacat     3000
ggccaccagt ttagtcccag ggtatattat tctgtatttt tgaaacaagc taaaattttt    3060
tttttttttt aaatagggta tataggtccc ttgagattaa gttcagaaga gtatacttaa    3120
taataatttc attgttaagg aatttataaa tagaaggaca gatttgtttc ctcaaattca    3180
tgttttaaag ttcactgtgc attattatcc tacgttggt cttgatatga cgaagtgagg     3240
ccaaaaatag ctgacagaga aggctgcttc ccttgttcac agttggtgtg tgtctttgtg    3300
tcccatacaa tggaggggat atccctgtgt aggcacagta gtgctgaaca tgctttttt     3360 tttttttcc ttttaaactt tttattaaaa aaaagcaact tggcatttaa aaaaatgtag     3420
acatttttgc ggcttgcatt tagtattgac tttaacagga ttaaggattg tgaggaagga    3480
```

```
aatatatatt cacactttt  tgtgttcctt  agttggaatt  ctgcaccttc  ctagtagctt   3540
ctctgacttc  ttaacagtga  ttattcaaat  ggcagaaact  ctggggaaga  gatgtttcaa   3600
caaggagata  ggtctaaggt  gattctaggg  tgaaaatata  gggattggat  tatatgccat   3660
atggaggcct  tctcttgtca  tcctccactt  tccacaacat  tttttgtgca  gtcgaagcca   3720
tgttcagatg  aattttagaa  ggcagccact  tatagttaat  gttatttact  agtgaggaca   3780
gtgggaagag  tggtaacttc  atgtactttg  ccttggcaac  ttttggattg  atagggaatt   3840
agagagcctt  gagggtatat  gtttgtgtgt  gtgtgtgtgt  tttagcaccc  accagatgac   3900
cccaaaggcc  atgcataggc  tcatttcatt  gtactttgga  gatggttctt  ggagaagtct   3960
tctggtgctt  ctgacatctc  attgtgtaga  gaaagagttg  gcaaactatt  tttgtaaagg   4020
gccagttagt  aaatatttta  ggttttacag  gccacatgat  ctgtcacaac  tttcaattct   4080
gttcttatag  tgtgaaagca  gctgtagaca  acaaggaagt  gaatgaatgt  tgccgtgctc   4140
caattggccc  ataggccgaa  gttttttggac  tcctggtata  gacaactgcc  aaatccacca   4200
acaaacagta  tgagctttat  tacactacaa  agccaggact  ggctatttt   ggtggtcttt   4260
gttttctaga  tgagatgttt  ttctctgagt  tcatttaaaa  tgattctgca  taaagcacat   4320
actctactgt  acaaaatact  tttgccttca  tggtgatgaa  aactatggat  tgagggtcgg   4380
ggtgatacca  tctttaaagg  gatgcagcta  aaaagtaggg  actacctgca  tttcttatct   4440
aaagataacc  acagttggca  tttagtgata  tactggcttt  gtatcatggc  caaaagtatc   4500
tgtaaagaag  cttgtgggca  tacttttgaa  accttctgaa  ataaatgta   aagcatttac   4560
ttcgtgtgta  aaattagaag  tgtctatggt  tggtttgaat  aatatgagtc  aaattataag   4620
agcattaaag  tttgatactg  ctatctatta  aagtcttaat  ctcttgcagt  ggctaattca   4680
gtgtgtgaa   ttacacatcg  caattttgt   tttgttaatt  tcaagtacta  gtgtatatta   4740
acaaatcact  taaatcattt  aaatgtgtac  tttaaaaagc  tttgatgtat  atacatatat   4800
atacgtatat  atatatatgt  acacgtatat  atatacacgt  gtgtgtgtgt  gtgtgtgtgt   4860
gtgtgtgtgt  attttttttt  tttttgtgac  ggggtctcat  tctgtcaccc  aggctggagt   4920
gctgtggtgt  gatctcagct  cactgcaacc  tccacctcct  gggctcaagt  catcctccta   4980
cctcagcctc  tcgagtggct  gggatcacag  gcatgcgcca  ccatgcccga  ctaatttttt   5040
tgtattttg   atagagatgg  gtaacaactt  ttggattgat  agggaattag  agagcctcga   5100
gggtatatgt  gtgtgtgttt  tagcacccac  caggtaaccc  caaaggccat  gcatcatgtt   5160
gcccaggctg  gtctcttaac  tcctgagctc  aggtaatcca  tctacctcga  cctccctcag   5220
tgctgggatt  gcaggcgtga  gccaccacac  ctggccagca  ttgctatatt  tttaagagtg   5280
aatctttctc  acatgtgttg  ttcagaaagt  gtaattcact  ttgtgcaatt  ttacattaca   5340
gttaatatta  aaatatttgt  ttcatatgtc  agcagatacc  aacattggat  gatggtatat   5400
ttagtttcat  aaatcctatt  tattttagga  ttcccttgtt  tatggcaggg  gtggagatta   5460
ctcttgcaat  aatgatcact  ttttagttag  tttgaaacct  gcttttagtt  tatatgtagt   5520
atttctacat  attgttactt  aaattgaact  aacaatttac  ttttttaattt  ttcttcttcc   5580
ttttaaaaaa  agagtatata  atctgacaat  gttagtacat  cttttagaag  gtcactataa   5640
agttgctttc  cctatttatt  tggaaaggat  tatttcctta  ttattttaaa  aaatctttta   5700
atttttgtct  tttcaagtaa  ttttatcatt  gtcccaagcc  taaggatgag  tggcaattta   5760
aaagacacaa  ggtgtgcatc  ttctatctgc  aaatactcca  aacagaaatt  attccagttt   5820
gttgatactt  tgagtggacc  agggaaaaat  gtgtatgttt  ttagtgtaac  tgaattgtca   5880
```

-continued

```
ttacaaaaag atgagtaaag ttgctgttaa ataatgaatt cttgctgtta atttgtcctg    5940
ttcttagact ttcccccatt aagtataatg ggggaaaatg tacacacaca cacacacaca    6000
caaagtatgt atgtgtagat atacctagcg tattgtgcta gatgttcatt tctgcatgac    6060
tgctctggaa tttaggcaat attaaaagac cttacaaaat attttaata tcacttaata     6120 tcctgtttta tgtcttaatg tactttatg tttttgctgc tttctgatga tacctccttg     6180
gtacttcctc atgatacctt tcacagtatg tttaaatgga atgtattttc tcaaagtacg    6240
tgacattttc tgaacactat gggatatata tcttctagta attatatttt tacatgcaag    6300
tatctttaaa aatttcttcc tattacaact taagaattgt gaaacatttg agggagcatc    6360
tgcagtttga gcacttgatc tggatattgg aatgacaaac ttaacattta actaaatttt    6420
tctgaggtgt tcttttacaa tttttgagtt aacacttgat ttctgtaaag cagaaggctt    6480
ataagaagaa aatatgagag ccagtgttcg tcttgtatta tcctgccatg cacgtagttg    6540
aaaatcagaa acaaacagaa atgcacaaga gaccttattg cttgagtatc ttctgctctt    6600
cccccatcag acctaaggga cagctagtgg atcagtcaga tactgtgcag tttctgttgc    6660
tatgctgtgt caccttttgcc cttttctttct atctggaaga tagctactgg aaatctggct   6720
gtaagaaaga gatagcatgt ttttttcctc tctctctctg tgtgtttctg tctgtctgtg    6780
tacctgtacc tagtgtattg tgttagatgt tcatttctgc atgactgctc tggaatttag    6840
gaaatattaa aagactacaa aatatttta atattattta gccttttctc tgagaggatc     6900
acatcctctg gctttggcgt tttcatctca cagcatctta aacgaacccg tcaatgttta    6960
ttatcagttc caaatgtgaa gtctcaaggc aaattgttgg tttgttttg gaagaatgta     7020 tgtgtgtgtg tatatatatg tgtgtgtgtg tgtgtgtg tgtgtgtgtg tgtgtatata     7080 attttaaat ttttaacaaa aattcctgat ctagtcaatg cttatgagag tgtgtgtggt     7140
ttgtataaaa ttatttttt tagagacagg gttgcttgtt gtcaccaggc tggagggcag     7200
tggtgtgatc cttgctcact gcagccgtga cccctgggc tcaagtgatc ttcccacctt     7260
agcctcctga gtagctgagt agctgggact ataggtgtgt actgccacac cctgcaaatt    7320
taaaaaaaaa attctgtaaa gacagggtct cactatattg cccaggctgg ttctcaaact    7380
ccaggactca agcagtcctc ctgaaatggc ctcccaaagt gttgagatta caggctgggg    7440
ccacagtgcc cggtcagagt gtgtgtattt tttaacagcc ttttaggatt gcatgctttt    7500
taggggggtg aatgaggggt aatataccct tgcatgacat tctctaggtc tgagaaggag    7560
ttgcttcact aaaagtgtaa tttataatta ccaaatggtt gaaaacaggt ctacctggag    7620
tcagcaacag gcagctagtt tacttctcat ttacgtaata aaatacattc ataatatgca    7680
ttcagtaatt cataattcaa taatttcttg gcttcatggc cttggacaag ctatttatta    7740
tccttttaat tttggtggca tcacctgttg atggaggaaa acgtgtcctt tacatggtgg    7800
ttgttaggat taaatgagat aatataaagc atgcaaagct cttaatccag tgcctggcat    7860
atagcatttg acccatcagt gttaatttat taagttaaag ttgttttaaa gtgtgttgta    7920
gatagaagat ttaaatcagg ccttatatta agcccaacat ttaaattcaa cacttgagtt    7980
tgacaaataa tactgaagta attctgtgtt ttcagaaaca tctaaaactt cattaacatt    8040
ttattaaaaa ctgaagaaat gacagaactg ttgggctttt ttttaataga aagaaagac    8100 tgatttgaac ataactggaa tttgaattta gtttcaaaga tctcagtagt gcatggacca    8160 gaaagaatc cgttttttgaa tagttagtga ttatgatagt gactgtggtt taaattgccc    8220
```

```
atttagaaat agcaggatct aattcagtta tcagccttttt tagttgccca tctctttaac    8280
ccctggaaat aaaaagcttt aaaaaatcat taagaagttg aacggaaatt ttatctgtgt    8340
catttacatc tcaaattaag atcgaaataa ttttgtttac atgattctat tttaactact    8400
taattttagt ttttgttttt tcctgaaatt attagtatgt gggttttaaa aattccttttt   8460 tttgtgtgct taatatttgt taaatacaag attggttttc agaaatacct tttcttcgag    8520
tagggcataa tcagtgtttt attggccaat acaataaata aatgcttctt gattgttttt    8580
gtatttggaa agaaattcta tgttgagaac agttttggta tgctttcctt cattggctgt    8640
ttattgaata gaactgtata tttaaggtat atgaaaaaaa tctaagctag aaaaaaagac    8700
tgagatacat tcttggaaga aaatacttgc aaactatgca tctgacaaag gtctattgtc    8760
caacgtctat aagaacttaa atttacaaga gaaaaacgac cccattaaaa agtggacaaa    8820
ggacgtgaat agacacttct cagaagaaga cttacatgtg gccaacaagc aaagaaagct    8880
caatattact cattagagaa acgcaaatca aaaccacaat gagataccat ctcagactat    8940
tcagagtggc tactataaaa agtcaaaaaa taacagatgc tagtgaagtt gtggagaaaa    9000
gggaacactt atatactgtt ggtgggagtg taaattagtt caaccattgt ggaaatcagt    9060
atcgcgattc cttaaagagc taacagcaga actaccattc cacccagcaa tcccattact    9120
aatgggtata tacccagaag aatataattc attctaccat aaagacacat gcacacgcgt    9180
gttccttaca gcactaatca caatagcaaa gatgtggaat caatctaaat gcccatcagt    9240
gacagattgg ataaagaaaa tgtggtacat acacaccatg ggatactgtg cagccataaa    9300
aaagaaggag atcatgtctt ttgtgggagt atggatgaag ctggaggcta ttatccgtag    9360
cacactaatg caggaacaga aaaccaagta ccgcgtgttc tcacttataa gtgggagcta    9420
aatggtaaga acttatgaac aaaatgaata gacactgggg tctacttgag ggggagggtt    9480
ggaggaggga gaagagcaga aaagataact attgggtact gggtttaata cctggttgtt    9540
gaaataataa gtacagcaca ccctcgtgac atgtgtttac ctatgaaacc tttacatgta    9600
ccccgaaacc taaaataaaa gtttaaaaaa tatattcttt agcactgatt atcttgctag    9660
ctgtgacttc tccttttaag gaaagtttgc tttagatttt ggtgtaaatg tagaaattag    9720
atgggtttat ctgctagtgg ctctctagtt agatgattaa tgaatattct agtttaaaaa    9780
atttcagcat tttaaatact tttctttatt ggtaacgatt tggattatgc ttctagggat    9840
ctttacattt catagttttt caaaaaagac tttataatga gttcctggat gggaagaaga    9900
gcatgttctc tctagtttat ttgatttctt cctgattatt atgtatgtaa tactggaagg    9960
ttgtgtaaat aaatatttgg gttgtaagtt ttcttttgca tgattggtgg tctcttaatt   10020
gactgctgtg tgaatttgat agtataaact agaatgctta tacagtgagt ggggaagcct   10080
ttttctactg agtgttatgc aggtggattt ttccccctg cggataaata ctaaactttt   10140
atattaccag atttagacat ttagacagga aacaaaattt ccttttttttt aaaataaatg   10200 agcgggagaa gagagtgggg ttgtacagag gtggggagag aggcagtaaa ggagggagga   10260
aagaagaggc agatatcagg gagagtggct ccggaagttt tgagttcagt cttagtcaga   10320
ggtcacaccc tgttatttct ttgggttgtg gacatgaggt gttaccactt gttatctgtc   10380 acccttttgaa atgatgatta gattattggt ttttattcat agcttttcaa catttgggtt   10440
ctttaaacca ttgaaggttt agtttgtatg ggataatcag tgttatttta gggtgggaaa   10500
atttccacca tacctgctag gagaagggga tggccaaaga gttttttgact tacagaggag   10560 tttttttgtt ctgttgttttt ttcctcattg actctatttc gctagctttg tctgagaggg   10620
```

```
gtgcttataa ttctatatgt gacatagtag ctgagaggca agctttggag ttgatagacc    10680
caggttccag ctctgctgct ttgtgatttc aggcaagtta tttattccat gtgtgtttct    10740
tttaaaactg ggatgataat aatagtacct gtttccctta tagagtaatt aagaggattg    10800
agtgagataa tgcatgtaag cctttagcac agtgtctgcc taagttagca tccagtaaat    10860
gttagctgct gcaataataa gaaatattat agtattaagt tattgttatt tctgtgaggg    10920
tgctggtttt ctgaatgctg agacattggt gatctttgct cctgaacgtg ttactatttg    10980
gaatactgcc tttattcagc agcagattca gttcagattt actgaacacc tactatgcca    11040
ggaattgatc taaataagca aaacaaaaat cctgctctct tgaaacttac tttctggtta    11100
ggagagacaa aatacacaaa acaaaataga tgatgtgtca ctcaggaaat ttggttgttg    11160
gactttgtct aagctttcat taaccaaccc tagcagtctt aacctttaca tactttttga    11220
ttgttcctgt tgctgtgctt gagagtgttt ggaggtaggg gcaccctaaa agcgtatcat    11280
agactagctt tattgtctcc agcttcagct tgatcctaat tttaaggcag ccttaaatga    11340
tagttttcat catttccttg acttactact taaattggct atctcaaaac tttcagtccc    11400
caaaacttgt atttcacatc attcagagag atgttgctcc tccccagctg ctcctctttt    11460
gctcttctat gccattttct taagaggagg ggatactaga agcatctttt tagatttatt    11520
ttctgactag tctaactgta tacttttctt tctcatattt tgtgttttct acccttttatt    11580 tattgttaac tgatacattt aatttgctta ttttctttaa aatatgtgtt ttttttggtc    11640
tctccaatta aattgtgaaa gttttttaggt cagggaccac ttttctattt tgaccttgag    11700
cttactctct tgaaaaaaag ataataccac ccagggatgt tgtgagacct caaagagata    11760
atgtgtgaaa ggggtcctgg agccagatcc ttaataaatg ttagttttctt ctttgaacca    11820 ctctagttgc tgaaactgct gtgcatataa tcagtgctta aaaaatgctt gttaatttat    11880
cttgaattga gtttgtgaac tttcaattgt cacttggtgg tagttttagt ttttagtgct    11940
agataagatt caaaatacta cttttcaagt gtcagatgat aaatgctggg tcattagtgg    12000
tagagctcaa cagtgattag gagcaggaac ttgagccatc attgtttggg ttcaagtaca    12060
ggctaccaca cttactggtt gtatgacctt tggcaagttg tttaacctcc ctcggttttct    12120 ttatctgtaa ggaggggaaa atgatatcta cccacctcat ggttacttct ttgttagtat    12180
taaacgaagt aaatgagaag ctcgaaacag tgcttagtat ataacaatct ataacagggt    12240
ccccagggga catttggcac tatttggtga tgtttctgat ggtcatttgg gggagtgggg    12300
agagggaagg gtgctactgg tatctcgtgg gtagaggtta ggtataaaca aggtatagga    12360
cagcatccac aacaaaaaaa ttacctggtc cagaatgcca gccctgccaa gcaacattgg    12420
gaaacccagc ttagttcctt tgtataaggt actttgccag ttagattctg tatacatgct    12480
gattattgat aaagatgagt cacagacatg gataggcttc attaacatt cattttaaaa    12540 gacagacatg taagaaggtt agtaggtttc atttcttttt aaggttacag ggaaagtact    12600
ccaaaattaa tctaaaagtc cttacacttt tttcagaaac tgagaaaagg ttccagatga    12660 atttttactaa tttaattttt ttatgacgag ctattcatgt aaaagtgtat tatgaataga    12720
gggcttatga gatatgagtg ccgtagtgtg tattcataaa gtcaaacgta cacttaaaaa    12780
acaagtatca aggtaaatgg aatgatctat tgggggaaac cttggagctc tctctctttc    12840
catatgtttt attactcacc aagtcaaggg ctctttaact taggatcttg ttttttctgtg    12900 tacactttc ctgtttactg tttaaaattg gaccctttact aaaaatacag aaaattagct    12960
```

```
gggcatggtg gcgtgcacct gtaatttcag ctactgggga ggctgaggta gggagaatcg    13020
cttgaaccag ggagacggag gttgcagtga gctgagatcg cgccattgca ctccagcctg    13080
ggtgacaggg cgagactcag tctcaaaaaa aaaaaaaaaa aaaaaaaaaa attggaccct    13140
taccattcct tgtccatttc aggagcctct taattgcctt gcttctgttc tttctctgta    13200
ttcccacttg aattgactct tctttgctgg gatccctttg ggatcccttc tagtccagat    13260
ccaatctacc cttcagagct ccttccaccg tccccttatt tctgggagag aattcagcct    13320
taatacccta aggatggaat ttgaatgtac tgacttttct gctatttaca gggttgtgta    13380
ttatctttgg aagaattggg aagtcatatc atttttctgta tgttgtggtt caggtgactt    13440
gtttcacttg tatccaaaca ctggttgtgt gtccatgtat atacagcatg tatgtacttt    13500
aatgtctatt tgtatgtgtg tgtacatgta tattctttca tgtatatttg tctctacacc    13560
ttgctgtttc ctctgcttgg aatattcttt tcttttcatc tgggaaacat ttgtctcttc    13620
agaccctact taaatattga tctcctagga agtgtgtcct gattaatata actagaatta    13680 gttattttt tccactggtt acccacagta tctctgtggc ttttatagca cttaacatcc    13740
ttatttgtat ttttctttc tactgatctc tcagttcttt gagggcaaga gtcttgtctt    13800
agtcaacacc tgctccccca agtacctaac attcctgcca cattgtagac atatagtatg    13860
ttaacaaatg aatgggagag acaaaaaact ggaaagcttt taaataagtt ctatggggt    13920 tggcaggagg ggagaccaca cattatcttg tcacctttgt ttccaagtgc ttagtgttgt    13980
gcttgcccat aggtgttcag caaatatttg ttgaatgaat tagaagcaaa tcccaggagc    14040
tgataaaatt ttcatgtgaa cttttttctt ctgcatttct agaaagcata tcctagaagt    14100
aaagtagctt agatatttg gaacatctta ttcttaaagt cgaccttcct attttgact    14160 cagtagtgaa actttgatcc aatggatact tcctgaatag tgcttttggc tgattccttt    14220
ttcacaacat aggtccgttc tggtgttgag tttgttggaa agatgaatat gtagtatcat    14280
ttttacatca tggaggagcc atcattaagt aacagtgtta aataaggact ggtcccctttt    14340 gcacatttgg gcccaaatta agtgagtatg tactcttaag tatgggtaat gattgaggct    14400
attgaggtgt aggaaagaaa gaggacaact ggaggtgaag aagtgaccta ctagatctct    14460
tttgcttttg gtaatgattg atttttttt tttttttttt tgagacggag tctcgctctg    14520
tcgcccaggc cggactgcgg actgcagtgg cgcaatctcg gctcactgca agctccgctt    14580
cccgggttca cgccattctc ctgcctcagc ctccccagta gctgggacta caggcgcccg    14640
ccaccgcgcc cggctaattt tttgtatttt tagtagagac ggggtttcac cttgttagcc    14700
aggatggtct cgatctcctg acctcatgat ccacccgcct cggcctccca aagtgctggg    14760
attacaggcg tgagccaccg cgcccggccg gtaatgattg attttttacc cccagttatt    14820
tttaaagaat tggcaaggaa ggagaggggt atgaatctag aagataagaa tgtagatttt    14880
gtaattcatg atcattatta ttaccatgta ttgaatgttt actgtatgtc aggaactgtc    14940
ctaaggattt ttacaaccgt tatttaactt agtcctcaca gcagttcata tgaaatagct    15000
actgatgttt tatggcaaag gaaacaaatt cagagaaatt tccaagaaca catcggaatt    15060
ttgacttgca gaactgggat tcaaatctag atctgtcata ctccatggtc tatgcttta    15120 atcatgcatg ctgtctctta agttttatt gaaaatggaa agttgtactg acataggagg    15180
ggaaaatgat agaaaatcat cctattggaa ggcagattaa cagactcgtg aagaagcaat    15240
tcccagtttt atgtcattat acaaaataat tgtgaaattg aagtccgtca tttgaattga    15300
tttgcattaa ccctcatttt ttagtcttgc tcttggaatc atcatcagga caggtgtccc    15360
```

-continued

```
agatatgtta gcagtagaat aaatttatct aggcaaaatc tgtctaagat tatggagaaa    15420
actgatttta tatgtgaaat gtgttgttga gtgagagtta aatcttttga aggagattat    15480
ttcaggatga gcctcaaata cattatttag gatttgaaaa cctatggttt agcagaaaat    15540
ctgagaatca acatttgtta gtctcttggg tataaattgc ttaagtcagt gggtatctga    15600
ttattctttc tttctttctt tatttattta tttatttatt tttgagacag agtctcactc    15660
tgtagcccag gctggagtgc agtggtgtga tcttggctca ctgcaagctc tgcctcccgg    15720
attcacgcca ttctcctccc tcagcctcct gagtagctgg gactacaggc gcccaccgct    15780
acgccctgct aattttttgt attttttagta gagacgggt ttcaccgtgt tagccaggat    15840
ggtctcgatc tcctgacctc gtgatccacc caccttcacc tctcaaaatg ctgggattac    15900
aggcatgagc caccacgcct ggcttcccctt atgtaatttc ttaaactatt tttgtttgct    15960
gatttggtgt ttgtaattta aaaaaaattt attttttctt cttttacata ctttgtagaa    16020
ctattcccta cccagtgagt ttatttatag atatttcata tttaattaat actgtgagaa    16080
catagttttt atatctgtat ttttgttttt tcattaggat atttaaaata attttttgtaa   16140 ttctgttacc ttaaaaagag ctaaacttag atgttggcct ttaaaaatgt tttgtgaaag    16200
attttctctt ggttccattt aaaatactgt atttgtaact atagttaaat acatttgaac    16260
tttgcccttt tcagaaattt taattatatg cctttataaa attttatcaa aagttacatg    16320
caaatactaa gtatagagtg ctgaagctga gcgtgatggc ttatgcctat aatcccagtt    16380
actcgagagg ctgaggcaaa aggattgctt taggccggga gttggagacc agcctgggca    16440
tcatggcaaa accttgtctc tacaaaaata aaataaatta gctgggtgtg gtggtgtgca    16500
cctgtagtcc tagttacttg ggaggctgag gtgggaggat ggttttgagc gtagtagttc    16560
aagactgtag tgagccaaga tcctgccact atactttagc ctgggtgaga gagcaagacc    16620
ctgtttcaaa tatataaaata aataaaatag taggctgggt gcagtggctc atggctgtaa    16680
tcccagcaca ttgggagtcc aaggcgggtg gatcacttga ggccaggagt tccagaccag    16740
cctggctggc atggtgaaac cctgtctcta ctaaaaatag aaaaattagc tgggtgtggt    16800
ggtgcgtgcc tgtaatccca gctactctgg aggctgaggc aggagaattg cttgaacccg    16860
ggtggtggag gttgcattga gctgagattg caccattgca ctccagcctg ggcgacacag    16920
cgagactttg tcttgaagaa aaaagaaaa aataagtat tgagtgctga atgatgttct    16980
ataaaagatt aaaaatgcct aagtggaact aaattctggt aaatagaatt taggggttgg    17040
ggtagaaaga atcagataag tacttcaaga ttttcagact ttaagtctaa ggctcattag    17100
tatcctctga cataatctac tacaggtttc cttttcttaga agtgaatgtt aatatggcac    17160
cactatacaa ataatatcga tatcggtatt tgagtgttta ttatgtgaca ggcactgttc    17220
tgtgtccttc atgtgtatta cctcatccag tcctcacgat agctctatga ggtaagtgtt    17280
gttaatatcc ctattttata gctgaaaatt tggcatagag aagttaaaca tggtcaaggt    17340
cccaccttta gttaatagtg gagctgggat tgtttccagg cagtctggct ctagagcctg    17400
ggaccttaat cttttattcta tactgtctgt gtcatctgta aatttatttc ttatatatta    17460
tttatagaac agtgcctggc acacaataag agccatagaa gtactggcta ttttcattgg    17520
catttaatta tatatgaggt tggcagagca tgcattatta ttccatttgt ttatttatac    17580
tattaattag atagtagact ttattcagat ttctgtgttt cctttttta aatagtcgag    17640 tttaccgaag ttcttagaaa ctggatgatt gcctccaata atgtggccat gctagatctc    17700
```

```
aaaattaact ttttaaaaa aaccacccct ccaactttat ttacacttcc ttagaaatgg    17760
ataaagacca agattgggct tctgttttga tatgtcattg gtttagaaag gcagaaacag    17820
cctggcacgg tagctcatgc gtataatcct agcactttgg gaggctgagg cgagtggatc    17880
gcttgagctc aggagttcga gaccagctgg acaacatggc gaaaccatct ctactgaaca    17940
tacaaaaatt agctgggtgt agtggcactt gcctgtagtc ccagctactt gggaggctga    18000
ggcaggagga ttgcttgaac ccaggaggtc gaggctgcag tgagccaaga tggtgctact    18060
gcagtccagc ctgggtgaca aataagacc ctgtctcaaa aacaaacaaa aaagcggaa     18120 acaaccatac taagtttaca gtattgtttg tgtgcctact tggtggaaga ataaaattct    18180
tagaagttac actttcttta aaaaattaaa aattaaaaac tgtgcagtgt tgagattagt    18240
attaccgctt atcttgctga cttgtgaaat tgaattacat cacttataat aatgtgaagt    18300
tttagaaatt gttttgatga taaagagtag cagcctttaa gagaaataat ataaaccatg    18360
tttcctcaaa tctaaatggt catctgtatg gtattagttt tccatcgctc tacagaagca    18420
gtccccagcc ttttggcac caggaccat ttttgtggaa gacagtttt ccgtggatgc       18480 ggggaaggag aggcagtggg gaatggtttg ggatgaatca tcaggcatta ggttctctta    18540
aggagcacct aacctagatg ccttgcatgc acagttcaca atagtgtttg tgctcctatg    18600
agactctaat gccacagctg atctgacagg aggcggagct caggcgataa tactccacct    18660
gcagctcacc tcctgctgtg cggccgggtt tctaacaggc cacggaccag taccagttgt    18720 ggaccctgc tctacagcaa attaacacaa atttagcagc ttatcttaca gtttctattg      18780
gtcaggaatt tgggtatggt ttagctgggt ctttcctcag gttctcacta ggctgaaatt    18840
aaggaatcag ccggggctcc tatctcttct gaggctctgg gttctcctcc aggctcaccg    18900
gttgtgggaa gagttcaatt ccttgttctt gtagatctga tgtccctgtt tgcttgctgg    18960
ctgtcagcca gggaccactt tgagctcctt agaggcccac cccgccacc atgttcttgc     19020 catgtggcca agttattatg ttgtgtatga ctaaggaaga aaaatgctgg attaaaatat    19080
aagacaaatt cttactttat gtatgactaa ggaagaaaaa atgttgaatt aaaacatgat    19140
acaacacatt attgcttgga cagtgccttg caaaaaaaaa aaaaaagag agttgtggtt     19200 attcttccag ccacaatatc tgcttcagaa atgtcaaatt tattttctac tgttgtgttt    19260
gtgttctttt ttgtaaacaa cttttttgtt tcaatgctga atcatagtat tttacaggac    19320
atttaaaatt aagaagtaag cgtgacttct tattgtacta ctaaatgtac agaatttagt     19380
aataattatg gtgatataaa ctgccattac ccaatttgca agtgtacagg gaatgacagc    19440
tatgttgtga ctgccatggg caaatggtga tttgtaaagc attgttgctt ttttccccc     19500 atttttaagtt gatttttattg agatataatt tatatacagt aaactacaag acatttctgt   19560
caccctcaaa agattcctca tgccccttca cagttaaatc cttccctgca ccctcgcttc    19620
aggcaatcaa tgatctgctt ttttattact acaaattagt ttgcattttt tagtatttta     19680
aacagtgagg aaaaagagg agatggagac aggctatttt taattttat attttcttct     19740 ttgttcttag agaaatccta gtttcttat taggcattag gtttattcct tcagtgtggg     19800
ggtaaagtga ttcttcttga agcttctaa gtatgtttcc tagatgttct tgacctctgt      19860
tttgcctaag ataactttc tccagcatac ccagagttgg ctctcttaaa ccatacgtgc     19920
ttgtgtagct ccctcatcca tatttctact tattgtcttt tcaggaccgt aaacagaggt   19980
atttttgact tgacattctc agctcctaaa taatcttata gtgttactga ggcttttcac    20040
ctgtcacata cccccgtcct agtctctttt tgtgttgctg taaatacccg aggctgggta   20100
```

```
atttatgaag agaagaggtt tatttggttc atggttcctg caggttgtat aagaagcatg    20160
atgtcagaac atctgctttc tggtgagggc ttcaggaagc ttccactcat ggcagagagt    20220 gaagggagc aggtatcaca tggtgaggca ggaaaggaga gaaagaggag aggggtgcc     20280 aagctctttt tatcagttct catgagaact tacagagggg aaactcattc attaccttga    20340
ggatagcaca agctgtttat gtggaatctg ctcctatgac ccaggcacct cccactgtgc    20400
cccaccctca acattgggga tcagatttca acctgagatt tggaggtgtc aaatattcaa    20460
attatatcat cccctagaga acatacctcc ccacccctga gaatctcaga atttcttgtt    20520
gagaattcat attacagtat gagttgtagg aaacatgaag gaaagatttc ccttctagtc    20580
agttcttata tttatcactt gtttcatgct ccttggtgtg tatagtgttt tcaggtgcag    20640
gaaatgctct gggaagaatg ttgcttctta aacgtaaga gaaagggaac cccaagggaa    20700
gactcaaatg aagtccttaa aaagcccact tagcttcttc tgagacagca ttgtccaatg    20760
gaatgcaagc gagatagtta aatttaaatt ttctggtagc tatgttaata aagcaaaaaa    20820
agaaccagcc aacattaatt ttaataatat attttattta acacaatata tcccaaatgt    20880
tattttaaca tgtaatcaat atgaaaacca tgaagacttt gatatttaaa attcttattt    20940
taatactaaa tctttgaaat cagtgtatat tttatactta caagacatct gaatttggac    21000
ttagtcacat ttcaagtaag tgctcattag ttagtgacta ccttagtgga cagtgtagat    21060
gtagattatg aacttttttag gaaaagacaa tagcatgtgg actccacaag aaattgtctt    21120
taacaactgt ttgactctca taggttaggg ctttagtgtt tcagaatggt ttctatggtt    21180
gagatgtaaa gttttttatt tttataaagg taagtacatt tttatacatt ttcattatac    21240
aagtaatgtc attgttgaag agttggaaaa gtctgggtaa aagacaacaa attgtcctca    21300
cttcctcagt ccagagataa ccaatggtaa actttattga atttcctctt tgggaatgtt    21360 gcttttaaa atcaaagaga aaatagattt cttttttgtc ataattcctt cctgttcaca    21420
ttcagacata cattattatt gacaattctt ttacctctttt gtttaaattt atgtattctt    21480
tttctcgggc tgtatcctcc aatagggtct ctgtgagtgg agtactctgg agcacagtaa    21540
cctgaatggt gcttccctgg attagggtta acaatagaaa cttcaatggc ttttatgtac    21600
tcattgctaa accagtgtag ttgctttcta ttttaactat ctgcgatctc tttgcatatc    21660
ctgcagcttt tttagttatt gaggtataat ttgcatacca gaaaattcac tctattaaat    21720
actcaattca ggccggcata atttgcatac cagaaaattc acgctattaa atactcagtt    21780
caggccaggc gcaatggctc atgcctgtaa tcccagtttg ggaggctgag gtgagcggat    21840
cacctgaggt caagggttcg agaccagcct ggccaatatg gtgaaacccc gtctctacta    21900
aaaatacaaa aattagccga gcatggtggt gtgcgcctgt agtcccagct atttgggagg    21960
ccgaggcagg agaatcgctg gaacctggga ggtggaggtt gcggtgagcc gagatggtgc    22020
catttgcact ccagcctggg caacaggagc aaaactccgt ctcaaataaa taaataaata    22080
aatattcggt cgttttcatt gtattcacac agttgtgcag taattatcac tattaatcca    22140
gaacattttc attacctcaa aagaaccctg atgctcatta aggagtcact tcccatttcc    22200
tctttgcgca gtcctctggc aaccactaat ctacttccta tctctatgga tttgcctatt    22260
ttagacattt cttataaatg gagtcataca gtacatggcc ttttgtgttt ggcttctttc    22320
acgtaacacg atgttttcag tgttcttctg tgttgtagca tgcatgagaa cttcattctt    22380
tttaggactg aatagtattc agttgtatgg agggtaccac atttattca tcagttgatg     22440
```

```
gactttgggg ttgtttctgc tttttgagat cacattcatt cttcaagaac attaatttct    22500
taatatcgtc ctccattctt atcaaagctt tcagtggttt cctgttgtct ataaacataa    22560
tagaaaaata tttagtttgc attcagtctt acaaagtgta acttcaagtt actttctttt    22620
ccactcttat tttccatctt gttgttgttt actgtgtcta aaatatgtgc tatatatgaa    22680
ttataaaatt atgtagacaa tatagataac cttgtcatct gatctaattt ttaaaaagtg    22740
aatttgaata ctgccaaact aaggagtatg tgtagtatgg agaatttgag aaagacaagt    22800
atcagtaaag aagaaacagt atagtaaaac aaaattttt tctgccttgg tccattgaaa     22860
gaaatattta gtttcatata atgtgaacaa aaaccttaat tttgaatgaa catttgatac    22920
ataggaactc attcaaatca ttgattttct ggttaacttt gttagtagtt tgttttttc    22980 tgagtctttt gttttaatcc agatagtcag tcttttctc cttttacat gcttgaaatg      23040 gtaaaaatga atattttta cttattctta aaaatatttc cagaatgtct tacacacaca    23100
tacacttaga aacaaataca aatatatagt gatattctct cacattttac agagaaaagc    23160
gtagtataca tactttgttt tttaatttca cagtagatct tagaggtctt ttaatattag    23220
catactgaga actttctcat ttttttcata atagtattgt ttattccatt gtgatgaata    23280
tgctattgtt tttgaaacta gtcccatatt ggtggacatt taggttgttt ccaggtccac    23340
tattacagat aatactacag tgaataagtt tgtacatgta tcatttcata tgtatgccaa    23400
tatttctgca ggataatttc ccaaaagtga aattgctgaa tcaaaagata tatccacctg    23460
aaatttgatt acccatattt ttaagcataa aggaagagat aaagggaaat aaatagaaaa    23520
aaaagaaact atagattttc aaaaactttg tttatagatg aaaaaatgga ggattagaac    23580
ttttaagtaa ttgtccatgg tcatgcactc cacagaggac tgggcatggt gggattcggt    23640 gggggggcg ggggctgtg tcaggatgct aacccaggtg ttcctgattt taaataagct      23700
gctatccttc ctgttatatt catactgcat gttatgagca aaggggaga gaagtcgcca     23760 acttttgga gaaaagaat aaaatcccag actttatttt tgggatcatc tgaggtggga      23820
agatggcttg ggcccaggag tttgagacca gcctgggcaa catgaagaga cccctgtct     23880 ctacaaaaaa aaaaaaaaa aattaaccgt ggtgtttgag gcttcagtga gctgtgatca     23940
ctgcactcta gcctgggtga cagaatgaga tcctagtata tgtaggtatt taatgtatat    24000
cgaaggcagc atttcagatt ggtgggggag aagatggatt attggtaat ttatattgca     24060 gcaactttct attcatttgg ggaaaaagcc ctgtcccttg ctcttactct ttacataaaa    24120
aataatttaa aaatgaaagc aaaaggtaat atcgaaggat gtcgtgaggt tagccttatt    24180
caatagactg acctcagtga gtactgaact catgaaagtt tcattttttt cccagtcact    24240
gtcttttgca ttttccttaa ttgattttta acatcacctt ggattaatct catagctttc    24300
ccaatatgtt tttagttatg aaaagtctat ttctcctctt gccccgtatt aggcttgacc    24360
tgtggctgga gagatctgtg gtactgtttc atatgtaccg ccctcctctt tctctcctcc    24420
cttttttact tgttctgaaa acaatgagta aggttaaaaa attattttc acaaacatga     24480 aaaaggttga taatacgtaa gttttgaata tgggggaaag ttactctcat actgttgttg    24540
ggagtataca ttttttgtggc cttttggag agcagtttga cagtatttat caaaataaag    24600
tacacaggca tcttgaatca gcagttgttc ttccaaaatt tagtagtaca gatatactga    24660
cataacttta cttgaaagaa gaatcctttt tataacttag tgtttattga caagagaatt    24720
agcatttaga gtcatttatt attctaactc ttctaccaaa atggtgagat gtgttgtaat    24780
ttactggacg tttaggttgt tcccaatttt tttgtaagta tgaaaaatgc tgcagtgaac    24840
```

```
atctttgtct gtgtgctacc cagtcatcac tgttgagaat gtttcttaat ggctatattt    24900
aggtaagtgt tatttcccct tatttcccct cttatacttt aaggagcaca ggagatctca    24960
gttttaatcg cagctcaatt gcctaaatgg atgtgtgact taaaacaagc tctttaacct    25020
tactgagcag gaggttctgc agatatgggc ctctcagact attttatagc agtaataaat    25080
ggactaccta ttgtcacatt cttcatgatc ctgtagggag tatgtgtcag taggacaacc    25140
cattgagtga cagtcctaac tttcttggtt cctctccctc attgtgaggt cattgtttca    25200
caattgtata tacttactga ttcaaaaaac aactccaaca cttattgagg ggtagtactg    25260
ttcccagttg agaattactg ttgtaaaaat tttggcagga attatataag attattcatg    25320
attgttatcg acttatcttt attccttcat ttttttttaa agcaggaagc aataatagtt    25380
tacgttcgtt aacctcaata tctactctaa aacatgttgt ttttcttgtt attaccatga    25440
aagtctgggt taacaggaga cgagactagc ttcttcacag atacatacat taatttgaca    25500
ttatagaaaa atgagactgt atcctgactt gccagtttgg ttttgattgg tggtttcacc    25560 tttttttta gactcaggaa aacggtggca aaaatagtat aaagggtaaa ttctcatatg    25620
cccttcattc aagttcccaa aatttaacat cttatgcagt gacagaaaaa ttatcaaaat    25680
caggagatta acattcatgt aatactgata gtctacagac tttattcaga tttcacccat    25740
tttctcacca atggcctttc tctggtccag gatcacaata tgaaattatt cacgtgttgt    25800
attttagtta tcatgttttc ttagttttct ttaacctgaa acaattccag tctttctttg    25860
ccttttgtga ctgttatact ttggaagagt actggtcagt aattttgtgg aatattgcac    25920
aatttgtgtt tgtatgtttt cctatgattc aattaatttt aagcattttt gattaagaat    25980
actgcaaaaa tgattttatg aatcttattt agaggcacat gatgctgatt tgtccagtta    26040
tcagtgatac taattttcag ttcctttcgt taaggtggta tcaggtttgt ccactctagt    26100
tgcttttttt cctttgtgat tcataagtag tgttgattca gattctaggt taagaaaagg    26160
aaaaaaaaaa gtatcctatg ggaaggtact taaaaataag tactttggga ccaggtaatt    26220
aacatttctc accatactct accaattttt aacttcctttg ctgttttttt tttcttttt    26280 tttttgcag tggcacgatc atgagtcact gcaagcctca atctcctggg ctcaggtgat    26340
cctcctacct cagcctgtta agtagctggg actgcaggtg cacaccacca tgcctggcta    26400 attttttcata ttgtttgtag aggcgaggtt tcatcatgtt gtccaggcta gtctcgaact    26460
cctggactca agccatcctg tgttggcctc ccaaggtgtt gggattacaa gcgtgagcca    26520
ctgcctggcc ccagacttta actttttattg atgattttgt catggtgatt ttctgtttcc    26580
atcatttctt ctgtatttac attagtggtt tttggtaagg aagaactttc ccttgttatg    26640
tatttattta atgttttatg tatatcagaa tggactcgcg gattttttttt cccctcttat    26700 atcagatgga cttacagatt cttctatgga tttcatctat tatcatcatt atttattttg    26760
gtgctctaat tatcccaggt ttggccccat gaagcctctt caaggaggtt cctggtcctt    26820
ttgacatgtc tccatcattt tgtgagggct taactttttt tttttctttt tgagtcaggg    26880
tcctgctgtg tcactcaggc tggagtgcgc agtggtatga tcatagctca ctgcaacctg    26940
gatttcctgg gctcaagtga tcccctgcc ttagcctccg gagtagctag gactacaggc    27000
caggtatgtg ccaccacacc cagctagttt tcgccttttt tttttttctc caatagagac    27060
agagtcttgc tgtgttgccc aagctagtct taaactcctg gcctcaagca gtcctcccac    27120
cttggtctcc caaagtgctg ggattatagg catggaccac cacacctggt cagaaggctt    27180
```

```
aactttctag tagcgcaaaa tgttctagtc tcttcttgtg cttttctctg ccccagccat    27240
gaaatcagcc atttcaccaa ggaatattga ttccttttac tggaaatcgg aattcttcca    27300
ttcccctgc ccccagtact tgtatcttac catctttta aaagtctttg tgtcttagaa      27360
ccgtgttaga tgatctggac acattaccct gatgtacaga aattagttta tacacggtaa    27420
ttcttttgt agcagactgt ttaatttgta gcagattcat tttgcactga ttaatcctgg     27480
aggatttctt cacaagttac attgtgtcaa atatgttatt tcatgggaac acaattgaat    27540
tttttcctta attttgttcg gtatttgata ataacaattt aaaaaacttt tctaagagct    27600
tccttctaat attatatgat ataggaatgt ttacatttct catttattta tttggtgtag    27660
tgatctcaga agttttttta aagaaaaat cttgactttg tctcaggtac tctcagttca     27720
cttccatgtg ggagggtcat ttgccatcca tccagattac cttttgatt aggcttttca     27780
gtgtctataa atatttcggt cttttctgat catttaattt ctaatacatg catatgctcc    27840
tatgtataat aaatagacaa cttcaaattt gcagtttcta gatggttgga aaagggaaac    27900
attgtggtgt gtaatttatc agccatcaga tcctagatat ttgagatttt aactaagcaa    27960
ggtattagat agaccatgtt gttttggctt cacagaattc attcatattg tgcattacac    28020
aatcagtgtg catattgcac attgatttta tctgtaagtt gtctttatca gtggttctca    28080
aagtgtggtc ccctgctagt atagtatcag cctcacattg gaactggtta gaaatgcaga    28140
cttctcagga tccacctaat tgcagtagtt aattttaaca gcccttcgg tgatcctgaa     28200
acatgttaca gtttgagaaa cactgctata atacgtttca tttaaattgt ttcaggttgt    28260
gggggtaggg aataagacta ccaatttatt catcttctgt gcaatattac ctgtttacct    28320
aactcttaga gatattaaga tattttgaag aatgtgtccc atgagattat aatggaactg    28380
acaaattcct attgcttagt gatatcatag ctgtcatgaa gtcttagtgc tgtaccttac    28440
tcatgtgttt gtggtggtga tggtgtacac aaatcttctg cactgccagt cgtctgaaag    28500
tatagcacat ggccgggcgc ggtggctcac gcctataatc ccaacacttt gggaggctga    28560
ggcgggcaga tcacaaggtc aggagattga gaccatcctg gctaacacgg tgaaaccccg    28620
tctctactaa aaatacaaaa aattagctgg gtgtggtggc gggcacctgt agtcccagct    28680
actcaggagg ctgaggcagg agaatgacgg gaacctggga ggcagagctt gcagtgagct    28740
gagatcgtgc caccgcactc ccgcctgggt gacagagcaa gactccgtct caaaaaaaaa    28800
gtatagcaca tacaattatg tacagtacct aatacttgat aataaaggac tgtgttactg    28860
gttgatatat ttacaatact gcactttctg ttgttacttt agaatgcact gtttgaactt    28920
taaaaaaata aattcacttt gggaggccga ggcggacgaa ttgcttgagg ccaggaattc    28980
gagactagcc tggccaacat cgcaaaaccc tgtctctact aaaaatacaa aaattagctg    29040
ggtgtggtgg tgcacgtctg taatcctggc tacttggagg ctgaggcacg agaattgctt    29100
gaacctggga ggcagaggta gcagtgagcc agtatagcgc caccacactc cagtcttggt    29160
gacagagtga gactctacct caaaaaaaaa aaaaaattg caaacagcc tcaagaaggc      29220
ccttcaggag gtgttccaga aggcagcact gttgttgtag gagattacag ttccatgtgt    29280
gtgattgcct ctgaagacct tccagtggga cattatgtgg agatggaaga cagtgatatt    29340
gatgatccta atcctgtgta ggcttgggtt attgtgtata tttgtgtctt aaaacagttt    29400
tgaaagttaa aaaattttt tttaaaacag gaaaaaggct tataaaataa ggatataagg     29460
aaagaaaata ttttatata gctttactat gtgttttaag ctaagtgtta ttacaaaaca     29520
ggcaaaaaat taaaacgttc ataaagtaaa aacgttatag taagctgagg ttattacgga    29580
```

```
agaaagaaaa aatttttaaaa taaacttagt acagcctaag tgcacactgt ttataaagtg   29640
tatggtagta tacaataatg tcctaggcct tcatatgcat ccaccccaac tgactcatct   29700
agagcacctt ccagtcctgc tagcttaatt tatgatacag atgcaccgtt ttacatttta   29760
tataccttat ttttaatata cctttttatat atttagatgt gttaatatca ttgtgctaca   29820
gttgcataca gtattcagta cagtaacatg ctgtacaggt ttgtaacctg ggagcaatag   29880
tttataccat ggagatttgt gtaaaagcac tgtgtaatat tcacacaaag aagaaattgc   29940
ctgacacatt tctctgaatg tatctttgtc atgaggcgat gcgtgactgt ataatttgag   30000
ccacacatgt tattttaaaa attgcaatac ccttattaat gtaaaaagca gttgaattaa   30060
ttttaagata tttagcctga tggagccatg atattaccat ttcaacataa tttataaaaa   30120
aaattgttat tttagattct ctttgtacca agttttttgaa atctggtaga tattttatat   30180
ctcaatttca acactaactt tttaccggaa gtaattgatc ttcctttaga tttcataaag   30240
tttatggttg gaaaagtaga ttcacatatc taaatcgttt cagacacact taagtatttc   30300
gctacctgaa ttaagtacca aaaaataatt tttctgtaat atttgcatct aaattggtaa   30360
aactggttca tgtttttttag tagaatgtag tagactttga agcaaaactg tatccatttc   30420
aaaattgagc tactgaagtt aagcaaattc atgaactctt gtgtcaactc cgtattactg   30480
acattatatt caaaggaga ttggatgtta ggcaaatcta tattaaataa agtgttttc   30540 aatgattttt ttgtaatttt tgcagccact ttgcaaaaca ctgtcaatta aaatttatat   30600
atgttgattt atgttagaac aaagtgtaaa atcttttta ttggtttgtg ttatgaaaac   30660
tttaaatttc aatgtaaatt tataagaaag ttcttataaa atttctggca taccttcttc   30720
cagtttcttt ttattttact ttttcttgtg ttagcctggt cataaataaa ctctaccttt   30780
ctttggtgct tcaagttaag cttgttcata ggcattgaga tgtaagtgag gaaacaaaag   30840
aatactgcca tttttgtctt ttattactta atagtgaaaa gcatctcttt ctaaaatcag   30900
agttgacatt agagtagatc tttgtgaagt tattccacta tacccagtga gcaaagaaca   30960
cagatgtttt aaatgtattg tttttttattt ttttaacatt tccatgaact ggctaggatt   31020
catatttttg gcatgtacat actgaacaat tcaactcttt acatagggct tttcatagtc   31080
tgtttcagaa agctgaacac agatattttc aatgtgtatc atacagtgga ataaggaat   31140 aggagaaaca tcaattttg ctttaaaat tcctaacata gctggagctg tctgttgtga   31200
tagaaactaa ttgttaaata cctagctgaa attctttgac agaggtaaag gattaaaaaa   31260
tatctatgcc actcttgatt ttttttttttt ttttacagct acatagtgac aacttttct   31320 taagtttaga agttctttca aataaatttc acctaaaaga tttaattggg gccgggcacg   31380
gtggctcatg cctgtaattc cagcactttg ggaggccaag gcaagtggat ctcttgaggc   31440
caggagatcg agaccagcct ggccaacatg acaaaacccc atctctacta aaaatgcaa   31500 aaaattagcc gggcgtggtg gtgtgcatct gtaatgccag ctacttggag gctgaggcag   31560
gagaatcact tgaacctggg aggtggaggt tgcagtgagc cgagattgcg ccactgcact   31620
ccagccaggg caacagagcg agactgtctc aaaaaaaaaa atttaataag gtagtgtctc   31680
ttatatcaca tggctcatct aaagctaaag ggaaatagta attttcaca ttttgaatct   31740 gttgatttt cgtattatta gaaaggtctt ccatatgatg gatggtgtct taattgaata   31800
tcttccacgt gttgtaaagt atctattta gtattcctca taattttcta acaaaatttc   31860
tataattgaa ataatttctt taccatctct ttatgtaaat gtgattttct ttcttttggc   31920
```

```
gcaagaattt aagccagttt atagctgacc agagttacaa gcccagattt gttaaaaagc    31980
ttttaaacac gtttgttgta catttacttc tgacattgtt tggctaattt tgttgctttt    32040
cttctgattg tagagcagaa agttcttata aaattcactg tgtatttgtt gaaaatgtct    32100
cctaatattg tctactttac ttgtaaaact ttaaaaccca agaaatagct tttaattttg    32160
ctctgtcaca gctaattgta attgtcattc attagaaaat ttctagcata ccttcttcca    32220 gtttctttttt actttactgt tctggtggta gcattagctt ctgtatctct acttgattgt    32280
gtattgctgt aatgccttct ttttactttt aaaaatgtgt cctcctcttg tccattcatt    32340
tttaaagtaa gaaaattaat tatattcaaa atattaaaat taaaaaaaat aaaaagtatt    32400
gcgattgagt taccagttgt gatttacata ggcatcactg caacttgtgt tatttgtgaa    32460
aaacgtattt aagtaaacgc agtacggtgt tagattgatg agtagaaaaa tactcattct    32520
aactgtaaat tagttaattt ttactgacta gatcagtatt tttatgtgta atactagaaa    32580
tgactcactg tatcctgaga tgtggagtat aaatatgcagt acagtggtca cagtgaaatg    32640
tagtactgcc aaaagaataa aactttcttt agtagaagga cattttacac agcttcagct    32700
tttaaattta aattaagtac aactaaataa agctaaaaac tcaattccct ggtaacacta    32760
gccacatttc aagtgcttag tagtcacatg tggctaatag ctaatatatt agaaattaaa    32820 cctttttgaga gttggttatg tatgtgatta aagtattttg gttactttggg actagagatt    32880 acagtcattt ttgatcaggc tgatgtcata ggaacagtac caaggggact tctgaatcaa    32940
gcaccctaga aagagctact tagaactact tgcatttttct ttgtggcatc tcttataggc    33000
atgaaaaaat ttcaaacatt tttcatggat aaaaggattt aatcagaaaa gcatttggat    33060
atacatattt gaaatcatag cttgcctgta tgttactaga gtagttggag agtggaaaag    33120
tatctatatt ctaaagactg tttcatcatt tgggtgaaaa accaaaaaaaa gagagtaatt    33180 ttgtttaata gctcttttcac aaataaaaaa aagaatgttc atctgtagag acctatcgag    33240
atctcatcag gtttacaaca aactttagat tagcaagctc aatttcagtt gacatggatt    33300
gtggaaagat tttcagtgga gctcagatat ttaatatcct gaatttggat gaatatacaa    33360
tttctaaaat taagtacttc aactcctctg tggttttaaa accagtagtg gccatatctt    33420
gactagttat taaagcacca acctttttttt ctttattact ttgcttttat cctttgagca    33480
agttaggcaa taagttctcc atgttttttga tttctacaga agtaaatgaa tgttattgct    33540
gatgtttatt tcattctgtc ttgatctcat gatatgagaa tataaggaga tgtctgaaaa    33600
cttgttttaa aaatcctatg aagcataagt tcatgaataa agaaggaagt ggaacttgtc    33660
ttgagagaat ttgcctattt agatggtttc caaagtgcat tctgctagtc actagagatg    33720
gtccttgaaa gagttctgta attaagtttg aagaaacact gtgtaccata ataatggcct    33780
attgaatatt ttaccatgca cattaatata tcaaaggctt tgagatatct tacaagaaag    33840
aaacttgcta aagcttgtct tcctgcatgt cttaagcttc ttccacagtg actttaagtc    33900
ggacttgtct atcctgtgag aaatgctgcc ctctagaggc acaaattcaa ttgctcttaa    33960
atttgagtac cataatgctg cctgatctta gtgtgaagtt gtgataatta atattaatca    34020
aatgcatggt aacaaaacca aatagaagaa atcttatgtt gcttaatttt aagaaaatat    34080
gaggaaacag aattgcaatt tataaatacc cactttttaa attgtacatg tgatatttt    34140 ggctgctaat aatctttttga atacatttct gtatatgggg aattgcggac acatagtact    34200
tcaagtctcc aaactctgag tctctcctgc tagcagaagc catccttccc tgtgttaaca    34260
accttgctta agacagttac catccatggg gaagctagtt tcctcatacc ccttcccacg    34320
```

```
atactcatgt tccatacct gtaactggag tcagactata tcatgctgca cctttgcagt     34380
cacaatggga agaaaaggat tatatgtaat tttttaaag ttttttttt tttttttttt     34440 ttttgctgac aaagcagcaa aaccttcagg aatatgtaca gaaatgggtg atgatgatga     34500
tgtgagagag aagaaacat gcttttgcat ttggctgaat gtattggtat ggtgcagtta     34560
tcagagattc tgaattcatt gttctcgttc aagtagccag gagtggttct aattgtttgc     34620
tcctttggtc tcagcattga cttatactaa atgaagttga atgcctaaaa actcatagca     34680
taatatagag gaagaagtca aaagattaaa ggaaatagaa ctgatggagt ggatttatca     34740
ctgtgaccat tcacttacct cccctattcc ctctccagta ttctctacta agaggtctgg     34800
aagacacttc attcaccaac ctaatgagaa atactttgag ggcagtgcca gcatatatga     34860
aaagtaattc aattgctttt gtctgtaggc tggaggagat actttcattg aaattgtctt     34920
ttttacttca gggggtgtgg ccagattcta ggtaaggtcc aggcatcatt ttcataaggt     34980
agcttgacag gcatgatgat cagagatgca ctgacttgaa ttcttttttgg ctgtgactaa     35040 atgatcatgg atccctacgt ctaaaataga gaggaagcct attaagatcc tactttatct     35100
gtatgagcaa aaaattttag gtctcatagg agaaggcctt acttgaacta ccataagagt     35160
gagttggcca gcctgggcaa catggtgaaa ccctgtctct acaaaaaaca caaaagttaa     35220 ctttgtgtt ttgggcatgg ctgcgtgagc ctgtggtcct ggctgctcag gaggctgccc     35280
cctttttgca gtttacttca tgggttatat gagaaaacag gaaggagggg gatatcaccg     35340
agagattctg atattggagc tgtgtgcaat aactgataag tctctggttc ttacctccat     35400
atgaggaaca gagagagtct tgtttgtaca aggcttagtt ataatctgtc aggtttgagg     35460
atcttgattg gaagcataga cttgatctgt atttgtggtt tctcatttca aatagcctct     35520
caatgttgga taaatttgca tgttcatgtt ttatagagtc agaactcaat ttcctagtat     35580
tccttgcagc tagggcacaa gcatatgacc taggcttttat tgatcagatg catctgtgta     35640
agacatgaat tcagggtcag agaaatgcag ggtaacagct cttgcctgga attgctttct     35700
aatgtgcatg ttgagtgaca agatattgag ctgtttagag gtagcagtga cagagatact     35760
agtgagcctt gttgtcctag gctcagcttt catggtacta gggctgaagg atgggaacaa     35820
tttggtgggg agacttaggt attttttcctg gcatcatatc tccaagtgga ttcttcagtt     35880
ctctgataat tcttggaatc ccctaatata ttaataaatt tattttctct tgaaaccacc     35940
tcaaatagat tctgtttata gcttagagcc ctgattgatc gtctaacttt aaagatttta     36000
tttatcgtca aaatattta ttttttctaat tgagatctaa aaattgtcaa gcacttatac     36060 tctattttt cccttcctag agctctgcaa tcctttgctg tcattttttc ttaccaggaa     36120
tgccaatttt tgtacctttt gaattgcttt ttcttctttg ctacttggct tgagctccac     36180
tattgttatg aaacctttct tataccatcc cagcagcctg atggattttt ttcttcctct     36240
gaattccagt agcacttgtt tagacattaa gtgcaaggtg ttttttttgtt ttgttttgtt     36300 tttctgtatg catcttagct tccgcactaa atgataagct ccctgaaaac tagtactatg     36360
cctctttata tcgcttgcat tgtccaacag aatgtcttgc acctattaga ttcaaggttc     36420
agcacagtca ccctcataat atatagtgat gagagttgct gagaatcaca gtgatgccag     36480
gctgaatgag ctgagataat aaactagtta gatgcatagt ctggccatga ggcccaatttt     36540 ccatcttcct caaggagtct gagacttgcc tctcagtagt tttcgttagt aggtgatcat     36600
atcttctgaa ttactgtctt cttaatgttt tatgagtttt ttttttgcctt gacaaaagcc     36660
```

```
ttctatttct ctcatgcttc ctagttcctt ccattgtgcc ctctgcaatt tcttttcact      36720
aagcttacta tttgcagtct cttaaaattt gtgtaaatta tgaaatcaaa gatacaaaga      36780
aaggacagaa agtagtataa caaacacctg tgtatctaac ctcagggtca agcagatatt      36840
aaccttttgc ctcgtttgat ttccttttaa agttcttccc tccccatact tttctccctt      36900
ctttggaggt actcattatc ctaaagtcct tacgattatt tccctgctgt ttttgtacac      36960
ataaaacatt tacacaaaag atgacctgtg ttttttcta gatgtgttca tattgacatg       37020
tgtagattta gttcattcat tgtaactact gtttagtttt ccaggttgaa taatgctaag      37080
ttttatagag ataatgcagt tctacctttt ggcaaataat attgtaatgc tcgtacatag     37140
gtacttactg taatttatc taggatagat acctgaaagt agaattgctg aatcacaggg       37200
ttcaggtgcc actttatcaa gtattgccga gtccagtcca aagtggagct accattttat      37260
acccattaac atgtttccac acttttttt atcaacattt aattttatct agctatgatt       37320
tttttgccta tttgaaagat gagaaatgga gtttgatgat tttcattttc attactttga      37380
tttatagtaa agttgaatgt ctttgcatag ttttgatca ttctagtttc ctattctgtg       37440
aatcttttat gttcttgct gatttttttc ctattgggta ttgaacctta aattgatttg       37500
tggtgattct ttttataatc tggatattaa tggttttggt aatatgcatt gcaagtatct      37560
catagtgtgt gtgtgtgtgt gtgtgtgtgt gtgtgtggtt tttttttttt tttttttttg      37620
agatggagtc tcactctgtc tcccaggctg gagtgcagtg gtgcgatctt ggctcacaca      37680
aattctgcct cccgggttca agtgattctc ctgtctcagc ctcctgagta gctgggatta      37740
taggtgcccg ccaccacacc tggctaattt ttgtatttt agtagagatg ggatttcact       37800
gtgttgtcca ggctggtctc caactcctga cctcgggtga tctgcccgcc ttggcctccc      37860
agagtgttgg gatgacaggc gtgagccatt gtgcccggcc ttcgtgtcgg tttttaacat     37920
tgtttaaaag tttcagattt actacatgag ttcatttgta gaatctctct tctgtatcat      37980
agcttctttg gtctgctttc atgtctttac aatattgtgt taattttaat agttttgata     38040
taaatcttgt tatctgataa ggtgaatctt ctctcaatga aaattttggg tcagctaatc      38100
atatttcacc ctgaccctaa tgaaaattta acagaaaaca aaccctgttg gaaatgtgat     38160
tggaatctca ttgaatttac aggttacagt ggggatagtt gtcaccttta cattggttga     38220
ctgtcattga tatttctgtt caatacagtt ctattttttt cttttttctt tttctttttt    38280
ttttgagatg gagtcttgct tttgttgtga tctcggctca ctgcaacctc cgcctccctg     38340
tttcgagtga ttttgctgcg tcagcctccc cagtagctgg gattacaggc gcctgccacc     38400
atgcctggct gattttgta ttttagtag agacagggt tcgccatgtt ggccatcctg        38460
accttaggtg atctacccac ctcagcttct cgaagtgctg ggattatagg cgtgagccac      38520
tgcgcctggc ccagttccat ttttttcttg atagaagtct tcattagatt tttttttttt    38580 aggttttat gattttgtt accatcgtga atggcaaatt tttataaaaa tacttttgt        38640 tactggtagc tacaaaccaa ttagtataag agacaaattg ctaagaagca agttgctgtt     38700
tgtatcttga ttttgtatct ctcaatcttg ctgaattctt agttgttttt gtttgtttgt     38760
ttgaggtggt gtgtcttact ctgacaccta ggctggagtg cagtggtgtg gtcactgctc     38820
accacagcct tgactgcctg ggttcaagca attctcccac ctcagcttcc caagtagctg     38880
ggaccacagg tgcatgtcac cacacccaac caatttttaaa attatttgta gagatgaggt    38940
cttgctatgt tgcccaggct gctctcgaac tcctgggatt aagcgatcct cttgccttgg     39000
cttcccagag tgctgagatt acaggcatga gccattgcac ctggcctaaa ctcttacttc    39060
```

```
taatgataga ttctcttgga tacctcatgc agataatcat ataagtagtg aataaagatg    39120 gttttgttg ctttctaagc ctatgtcttt atattttct tctgttattg acctatgtag      39180
gaccacttta ctaaaattgc agcttttcct gggccttggc tttatgtgtg tgttaatgta    39240
tggagtagaa aggggtatct cagaactgaa gtctcccact aagggccaaa agtctcattt    39300
ctagtcccta catatgagtc aaaggataaa tataggttaa gactagcaac ccattgtagg    39360
gaagaaacat tgccaacttg tagcctaata tatatatttt taatatgtta ctgttttttc    39420
catgttactg gcacacactt aaagatttct gtttcatggt ggctaaagga ttaatttaaa    39480 ataattttt ttttccttt tgagttgagt ttcactctgt tgcccaggct gaagtggagt      39540
ggggtgatct cagctcactg caacctctgt ctcccggttt caagcgattc ttctgcctca    39600
gcctcctgag tagttgggac tacaggtgtg tgccaccata cccagctaat tgttttttt    39660 ttaaattttt agtagagacg gggtttcacc atgtaggaca gggtgatctc gaactcctga    39720
cctcaggtga tctgcctgtc ttggcctccc aaagtgctag gattacagac gtgagtcacc    39780
acacccagcc taaaagaatt attttgatat atcctttctg catgaaattt ctgtgggaag    39840
gcttttcagg tgatctgatc tgatacagtg ttaggactgg aagtatagct tatactatat    39900
aaatttcctt aattgaaatt tcacattatt taggaactct gtaccctgaa gctgtctcac    39960
tctggtattt aatgtcctac aattagttta agagagcaag cttgggtaag tttcttaaaa    40020
cttccttata tttgtttctt catcaatatt agtagtatag tatcatctcc tatcttatag    40080
attattataa gaaataagtt aataatgtaa agcatttaga acagtattag ttattggtct    40140
caacctcctt ttagctgtta tctacagcct ttctggtaga ttttacttat tctgggaaga    40200
tagtggtgta ttcctcataa tctccttgta cattccaggt cctacaataa ttctcaaaca    40260
ttttagcatc cttacataga ctctccaata tcctggtctt atttccctga tctcctcaaa    40320
tctactgatt tttctcttcc tcagacaagt gattttcac ttatttggta aaatcctaat     40380
tctggattaa ctcggttatc agattctttc attcctatac cacctgaatg ctgcagtaaa    40440
aagttacctc aaaggacatt taaaaaaat tataaattca tgattgttga tcacagaccc     40500
taatactgca tgggaatcca ctgcattatc cttgtcagct agtttcctca tctttaccat    40560
gactgtttca atcatctgtt ctcctcagac ctccaacatg cccttctct ttctacagaa     40620 aacttttcct gttactttcc agtgaaaacc ggagtacttg gtgcaaccct tagttgccca    40680
ctatcttttc tatattttct ttcttcttaa tgttaaaata gaggtagtct tgctttctat    40740
ctaaggcttt ctcccttttct ctgcagtacc ttatgctgtt gatgatttcc ctttttttg    40800 tatgtttaac ttttctttac acttgattct tctcgtcagt atttaaacac gcttaattcc    40860
tgctattaaa aaaataaaaa caataagcat taatgggtac cacattactg accttctctgt   40920 tctctttcct agccaaatgc tagaaattat tgtttccatt tctcacccttt gactcacctg    40980 tttagtttat tcattccact gtaatagtat ttgcttatga taccaacaac ctctctgtta    41040
gtaaattaag tgaatatttt taaacttggt cttatttgat ctctcacttg gtgtgctagg    41100
gcttctataa aataccacag actgggtggc ttaaacaaca gaaattaatt ttctcactat    41160
gtggaggctg gatgtcaaag atcaaggtgt tggcaggttt gttttcttct gaggcctctc    41220
tccttggctt gcagagggtg ccttcttgct gtgtcctcac ttggtttttc ctctgtttgc    41280
atgcatttct ggtgtctgtg tccagattgg attagggcct ggaagatgaa tttactcacc    41340
tctctaaagg ccctatatcc aaatacagtc gtgttctgac gtactggggg ttagggcttc    41400
```

```
aacacgtgaa ttttggggga gacagtttgg cacataatct cctagcaggt ttaaacagtt    41460
ttgaaaaact atccttggct ggacgcattg gcttacacct gtaatcccaa cactttggga    41520
ggccgaggcg ggtggatcac ctgaggtcag gagttcgaga ccagcctgac caacatggtg    41580
aaaccctgtc tctgctaaag atacaaaaat aagccaggtt tggtggcaca tgtctgtaat    41640
cgcagctact cgggaggctg aggcacgaga atcgcttgaa cctgggaggc agagtttgca    41700
gtgagccaag attgcgccac tgcactccag cctgggcaac aaagcgagag tctgtctctg    41760
gaaaaaaaaa caaaaaacaa aaaactatc ctttaaactc tttggttttc attttgcctc    41820
tctgatctat tgctcttcag ccttttttta acaggcttct cttctgcttg gttattaaaa    41880
gtagaaattt cttgagtctt ggtcctttgg tattttctgc ttctcttact tctgttattt    41940
ctccccaggc agtcttacca ctttgatttc catttatgaa ggaactgcat acctgttgtt    42000
ccagcactta atttgcctga gtttcagacc tatttaataa tgccatttag cttatcctag    42060
aggtacctta aaaaaacgag ttcaaatctg aactcataat aatccccatc catgtgattt    42120
gaccctaatc tacctcctta gccttactat tctttgttac tctttgccat agctgcacta    42180
tagcaaagca cggcctcttg gtccaggcgt aatatacctt ttcctccaga gtctttgctc    42240
ttatttccta tgttaatatg ctcctcattt ttcatttaca acattaccca gttttcaata    42300
catacaaaag ataaaaacat tagttattag ggaaatgcag acttaaacca taaaataatc    42360
actaaaacca actagaaggg gtaaaattaa aaagactgtc aactcaaat attctaggaa     42420 gccatccaga acactcgtaa attgctggtg tgagtataaa atgggagagc cactttggaa    42480
taccactggc aatttcttat aaatttaagc atacaccttt ggatccagca attctacttc    42540
taggtgtttt cggaaaagga atgaaaacat gtccacaaaa aacttttaaa aattatattt    42600
acagtcgatt tactccttac agctgacaac tagaagcagc ccaaatgtca ataggattaa    42660
tgactaaaaa ttttttggta tattcataca atggaatgcc actcagtaat aaaagaacta    42720
cagaatggca aatgtacaca acatgacatg gatgaatctg acatacttgg caaggaagc     42780 tggacatgat actgtattat tccatttata ttaagttcta gaagaggcaa agctactctg    42840
gagtgaaaaa ataaaaacag aacaaaggtt gccttttgct tctggaaaat ggtgatattc    42900
aactgggagg gtgcataagg ggccttcttg aagtgatgaa aatgttccat atctcataga    42960
ggtgtgtgtt acatgggctt atctattaaa gttgtacagc taagaagtat gtatttcaat    43020
ggcatacatg tatcttagat aaaataaaca agttttatct aaaaattata gaaataattg    43080
agttaggtga cagggagtgg gaggtgtaga tgaaagaaga attgcagaac gttggtggtt    43140
gctgaagttg agtaatggat gtggggaagt ttagtatact attttgtttg ttttttgtgt    43200
gttcaaagtt ttccatataa agatctttt aaatcaaagt tacgaagaca cttaaacagc     43260
acctgtggtc tgactgccag cttaataaag aatgcttact aatgtaattt tcttctctgt    43320
gaatcgtacc ctgattcagc actcctttct ccccaccagc cactatcctg aattcctctt    43380
gactttttaa gacatcttcc aaatatcatt ctaaacgtca cgtccatggg ggaaagcctt    43440
ttctgattca gaacactcac tagttttaag tgccctgtt aagtccttc atagctttta      43500 tcttaattat gatttatttg cttaactatt atcaacctct acactagact aagcctaagt    43560
ttttggaggg aaagatatat ctattcttgc tgttttaatg tctagaataa taatacattt    43620
attgaatgat tatgttggtg tagtttttta aaaaaattga aggatacccca aattgaagag   43680 ctattctatt actgcttatg ttgtaaggtc agtatgttat aaaatgtatg aatgtgagag    43740
aatgactgag aaatgataat ggtttctttc tgattttatt ggcatctgat aaaaacaagg    43800
```

```
ggcaataaaa ctgtgttatt agatctggaa ctatatccgg aaagtcctgt cagttggttc   43860
tcaaatgccc ttgagctttta ttatgcttct tccttattaa tgtattaagc cgtgtgagtg   43920
aaagacccct ttcctctttta caaagaatat tctaaatcac ctcttttttc tctcttctct   43980
aatgtgcttc ttcctttgac tattagtttt ggtatttatc agggacagcg atctttaaga   44040
gcttgttgtt ttgttatttt ttgtactgct tgctgtatgt tttaaatttt gatatatctt   44100
actgccaaat gaaggtgtga gctcataagt aataaagata gaaaaatct gctttgctta    44160 taattatacc attaaacatg ttgtccttaa tgcagataca cactattggt attgtaggtg   44220
caggattatg ttttgatttt tgccagttca tatttccatg gagtatttag gcaattttaa   44280
caacatagat ttctgtaatg aatgtttttt taacttatgc tgctgcttga gagacagagt   44340
cagactgcca gggtttgagt cctatgccca atatttccta gctctgtgac ttttgagtta   44400
tctgcttttt gcctgtttct tcctcattaa aacagagata ctaagtgtac cttatagtgt   44460
tgttgggagg gctatttgag gtagtatatg taatgcctgg tacttattaa atgttagatc   44520
ttttttactt tcttgggttc tagggagtcc aataagtaac aaattttttcc tctaaggttt   44580 ttttctttat tggtggcaaa atatacatag tataaaattt acatttcaac catttttaaa   44640
tatacaattc agtggcatca agtacattca caatattttg caaccatcca tctctgtcca   44700
tttccagaag tttttcatca tcgcaaataa aaacttgata cccattaaac aataactccc   44760
atctttcctc ccctgatttc ctggtaacgt atgttatact ctgtctttat gattatgact   44820
attctaggta cctcataaat agaatcatac agtgtttgtc ttattgtcct ctcatttcat   44880
ttggcataat attttcaaag ttaattcatg ttgtagcgac ttctagttcc atttttttgtg  44940 gttgaagaaa gtacttccct aatagaaatg aaaacatgtt tgcaaggctt tttttaaaga   45000
atgcttatgg atttagtcat aataggtaac aactgaaaac attggtatgg ctgggtcaag   45060
ttggactaat tcactgtagc ccagggtcat gtaagaacat ggagttttca aggtaggcat   45120
gggggtggta ttgaggggag ggtagtaagc ataaaagaca gtgctcagaa gaagataagg   45180
gtgccaggtt tcagttccag ggatgttcac agtaaggatt acagtgggct aaattttaag   45240 attaattttta taaattctaa acacatcctg ttgactttaa ctgcaactct taaaatgtat   45300
caataacatg actttataat tcctggaaac tgatattttc ccaatacttt gaagaggttt   45360
aaaaatagtt gactaatatt agaaccaata tttcatgtat tgattttct ctttaagtga    45420 cagttagttt agaaaatgct aaacttaagt tagcagtata gagtaggtat atagttatac   45480
tgagtatgaa tgtcttggta ggcttggaag cctaccattt atgtcctctt gaggtacctg   45540
aattaccaaa agctttatgt attctgaagt tattgaaaat aagagctttt gggaattcag   45600
gtagttcagg agtgactttt ctaaaaaaca gaactgagca ccatacacta cttcttatag   45660
ccttttaatt actgccaatt gcctagaata aagttcaaat tcgagggcaa cacaaacatg   45720 gcccttttgtg aactgacaga catttcctaa taattcctta catacatgat acccttgagc   45780
cttacagaat taagaatttc tgaatttacc ttggtgtttg atgcatctgt gtttctatac   45840
gtgctgttta tttacctaaa atagactatt ctctatttag cctcaaaagt ctcatggaag   45900
gttttaaaaa atcctgtcta agctctgtta attatattct ttatactatt atatttagta   45960
gttaatatta taaactacct tacagtaatt tttacagata cctggcttac tccctaaatt   46020
gagttgcttg agggcaggaa ttgtgtatta atctttgctg tattttctttt gccttgctta   46080 ctgtagttga ttggtgctaa ttgaataaat gaacatttat gcttttctttt ttgagaatat  46140
```

```
tatatgggta gttcctttag ttgtttaata gaagatagca cagacttcta tacagattgg    46200
tttttatggg aaaacacaag agaataatta attaaaacat aatttcatct agaaatttct    46260
gcagttggag cgaatatttt ttaagttatt aacttaccta gagtggaaga ttgaatttt     46320 gaatgatagt gttttagtta ttaaagtaaa tggcatgtaa gagaacttt aagttcatgt    46380 ggcaaaacag ggaaaaattg caaagttaga gtctgtaagg tttctgatgt tcatagact     46440 aacaaaaggt tgctttatta gcagcattaa tgaacgaatc gctttattgg cctaggcata    46500
ctggtagcat tgtcgttcca aagagctgag agttcttatt tcaattcatg attatgttag    46560
acaagtgaag tgaaagccgt tgaccttctc ttaaggagaa aatagaaagt ttttacaaat    46620
agattataga ttaaagcctt ttaaggaaca tgatgaagaa ctaaattact gctaaatcac    46680
ttgaaaaatt tatattttt tatgcaccag tcttataaca gtaggttttt tatagaccta    46740
ttaattgata tttaaaataa taactttaat aggatgattt tgtagagtta gtcaaagtga    46800
ttgacaaaag caaattatta aaatagtcaa actttcaatt ctccaaagaa tgttcagttt    46860
taaaagcaat atgagataca ggaagtatta aactggagat gtaatgccac ttggatggca    46920
tacttttaac attatttttt atttgtttaa atggaatgca ttttgcttat tagaatcatt    46980
ttggaagtgc caatttgctt ctgttaattt acattaaaga ttaaaatagg aaccactggt    47040
gaccttctaa atcaaagttc ttcaaaacgg ttgtttaaaa cagcaagaat tacagaacta    47100
agtattgtat agctattaaa actgaaaatt atgtagcagc agtccatttt aaatttaaca    47160
atttaaaatg atacttcaaa atataaaaaa tacaaggaag aatataagat gcttatgtat    47220
ctgtactgcc aaaatttaac aaatgttaac tttttgctat cactgtttca gaacttttta    47280
aaataaatta aaaatataat tgaagattac taatctcatt cttttgcctc tcttctcaga    47340
ggtaattact tttctaaagg tatcctgtaa gttttcaata cttttttacca catatttgta    47400 taaaagata aacagtactg atttcctttt aaaatgtgaa taataatata ctgttggcat    47460
aactttttaa cttgcttttt tcactcagtg tttatttaca tcaagattta ttcatgttga    47520
tatttgtatg tacttaaagt ttgtttattt tatcctctga attattagtt tggtccatta    47580
tttatgatgt ttagtttgat tacttggtta aggtggtgtg acctgatttc tctattgtaa    47640
aagtatcctt ttcccttga taattaatca ttaatctgtg gggtaatgcc ttgagactga    47700
gtaaacattg tttctcaaca gcctttcacc cagtgttttt aacatccatt attgatttat    47760
gcctgaatta ttggttacat tgatgcttgc aaaatgattt tctacatcta ttattctttc    47820
cacatttatt agctggcatt cttctttctg taaaggagtt tctgtccttt cactaagggc    47880
tcatggtttc ttcattaatt cggtgaacta aaatccatta ttgttatgta gtcatgcact    47940
gcatatacga cattgatccc atgagattat aatggagctg aaaaatttct atcgcatagt    48000
gacgttgtag ctgttataac atgttaggac taacgtcaca accaacatat tacatgtttg    48060
tagtgatgtt agtgtaagtc aaatctactg tgctgccagt ctaaaagtat agcacatata    48120
attgtgtaca gtacataata cttgataata ataataaaca gctatgttaa cggtttatgt    48180
atttactatg ctatactttt tgttgttatt ttgaatgtac ttctacttat taaaaaaaaa    48240
agttaactgc aaaacagcct caggcagttc cttcaggacg tactccagag acattgttat    48300
tataggagat gacagctctg tgcatgttat tgtccctgaa gaccttccag tgagacagta    48360
tgtggaggtg gaagacagtg atactgatga tcctgaccct gtgtagggct agtctaatgt    48420
gtttgtttgt gtcttaggtt ttagcaaaac agttttaaaa gtaaacagg aattttttaa    48480 aatagaaaag gcttgtaaaa taaagataaa aggaaagaaa atattttttgt gcagctgtac    48540
```

```
aatatgttag ttttacgcta aatgttatta caaaagtcag aaaagtttaa aaactaaaaa    48600
gtttatatga gctaaggttt attattgaag aaagaaaatg tttaaaaata gatgtagtgt    48660
ggtttgagtg tatatttaca aagcctacag ccgtgtgcag taacgaccta ggccttcaca    48720
ttcactcttc actcaatcat taactcaccc agagcagctt ccagtcctgt aagctccatt    48780
catagtaagt gccctatata ggcatatgat tttaaaaaat cttttatact gtattttttac   48840 tgtacctttt ctatgtctag atattctcag acgcaccatg ttacagttac caggcagtat    48900
tcagtacagt aatatggtat acaggtttgt agcctaggag caatgggcta taccgtgtag    48960
gcttgtgtaa atacactctg tgatgttagc acagtgaggg aatagcctaa caaacacatt    49020
tctcagaaga tatccctgtg ttatgtgac gcatgactgt gtatcctttg gtgactcaaa     49080
ttgttaaaat ttagccagcg agaactcaat cagtctggtt tctgtttctt tgacatgccc    49140
cctcattttt atagcaccag tttgctttgt ggcacaacaa acattctct ccttacctta     49200 tggttttctt accccagacc tggacttggc tattttacca aaagttcttg tttctcttag    49260
tggggaatgg tatttggaag ccaacatcat ggatgcatta ctgggtgtca ttgcttctat    49320
tggttctttt cattagacag aataagaaaa tatactttta aaaactagtg atatttgaat    49380
tcctagtgac accaaggttc ttttctttcc ttgtttcata ttcctcttcc ataatgaaga    49440
tccagtttac caataacatc aatatatgtt tattcatttg ctctgtctta tacatgatat    49500
aacattggaa ttactatagc aataccacta ctaataataa tctcaataaa gtttaagatt    49560
tctatgcagt ttttatttta tagcgtatag cccagtgaag gtatatagtc agatcgctat    49620
gcttatagtt attttaatta tattttttcac ataggcaatt tgaaactttt tctaatagga   49680
aggttaagcc tatttactta tcttgacata actagtatgt ttaatctaac tgatatgttg    49740
tatttactgt tgttttatgt tatatatgtt tttctttttac tcttttttaa aaagttattt    49800
ttactaatac aaaaatcttc ctttctctag atatttagaa tgttggtctt agctcttata    49860
gtttcccagt cttttttggta tttttgttgt cattactatg tttaattttg ttaactagaa    49920
ttcatgtttt cttttcttca tccatttaat tgggctttat actttttttt ttttttttg     49980 agacagagtc tcgctctgtc acccacacta gagtgcagtg gcgcgatctc agctcactgc    50040
agcttctgtc tcccaggttc aagtgattct cctgcctcag cttcccaagt agctgggatt    50100
acaggtgctt gccaccatgg ctggttaatt tttgtatttt tagtagagac agggtttcgc    50160
catgttggcc aggctggtct cgaactcctg acctcaggtg atccacccac cttggcctcc    50220
caaagtgctg ggattacagg catgagctac cgtacccatt ctatatattc ctttgcataa    50280
atgttgtgtt ctgaggaaaa tttgtgtctg agcatttaat aatttaaaaa attaccatgt    50340
gagtggattt attttatatg aataatgtgc cacatgtaag ttgttctgca gttgattttc    50400 ccttttttgtg gagcttttac aatattgtta gtatgtttac ttgtcccttt ttcccttgt     50460 atgtgtagcc aagtaattat aaaaaatggt gcactttgcc atatctgagc ttctcttttt    50520
cccctcaagt agatactgtg catttgaact gcaaaaaggg tcatattctt gctttatcta    50580
taatctcttt taaaggcaaa ggctgatggt tactttttct ttaataagaa tcttgatttt    50640
tcattttgta tatttgatat ttatcatttt aagaaaaaaa aatcctctat acatagttgt    50700
tagaaattta tgtagaatgg atgttggaac ccaatcataa ggctgtaaaa ccataaaata    50760
agtagtaata aattttaaaa aatgaatagg atttgtatga agaaaataac aacacttcat    50820
tctaggatca aacaaatgaa gagagagcta ttttcagaa tgaaaaacca aatagtgttg      50880
```

```
catgtagact ctattcaaag ttctagtctg taaaattaat agcaattcta gtcaaaatag    50940
ctgttttatc ttttgagaag ttcgggaagt tgacaatct gattgtcaaa tatatgttgt     51000
agagtatgtt aatgaaacta tccagtgtaa aatttaaaaa taaagaccag tattgttata    51060
ttgtactgta ttgcttgcta tactgtagtg gtgtagtaat taaaacacca ttctagtgat    51120
acaggaatag ggtccaaata aataaaaact gagaaggaaa ttgtatacac atgcaagtgt    51180
gtgtgtgcac acacacacac aacacagaaa gggtttttt ttgttttttg ttttttgtttt    51240 ttggagacag ggtctcactt tgttgcccag gctggagtgc agtggcatga tcatggctca    51300
ttgcagcctt gacctcccag gctcaagcaa tcttcccacc ttagccttgt gagtagctgg    51360
gactatgtgt gccactgttt ccaactaatt tttgtacttt ttgtagagac tgggttttc    51420 atgttcccta ggctggtctt ggactcctgg gctcaagtga tccttcacct cagcctccca    51480
aagagctggg attacaggtg ttagccacca cgcccagcct caaaaagctt tttttttttt    51540
tccctataaa gagccatata tctaaaaagg gaaacagatt tgactctatt acaatggaat    51600
tctgtgagag aaaacatttt aacaagatca gactatctag tagaaaaata tttgtaacat    51660
atagcaaagt tttaacaaac ataataaaga ccttctaaaa attaataaaa ttgaaaaaat    51720
gggttatgaa taagtacaaa taattcaaag agtgtacaca aattagtttt catagaaata    51780
tgcataaaga tatatgtaca agtatgttaa ttttagcatt atttataata ccaataata    51840 atattccaac aaaatagttg gaataatctg aatgttcacc agtagggaaa tggtacatct    51900 gtatttaga atattagcaa gctgattaaa aagaataaga tctttgtgac caggtatggc    51960
aaaatatccc acattattca tgaaactata gaatgatctg tgtagtatga tctcatttac    52020
ttagctcagt aggtctattg tttgtggtaa acttaaaatt attttattta tcttatagga    52080
tagggacttt taagttaacc tattaatatt attaggaact aaaatatatc actgtaagag    52140
aataaagaca aatatagaat aaaaggaact aagaaaaata ttttacatca gattaattgg    52200
aaatattggt atgaatccat gagtaaataa agaaatatct ctccccccac cctgttctgt    52260
ctaccagaaa atataagaag catggacaat ctcagtagca atggttacat gcatcttggt    52320
tgctaaatat ggctccccat tgaaagaatt caagatgtct tagaaaaata gatgatccca    52380
gttcttagga aaacacacag caagccagaa acaaggaag tggtgaaaaa ctgaggaatt     52440
atgtaaaaaa gaaccaactc aaaggagttc tagtggccac ctccgaaata atgattgcaa    52500
tcacaggcat atcttggaga tgttgtggat tcggttccag accatcacaa taaaacaaat    52560
attacaataa agtgagtcac acacattttt gttttcctag tgcatataag ttatgtttat    52620
acaatattgt agtctgttaa gtgtgtaata acatgtttaa aaaatgtaca tgccttagtt    52680
tagaaatact ttattgctaa aaattgctaa taatgatcaa ctgagttttt agtgagttgt    52740
tctaatcttt ttcctgctgg agggtcttga ctcgatgttg atgactgctc gccagtcagg    52800
gtgatagttg ctgaaggttg gggtggctgt gacaatttt aaaaataaga cagcaatgaa     52860
gtttgttaca tcaattattc tttgatgaaa tatttctctg tagaatgtga tgttgtttaa    52920
tagtgtttta cccacagtag aaattcttca aaattggagg gcagttctct caaaccctgc    52980
tgctgctttg tcaactaagt atgtaatatt gtaaatcctt tgttattatt tcaatgatgt    53040
tcacagcatc ttcaccaaaa gtggattcca tctaaagaaa tcactttctt tgctctttt    53100 tataagaagc aacacctcag ccattaaaat tttattttga gatttcagca attcaatcat    53160
gttatcaggc tctgcttcta gttctcttgc tatttctatc acatctgcag tgatttcctc    53220
cactgaagtc ttgagctcct cacatccatg agggttggga tcaacttctt ccagagttct    53280
```

```
gttaatgctg gtgttttgat ctccactcat gaataatgaa tgttttgaa ggcgtccaga   53340 ttgatgaatc cttcccagaa ggctttcaat ttactttgcc cacatctatc agaggaattc   53400
ctatctatga cagctatacc tttatgaaat atatttctta aataataaga tttgaaagtc   53460
aaaagggctt ctcaatccat ggcctgctga atggatgtgg tggtagcagg catgaaaaca   53520
acatgagtct tctggtatat ctccatcaga gctcttgggt gaccaggtgc aatgagcaat   53580
gtcagtgagc aatgagtagt attttgaacg gaatcttta ttctgagcta cagtctcaac   53640
agtggactta aaatattcgg caaaccatgt tgttaaatag atgtgctttc atcaaggctc   53700
tgttctgttt gtactgcaca agccagagta gatttagctt atttcttaag ggccctacaa   53760 ttttggaat gataagtgat cattgttcca cttggaagtc accagtagca ttggctccta   53820
acatgctgag tcagcctatc ctttgaagtt tggaagccag gtattgactt atcgtttcta   53880
gctaggaaag tactacatgg cttcttcttc cagtagagag ttatttcatc tcaattgaaa   53940
atctgttgtt tagtgtagcc accttcatca gtgatcttag ttagatcttc tagataactt   54000
gctgtaactt ctccatcagc acttgctgct tcatcttgta ctttatgga gacagcttct   54060 ttccttaaac ctcatgaaat aacctctgct agcttaaaac ttttcttctg aagcttcttc   54120
acctctctca gccttcatag aattgaagag aggactttgc actgaattag ctttggctt   54180 aagggaatat tgtggctggt ttgatcttct gtgcagaaca ccaaaccttt gtccatatta   54240
gcagtaaggc tctttcttgt tcctattatt catgtgttca ctggagtagc acatttaatt   54300
tccttcaaga acttttcttt tccttttta acttggttaa ctggcacaag aatcctagct   54360
tttggcctat cttggccttc atcattcctt cctcactaag cttaattatt tccaactttt   54420
gatttaaagt gagtaatgtg tgactcttct tttcactcca acacttagag gccattgtgg   54480
ggttattaat tggacaaatt tcaatgttgt tttgtcttag ggaataggga ggtctgagga   54540
gagggagaga gatagggatt ggctggtggt tggagcagtc agaacacatg caacatttat   54600
cagttaagct tgccatcttc tgtgtttgtg atttgtggtg gcccaaagca gttaaaatag   54660
taacatcaaa gatcacagat caccataaca gatacaataa taatgataaa gtttgaaata   54720
ttgtgagaat tactaaaatg tgatactgag acacaaagtg agcacatgct atttgaaaaa   54780
ttgcaccaaa tagacttgcc caatgcaggg ttgcacaaac cattattttg taaaatccac   54840
aatatgtttg aagtccaata aaatgaaatg cagtacaagg aggtataccct ataattgtaa   54900 aacctttgat tgaaaaaaat aatccatgag tccagagaga taagaagaaa aggaaggccc   54960
tcctttagag aattgtagta gcagtgttag aactggaaaa ctgtactgta aactccaaag   55020
aaacaatctg tgccaacagc atcaatggat gccaaaacct ttaggtgtaa gagtgctgtg   55080
aacatgatac gtatgcagtg gtgcccaatt attctgtaaa tcttgtacga ctacaaaggg   55140
aaaatgtgcc tttgcaatag atctatagat tgccacttga actaagtggt cacacttata   55200
atgggacagc ctgataccat gttccttttg ttatgatata atgcggaatg atgtaacctt   55260
gggtgtattc ttgcctaatg tttatctaca atccagtcag gtttctagac ttgatcttgt   55320
ttccaagaaa tacaggaagt tgtggagtaa gtcagaatac attctgggaa gcagtcagac   55380
aaatctagga tgtgggacat tctgtaagaa aactggccat gagtcctgac acatcattgt   55440
cttaagaaaa agatatgtgt gtgtgcgaga gactattcta ggacaggcga gaccaaagag   55500
atttaacagg caaatgttat acataaattt tcatttgccc ttggattgct ctctcaaccc   55560
tgaaggctta aaaatagata tctttgagac acttgagaaa acatcaagat actagcttac   55620
```

```
cttatttta  ctttttttg   actagatgtc  ttaatggttt  tattactttg  taagacttgt  55680
tttaaaagat  atgtttcact  actcagtata  gtctatgata  aaatcagtaa  atataaaata  55740
tttgtcattt  gcatctctta  ggaggttcgt  ctccattgat  gaaagctcag  cttatgtgta  55800
actgtcttcc  aaagtagctt  gcttggaagg  acattcacta  tcatcatatt  ctgctttatt  55860
tcatagctgt  gtaatcacat  ctactacatc  cttgtttatc  gtttattaga  ttactgcttt  55920
taagcctatt  ttagttcttt  aatctgagaa  taacagttga  ctcagttaat  ttcattaaag  55980
caagattgcc  tgtaattttt  ttataacctt  agaaaagtac  tatgcccaac  agcaaaacaa  56040
aaacctaatt  caaaaatggg  taaaggactt  gaacagatat  ttctccaaag  aagatataaa  56100
atggccaata  aacacatatg  aagagtctca  acaccagtag  tcattagaga  aatgcaaatc  56160
aaaaccacat  ttagatacaa  tttggctatt  agcaaagaca  cagaaaatag  caaggattgg  56220
gaaggatgtg  gagaaaattg  gaaccatgcc  tgcactactg  gtgggaacgt  aaaatggtac  56280
agctgctatg  aaagacagtt  taccagttct  tcaaaaagtt  tgatgtagaa  tgattgtatc  56340
atccaacaat  ttcactgtta  ggcttatctc  caaagaatt   gaaagaaggg  acacaaactg  56400
gataacttat  acagcagtgt  tcatagcagc  attactcata  ctaaataaaa  gatgaaaaag  56460
gccaaatgtc  tgtgaacaga  tgaatggaca  aatgtgttta  tacatatagt  agaatattat  56520
tcagccataa  atacaaatga  aattttggta  catggtacaa  catagataaa  ccttgaaaac  56580
attgtgctaa  gtgaaataag  ctagacagaa  aatattgtat  gattctactt  agatgagata  56640
ccccaagctg  gcaaatatat  aaagctggca  agtataatag  aagttactaa  ggcctagggt  56700
gagggaggaa  tgagaagttt  gcttaatgag  tatagagttt  ctatttggaa  tgatgaaaag  56760
ttctggaaat  gaatagtggt  gataattgta  caacattctg  aatgtactca  atgctactga  56820
attgtccatt  taaaaatggc  taaaatagta  cattttatgt  atattttatg  atacaaaaat  56880
atttttaaag  taaagttttg  tattttgatg  ttacttgtga  aaaatatttt  cactaataaa  56940
attttgttgt  ttcattgctg  cctctttgaa  aatgtattaa  aaattatatg  cattttgaaa  57000
tattacagct  atataaatga  aaaagagtat  cagtaaagaa  ttttagctca  atactctcat  57060
atcatgttat  ttattgtcct  ttctgtttca  cattaagata  tacagagtca  acaatttaaa  57120
tttgcagatt  aaaaaacact  ttctgctttt  ggccctatag  aaataaacca  aactggaaaa  57180
ggtgtcatgt  ttcctagatt  gtggacacag  aaaaagaaga  gctcaaaagg  acaagtaact  57240
cagcacagta  gatggttatt  gacctgatca  tatttaagaa  tatcctaaaa  atgcaaaaat  57300
gttaagaagc  aaaactggga  aatactggga  tgatatatga  aaaattcaaa  tgacaaatat  57360
gcagtggttg  agtatttatg  ggttttttg   gggtttacta  ttttttcccc  caaatttaat  57420
gtctcctctt  ttaaatactt  ctaccggatt  ctctttagat  gatgctgcaa  ttggattgag  57480
acattttcat  tgtttggctt  tgtaagattt  ccaaatgcgt  atagttgtta  aaatacgtat  57540
tcaatgaggg  tggaaggaaa  cacacaaaaa  tagaagtatg  tcactctggt  aagagatgat  57600
aggtccgatg  actgctaata  cttttccaaa  tggccttatt  tggatccttc  ttagaacttt  57660 tatattttc   taatattgac  ctacccttt   ggaactagag  tcccattgtc  aagaactgtg  57720
aagaatcttg  acattttacc  ctacttgcaa  gctagcagtt  actcagttgt  agttttatgg  57780
atggtggtta  aagatatgag  actcctgagt  tggagttgaa  ggacagttta  ttagtgcagc  57840
aagcagtagc  agtgaccaga  gtattagctt  ccttttttt   ttttgccgc   ttttccaagc  57900 cctggttccc  atatagtagt  gtgaagagga  gggctcatg   atgcttgtac  acactgtgga  57960
ttgcataaca  gatgcggaat  cctcagcttc  ttacagaatc  tgaatagtag  tgtataatag  58020
```

```
gaagtaagaa tgcctttctt tgctttggag caagatactg tctttgtctc ccaacactat   58080
tgctgtaaaa gtatcctcaa aaggatagtg cagaccaaaa gggtagttga gtgtcttgct   58140
cctaagaggt gcagaaacat gagagtctca tagaaaattg tctcccaata atattttctg   58200
ctcatttcta tactattttg tcttaaggca aattttttc atgagtatac cactctgatt   58260
tatctgacag aagatagtga agtatctgtt caaatagtta gctggctttt aaaatcaggt   58320
tatttgcttt cttattgttg agtttgagag ttctttcttg attctgggta cagtcctttg   58380
tcagatgtgt gatttgcaag tattttctct gagtctgtga cctgtctttt catattcttc   58440
aatctctttt acagaacaga agtttctaat tttgattact atcaggtttt tctcttatga   58500
attgtcttag gaacttttg cctagttgaa aatcacagag ttttttcct tgttttgtcc   58560 agatgtttta ttattttgtg tcttacattt agatctgtga tctgtcttgc attacctttt   58620
gtttgcataa gttatgaggt agagttcagg ttcattgttt ttgcgtatgg atatttactt   58680
gttctagcac tatttgttga agagactatc ttttccttcg gtgaactgcc ttttaccttt   58740
tgtcaaaaat caattgccct tatttgtaag tatattttgc tggatttatt attctgtttt   58800
gttgatttct gtgtgtgtcc tcttgctaat acatcattgc cttaaatagt aacagtttta   58860
tggtagttat tgaaattagt gttctcaaat tttgttcttt tgctgaattg ttttggatat   58920
tatagtacct ttgcattttc tttataaatt aggaatcagc ttgttgatag ctacaaagat   58980
actttgagat tttgattggt gttatgttta atgtacatgt cagtctgagg agactgacat   59040
tttgccaata ttgagccttc caatccatga atatagttat ttttccatt tttaggtctt   59100 tgattatttt catcagtgct ttatagtttt cagcatgcag atcctgcaca tattttgtgg   59160
aagtgtatct tttccagatg ctattgtgag tgctactgct ttaaaaattt ttgatgtact   59220
aacttattgc tgatatataa aaatatggtc gattttaca tattgatttt atattccaca   59280
acttgttaaa atcataatca taaaaccctt tggattttct atatagacaa catgcttttg   59340
aataaaggct gttttacaaa atttcatttt aaatttgtat accttttatt tcatttcctt   59400
tcttaattgc acttgctaga gctttccagg acaatgctga atagaggtgg taaaaacaca   59460
tctttgcttt gttcctggtg ttttattact ctttattat tagtgttatg tttagagatg   59520
gggtcttgct cagttgcgaa ggctggagtg caccggtatg atcaaagctc actgcagctt   59580
caaactgttg ggcccaagtg gtcttcctgc ccgccttcc tgagtagctg ggattacagg   59640
catgtgccat catgcctggc taagtttttt attttttgtg gagatgaggt cttgctgtgt   59700
tcacaggctg gtcttgaact ccagtctcaa gtgatcctcc cacttgtact gggattacag   59760
gcattagcca ccacacttgg cctcttatta tcattattat tattaatata tataaataaa   59820
tatacatata tttatttatt gagacagagt cttgctctgt cagccaggat ggagtgcagt   59880
gccacaatct ctgctcactc aacctctgct tcctgggttc aagtgattct cccacttcag   59940
cctcctgagt agctgggatt actggcgttt gctaccatgc cggcgtggt ggctcacgcc   60000 tgtaatacca gcactttggg aggccaagac gggcggatca tgaggtcggg agatcgagac   60060
catcctggct aacatggtga aaccccgtct ctactgaaaa tacaaaaatt agctgggagt   60120
ggtggcgtgc gcctgtagtc ccagctactt gagaggctga ggcaggagaa tcacttgaac   60180
ctgggaggtg gaggttgcag tgagccaaga ttatactatt gcactccagc ctggcaacag   60240
tgagactcca tcttaaaaaa atgttatggg atgaaatttt aaaagacct tgaaagata   60300 caagataata ggattcaatt ctgtataagg tagagataaa ctgttgattt gtactagttt   60360
```

```
gatttgtgaa atattacaat taggctaaat caaataggtg atgggtaatt tgagaattga    60420
tttctaatgc tttgtcctag atcattcaaa atctgatgtt cacataacta cttagaactc    60480
ttgactagtt gtctgtgctt tttaaaaacc tttacctggc tggctacaac tttctaccg    60540 ccataattaa aattgaaaac aaaataatta gtctcttagg aaaataattt acgaacacta    60600
tctaaacatg ctagatttaa aactaccagt atttacatgg ttagaattca tgagcagtct    60660
tcattagact tactgctgaa tgaccagcat acagtcgctg aattcattgt gcatctttta    60720
agggaagatt gttttgcttg tatctttgca gtcttctctg agatctttaa tgttactaga    60780
agttataaag tttggttaat tttcctaata agcctttatc tgattctgtg gctatttag    60840 gtttgggatg ggatctgttg tcttaatttg gtcaccattg gctcttggct tcaaagtgga    60900
ccctaaacta tattcctagt ctgtctagta tttgtctttt ttttgctgag atatgtgacc    60960
cctggggagg tttcccttat tttcaataag ttaatctttc tcttttagga agaaaagaca    61020
aatttctcat aagggaggga ttttttcctt ttttgttcta gagtgccttt caaattaaca    61080
attttgttca tatcaaaagt tgcccataat gatcactgta agtctcaagt tattcttggt    61140
gaaaatatgc catttagaaa gataagtatc tgaattggaa gaagcatgtt tcatgcttgg    61200
agaggttgtg gagttagact gacttaaaaa gtcagttttg tgcagcctgg gcaacataac    61260
aagacccagt ttctatgaaa ataaaaaaaa aaattaggca ggcgtggtgg tgcacacctg    61320
tagtcctagc tactccagaa gctgaggtgg attgcttgag cccaggagtt tgaggctgtg    61380
gtgagctatg gtaatgccac tgcacttcag cctgggcaaa agagtaagac ctcatctttt    61440
aaaatatata tacaggtttt tcttcaaaag attccaaagg tactgcttta aaaaatgtaa    61500
gattttctaa gcaacagggc cgagtacttt gctttaaagt ttttatgaat gcctggcttg    61560
gctatctggt tgcttttgaa atcaacatct tactaaacta ttaatgcttt taaaatgtgt    61620
gcagaattac atatttgtaa atttaacttg agtctgtcta ggaaagcatt agcaagactt    61680 ttgttttttgt ttttgttttt ggagacagtc ttgctctgtc gcccagcctg gagtgcagtg    61740
caggtcactg ctcactgtag ccttcacctc ctgggctcat gctatcttcc cacctcagcc    61800
tcctgagtag ctgggactac aggtgtacat caccacaccc agctaagtaa aaagatgtat    61860
ttttcataga gacggggtct ccctatgttg ccaggctggg cattagcaag attttacggg    61920 aaatttttttt tatcattagt agaaaataat aaggaatccc ttgctggtaa aatttatatt    61980
gaaactactc ttaaacatat ttatataaaa tgaccagaga tatttaattt acctttatat    62040
aataaataga aataaattga aatacattat taggagattc agattttta attagtaaat    62100 tagtgtgatg gcttaaagtt attgagaggt aattttcat ctttgattag aaaaacttaa    62160
aaattgtata atttacatac acaaagtata tatgagcttt ttatattgat gaactttaca    62220
aaatgaacac acttttgtaa ccacaaccca gatcaagata tcagcttctc aggagcttcc    62280
ctgtatctgt catattcctt tacatgaaag gtaattaata ttctgacttt gtaattagag    62340
attagcttgg cttttttttg aatttttata aatcataaag tatataagac tatatgattt    62400
ataagttttt tcaaactggc ttcttttccca cagcagtatg ttttttgagat ggatatttgg    62460 cttacagcat ttttcatttt cactgaggct tagggtttca ttgtgtgaat atccttagtt    62520
tatttctccc ttctgctgat ggacattcaa attatatcaa ttttgggttc ttacaaatag    62580
tgctgctgtg ataattctcg tacatatttt tttgtgcata tatgtacaca tttccattga    62640
gtgtatgctc aggggtagta tcacttagtc tttgggttta tcttcagctt agtagacact    62700
tccgaacagt ttcccatact gtttgtatta tattattata cattttacc tgcagtattt    62760
```

```
tagaatgtca gttgctacag attttttgctt acacttggta ttgtcttttt ttagataaaa   62820
gttagtcatt ttggagggta gtagtatgtc tttgtgaagt tttgtttggt ctttagccta   62880
tcttaaaaat cggtttgttt tttttgttga gttgaagtat ttttaaagaa tatattttgg   62940
gtatgagtct ttagtggaac atgtgcattg ctgatatttt ctcctacact gtagcttgca   63000
ttttcatttt taatttattt aaattttatt ttattttta agagacaggg tctcactctg   63060
tcacccaggc tggagtgcag tggccttatc atagcttatt gcggccttga actcttgggc   63120
tcaagcagtc ctcctgcttc agccttctga gtagctggga ctgcaggtat gtgccaccac   63180
acctgggtaa tttttaaatt ttttgtaga gacagaatct cactatgttg cccacactaa   63240
tctcggactc ctggcctcaa gcagtcctcc tgcctgggtc tcccaaaatg ctgggattac   63300
aggtgtgagc cactgcgcca gtcatttcct tctttccttc tttctctctt tccctctttc   63360
cctctctctt tctctcttcc tttctctctc cttccttcct tccatccttc cctccctccc   63420
tccctcccca ttcccttccc cttccctccc cctttccctc cctgcttccc tccttccttc   63480
cctccttcct tctctctttc cttccctcct tccttccctt tttccttcct tccttccctc   63540
cttccctcct tccttctctc cttccttccc tccttccttc cctccctgta attgtaatga   63600
aattgtttgt ttgtaatgaa attcagtttt tttatgtgct gtgtattaaa tctatgccta   63660
aatatcgtga cagtatttat cttgtcacta tataagcttt attatttaaa attttatata   63720
tataggtctc taatatatct tatttttttt cccaccttttt ctgtggcttg tggatagatg   63780
ttattcatttt tactgatttt gatttttaaca gtagtagtca tagaaaatct attgatgtgg   63840
cttactcatg agaaagcatt tttattttta tatgtgatat tataatttct agtatggcaa   63900
cattttctgc tagttatgat atgtgatttt tactctgcag attctttaag aggaatttaa   63960
aaacagcttt attcctgact ttagagaagg cagtcagttt tacttaatat gtcattttat   64020
gtcttatttg ttatgtttg ttttgagga gtcatactgg tagtttaaaa atactgagtt   64080
ttatcatcaa atgcagctac aatgtttaag cagatgactt aatctccgtg aggcatgagg   64140
tgattaaaaa atgtatgtat atgctttttc aaatacagag taaattgcct ggcagacaag   64200
aagagcttca taaatattat ttagtgcttt ttattctaga ttttttgaaat aaattggact   64260
cgacttgatg caaaggattt gtactataag tttattataa aattattaac cgctagcttt   64320
tgtaaaatagt aaaattgatt tgcccattat acatttcttt ttgttatgca taaaatattt   64380
taatttttaa gtaccaacat aggatggatt tttaaatgct tcctcatgtt aattttttaa   64440
taaacataga atgaatactg tgtgaaatat tttcccactt tattggctct gttttaactc   64500
agtagactct atagttagat tgtctaggtg ccacttaaaa gatggtaact agataccaga   64560
atgtgttaca ttatatgttg attgtcagga agaactgaat gcatgaatgc ttccctaaga   64620
cattgttagc atgccgtggt cttgatctat aatttttgt ctaagttgtg atagagctca   64680
ttctttacat ggtctagtaa attcagccaa tgtctttata attcattagc atctctatat   64740
attacctata aaatttaaat tataaggcta tgaaaaaatt gtttcatatg tataatatac   64800
caaagtttta gcatatggtt tggattttaa actgttttac tgaaacaaat taccgtcatt   64860
aaatggaatt cttaggtaga cattacagag taggtgtaac tctgaagttg aaaatggttt   64920
catcttcttt tttaaaaaat tttattatat agggaatctc aaccaccagc aggattttaa   64980
aaaggctatc taaatatttg gtaagtaaat attctccatg ttaaatattt tgcgtgttac   65040
ttaagtttac acatatgcta catgaatgac atttacaata gtgagtgtaa attatagtta   65100
```

```
taattaatat tttaaatttt acttggttac tagaattttt gtctccttaa acctattcca   65160
atccttttct ctcttgttct ttatgttgtg tccagagatt ctttcagtgt acagccttat   65220
tattaagagt tcaaggaaag aaatggtttt agtgagcagg aatgctaata ctttatgaat   65280
aaaacaggat ttcccctact tgagattttg tagtatttct tttttgtgaa acactaata    65340 cagatttgtt ctttagccat ccattgcttg actcctcctt gtatttaggt cctgtttgct   65400
gcaacatgcc aacatgaacc aaatactgtg gtcagggtct atgcatttcc tgtttagatt   65460
attctttgtt ccaagcttaa aatatgaaaa attttgtagg tgtctgtagt taagaatttc   65520
ataaacttat gatttcatag ataaagcttt tactttttta tttttgagta aaggtaggtg   65580
agtcaatctc agaatgtatt ttacttcaac tacatagtat tttatacctg tgtactatgg   65640
tgattatata gatataaaat gatttggtta atcataatag attttaaagt tattaaatat   65700
gcttcagaat gggaagaag tgctgagaca ttgcataatg aggtgtcata gtataggctt    65760
ttggttgttt ttaatatagt caatagcaga ttattaagga ggaaatattt agtgataagc   65820
attggcttct tttattatac ttttttaatgt gtttgaaaca gcaaatattt gaccaaatta   65880
tttttcttaa attttatagt aactacagta ggtgcctaaa tgttcaacag ttatactgtt   65940
ctgtttactg taaatttgta ataaatataa atacttttag gagcaaatga tgccacagag   66000
atctcttaaa cagattttta ctactttaga aggtggtaac tgatttctgg agttgtatta   66060
agtacaaaag agtaacttat tgtcatttt tccctattg atgcgtatat ttgagttaga     66120
gggaagcagt cgtctttgtg ttatatgctt atcatgtata tttcatctta gcaaatttat   66180
taattttagt gacagtttta ttgagatgaa atttatatac caggagattt catctctaag   66240
tgtacaattc agtgatattt taatatattc accaagttat gcaactacca gtactttgta   66300
atcttaggtt actttcatca tccttcttct ggacgccctc tatcacccag ccctaggcaa   66360
ccactaatac actttctgtt tgtataggtt tgcctattct gggcatttta taaaaacaga   66420
atcataaaat atttgtcctt ttgtgtctgg cttctttaat ttagcatgat atttaaagct   66480
tcactcatgt tgtagcatgt atcagtgttt cattcatttt tgtggctgaa tatttctttg   66540
tatatcattt gtgtattcat cagttaatga gttgtatcca cttcttttttt tggctattag   66600 gagcgctttt ctgtgaacat tcttatataa gttttgtgta gatacgttttt tgagtatata  66660 tggatggggt gggattgctc gataatatag tacctgtgtg taactctttg aggaactctc   66720
aaaatggctg taccatttta caataccacc aacaatgtat gaggattgta atttctccac   66780
gacctcataa acacttattg tcagtctttt gtatttcagc cattctagta ggtatgaagt   66840
tgtatcccat tgtgattttg atttggataa tgactaatga taagcatcat ttcacatgct   66900
tattgaccat atatcttctt tggagaaata tctgttcaac tcctttgccc attaaaaaaa   66960
aaaagattat cttttttaatg ttgaatattg taaacattct ttatatattc tggaaactag  67020
tcccttatca catacatgat ttgcaaatat tttctcctat ggattatctc tttacttta    67080 tgatggtgtc ctttgaagca gaaaagtttt aattttgaag ttcagctgat ctgttttttg   67140
ttgcttgttc tttttggtgtt atattgcaga tttgttttta aataaatact cactgatagc   67200
ctgggtctat gacaaagttt taatcgtcat aggactacga aaaagcattg gcatttcttg   67260
tgtttgacag tcaaagccca aaggaggcaa ttatccttgt atttgtgctt cagttcctca   67320
gctaattgtt ttaagcaaaa ccttacgttt tgatcccatg tgttactgtg aaaatattag   67380
ctgtgtgtga tatgttttatt gatattagtc ttgtgaattt atgtttagtt ttttttggat  67440
tgaagaaggg agggggccatc cttaatagat gttattagtc cgttctcacg ctgctgataa  67500
```

```
agacatatac ccaagactgg gtagtttata aaggaaagag gcttaattga ctcacagttc   67560
ctcagggctg gagaggcctc aggaatctta cagttgtggc agaagaggaa ccaaacacat   67620
ggtgacagca aggagaagtg cagagtgaat cggggggaaaa gccccttata aaaccatcag  67680
atcttgtggg aactcagtca ctattatgag aacagcatgg aggtcatcat ccccatgatt   67740
cgattacctt gcactgggtc ccaccacaac acttggggat tgtgagaact gcaattcaag   67800
atgagatttg ggtttggaca cagccaaacc atatcaatag tttattatga caattactgc   67860
atattttatt tcatagttta agaaaccatt gcttttttaga ctaaggatta tcaggttctt  67920
atctttcttg tgaagaagga atagattttg ataatctcac tgattttaat cttgtacaga   67980
ttattattat tattattttg agacggaatc tcgctctttc gctcaggcca gagtgcagtg   68040
gcgcgatctc agctcactgc cagctctgcc tcctgggttc acgccattct cctgcctcag   68100
cctcccgagt agctgggact acaggtgccc gccaccgcgc ctggctaatt ttttgtattt   68160
ttagtagaga tggcatgtca ccatgttagc caggatggtc tcgatctcct gacctcgtga   68220
tccgcccacc tcggcctccc aaagtgctgg gattacaggt gtgagccacc acgcccaacc   68280
cagattattt ttaagcaatg atattttggt gttttttgtaa acttatgtat ggaatatgta  68340 agttttcct ctattaagta aatgtcttta attttttttt tttttgaaa tggagtctcg     68400 ctctgttgcc caggctggag ggcagtggca caatcttggc tcactgcaac ctctgcctcc   68460
cgggttcaag tgattctcat gcctgagcct cccgagtagc tgcgattaca ggcatgtgcc   68520
accaaacctg actaattttt gtattttttag aagagacggg gtttcaccat gttggtcagg  68580
ctggtctcaa actcctgacc tcaggtgacc acctgcctct gcctcccaaa gtgctgggat   68640
tacaggcttg agccactgcg cccagccagt gtctttaatt tttaaggtac caatttagtt   68700
ccttattttt tatcgttatg tgacgttatg tgatcagttg aaggtgtatt tcatgtattt   68760
tgacctataa tgttgtctag tttagtttct ggagaaatgg tgtgtaacag tggaatgtca   68820
cttgtcttca aagcattagc tttctgtgta aggttgaggt tgtaatataa atgcgctaga   68880
tgtgttttta ttaggggaat tgactattct tacctttcat gttatttgac agtattcttt   68940
gtcaacttca ataacggcc tattttgatg agattttata gtgctaggat cactgatatt    69000
cttgttagtt gatttaaaat catggtgttc attggctaac agtcacttga gtggctatta   69060
gatgggtaat attgttctct tttttttttt tttttttgag aaaagagtctc actctgtcgc  69120 ccaggctgga gtgcagtggc atgatcttgg ctcactgcaa cctctgcctc ctgggttcaa   69180
gcgattctcc tgtgtcagcc tcctgagtag ctgggattat aggcgcatgc catcatgccc   69240
ggctaatttt tgtattttta gtagagatgg ggtctcacca tgttggacag gctggtctct   69300
aactcctgac ctcaggtatc cacccacttt ggcctcccaa agtgctggga ttgcaggcat   69360
gagccaccgc gcctggccag atgggtaata ttgttctata cattgatatt cttatggttt   69420
atgttatagt attcatggaa atttagcaat ggaaaaggaa atgaaaaact tattaatgat   69480
gttgttaaat tttcaattgt gatgacagta aggaaaagac ataattgaga gctacctcca   69540 attgttata tcaaatgtgg taattaagag gattttggtg acctatttat ggctgaatta    69600
aggcaaaata gcttttatat ccgattcttt cctcttccct tctcttgttc tgtgtgctta   69660
ctatcataat aattgagtat acattaattt tctttaagta tttatattttt aaataaggtt  69720 ttgatgtcag tagagacttt ttttttttcct tgaaggtaag tacccttttaa accactaatt 69780 tgtcactaga gtctatagtc gcttccatat ataataggta gcacagcttc tcaggtcatg   69840
```

-continued

```
tcctgctttg ctgctctgct gaccaataat acaccttgga gatactggtt ctggttatat   69900
gaatagaaca attaaattgt tcttcattag atggatcttt gattactaat cttactcaga   69960
aaggctcaac tggacttgga ttattctaat tgccaatact gttttttgcac aaatgtctgc   70020
aaatcattga acagtaatac tgaccccttt ttcttccaat aaagttattg cagtaatcac   70080
atcattgcag agaatatttc ttaaaagctt ttttcaatat ttacttcttt aatgaaaaac   70140
ttaatccaga ttaagccaca tacatagacg tcttgactttt attattttga atacctgaga   70200
tttccaaaat ctctttaact gtcttcacac aatttctagt ctgtcatttt aattaattac   70260
aactgttcat ttcttctgct tttgtttcct cttcatgtgc tgcctagcgt tgctagagtt   70320
tcatcagttt cctgccttga gaggtttcta gtacaaatta acattttccc ttcctagttt   70380
atgcaggttc cttcctggta attttttatct ttttgatctg tttcattctg catgttagtt   70440
atttggaacc attctactgt gctcaaatga acagtcctat ccctagttct cttattcctt   70500
tttcatttca tattttatac ccttttttcct cagtctgtct taaagaataa agtgttttca   70560
tttcaaaagc ttattatctc tgttttttaat cttagcccctt ctttcctcta ctatttttct   70620
tcctcttaat gctccatgct gggttctctg ccttatcaga cttaatcttg aaaagtacgt   70680
tacttccttc ccattatctc caaggttgtt atagtccatt ctaggtgtct ccaatttctc   70740
aactcttact caattacttt ctgaagtttg actattattt ctactagtgt tcagctttct   70800
taagtgtaag taaacacatt tcttacttaa ctaggtagat aaacattagc tggacggatc   70860
tggccgtaaa catgctatta tttccaagat aaaactgagt tccaaatggc taaatctttg   70920
tcttttcact tttcatccat tcctgtcttt tttagcattt gttttttttgc tgcttaacat   70980
tcacttctcc tttgtcttct gtaataaacc ttaatggttt ttctcctctc tctggctaaa   71040
tgtttgtttt ctttgttact gctttcttct tttatatacc acttatatat aaattgggtt   71100
gaagctttgc tcttagctct ttttcattac acatcatttt gaggagatgg tctcgtgttc   71160
attatgtaga ttatcacaaa tttgatgact cagaaatacc acattttttct tagtgacctg   71220
ttttaccact ttctcagtcg ccaggtcctt agcaccccaa aattgttatt tcccagtgga   71280
aagtttgtct tgtacaatgc ttgctatatg gttggaacta agtaaatgct ttttgaatca   71340
tgaactaact ccttatctgt cttttttttt cttaagataa tggttttaac tgtccaccta   71400
ttctcatgtc acaagccctg taatatctct gaccacttct tgtctacact tgttaatatt   71460
agttgtcata ttttggtcct aagtttgact aatgaggaag atgacatttt tgtctgcaga   71520
tggtggaaat aaaaatcaca gagattgtga tttccttatg gttttgtggg taatggtgga   71580
gtttaaactt acaacgaagt ttctggtgac atgtttccta gttttcacag aaaacattct   71640
tttttttttt gagacagaaa gtctcactgt gtcgcccagg ctggagtgca gtggtgtgat   71700
gtgtcggctc actgcaacct ctgcctcctg gattcaagtg attctcatgc gtcagcctcc   71760
aagtagctgg gattacaggc gcccaccacc acgcccagct aatttttgta ttttttagtat   71820
agatggagtt tcaccatgtt gaccaggctg gtcttgaact cctggcctca agtgaccac    71880
ctgtctcagc ctcccaaagt gctgggatta caggcataag ccaccacacc cagccaaaaa   71940
cattctttat aatgatacaa gtaatatacc agacaagaaa ttactcagtg tactatgtga   72000
gattaaaaaa aaaaaaaaaa aaagactgga agtggaagtg ggagtacttc aaattcttgt   72060
ctgatgaggt aaagatttta acttggtgga aggaatagaa atcaaggatg tgagaaattt   72120
ttcattaatt agaatttcga gattcttctt ttaagaatgc agtgatgcta gtgaagtggt   72180
tgagtgaacc atctttcagc taacaattat aagatctgga caaaatattg aaagaaaaac   72240
```

```
tttaactgtt ttaaaagcca tggaaagtaa ccaaaaaagc aaagccagat gagagcctcc   72300
aactgcaatg tgtaattgta tgtttgtggc tttcttgcct tatggtgcat tttcgcctcc   72360
tgtctttcag tggcatagga aagaagttac gggtagcctg gcagttggaa atttactcag   72420
gggaatcatg gaagcaataa gtaagatcca aaatctgagt gtaaactctg tccaaatcat   72480
ggctaatcac gaaactatac atgcataggg gagaccccag gggacccagt gtaaaaacag   72540
gcagaaacaa gagcggaatc tgctcctgaa agaattgaac cctgtgagat tgtgattgc    72600 ttcttttttt gacagtacat ttctcaactt gcatgcaatt tgcgtggcca acagctggct   72660
tgaggtatca gagcacagaa catattgttg acagaagagt taaaatttag ggaacaaaca   72720
ctgaaagcaa gataacatca gaggatgtag gccacacatc tcagtataat ctctgcccat   72780
ttccttcact gaccaccaga ctacccaggt gcagagggga tgccctgggc atcaggttag   72840
aagaaggaag cagctggaag gtgaaagaac taagcaaaat cattgttgct tactataagg   72900
gagacacaca gtaagtcctc acttaacatt attgataggt tcttggaatc tgactttaac   72960
tgaaacaacg tataacagaa catttttttc tcatcagttg tataacaaag cagtgttaaa   73020
ggaaacgaca gtattcaagg accttgctgt ttgtgttttg cttcaagttg ctgtttccaa   73080
gacctatcga tggtattaag tgaggactta ctgaagtttg cagtttgagt ccatacgagc   73140
ccattagaat catacaacat gaaaaccaaa tggtcctttg aaagattgcg acaaaatctg   73200
gttgctataa cttgctattt acaatgtgta ttttcaacta aaaattatta gatatgcaaa   73260
taaagtggaa atatgactca ttttcaggta aagaaaatca ttcaatagaa attaaccccca  73320 agtatagcca gatattggat ttagcaagca aggactttaa aatagcccta aatataatca   73380
gaagaattta aggagtccta tgttcaaagg attaaagaaa aatacagtca cccctctgtt   73440
tccatgtttc tgcatttgca gattcaacca accgtggatc aaaaatagtt gggaaaaaac   73500
ataataaaat ttacagtaca gcaataaaaa ataatgccaa taaaaacaa taaagtcttg    73560 ttcagtgaat agataggaga tcaaaacaga gaaacagata ctgtaaagaa gaagcaaaag   73620
agaattttag ggttgagatc agtaactgga atgaaatttt tatattatat tttattttat   73680
tttattttgt ggtggagtct tgctccgtcg cccaggctgg agtgcagtgg tgcgatctcg   73740
gctcaccaca acctccgcct cctgagtagc tgggattaca gacatgcacc aacatgtctg   73800
gctaattttt gtattttag tagagacagg gtctcaccat gttggccagg ctggtcttga    73860
actccctccc gacctcaggt gatctgccta ccttggcctc ccaaagtact tgattacag    73920 gcgtgagcca ctgtgctcgg ccaagcaaaa cagttgtttg gagatggcaa aagaatcagt   73980
taaagataga ttaataaaag tcatctattt gaaagagaaa gaatggagaa aaataagcag   74040
agtttgagag accctttgggg taatacaatg tttgaacatg catctaaatg gagtctcaga   74100
tggggaataa ataatggctg aaaaccccca caactttggt ggaaagtatc aatttacata   74160
tccaggaagc tcagcaaact tcaagcagga taaacacaca caaaaaaaca gatgttagca   74220
cataagtggt caaattgctc aataccagag aatttcttga aagtagccag aaatatctta   74280
ccagaaacaa tggcgacctc tagccatgga tatggtatat tcagctgaaa ggcaaaaagc   74340
tatcaaataa gaattctgtg ttcagctaga agtgaaggta aaataaatac atgttcagat   74400
aaaccaaaac tgggaaattt tcaccagcca gccaccattg caagcatttc taaaggaatc   74460
aatttcaagg gaaatggcac cagatggcaa gtaccatcta caggaggaaa tcaacatcaa   74520
aactagtaaa tacataattt actctaattt ttataaacta tatttttcct tattttaaaa   74580
```

-continued

| | |
|---|---|
| acaagtacct gtgacttgaa gcaaaaatta tgatgctgta ttgttgggtt tataatggag | 74640 |
| tttgggaatt tacatattgt acaattttta atatgtaatg acatacaaat taacgtgtta | 74700 |
| atagtcttct aacttatgaa catggtatat ctcattaagg ttattgttta attttagtaa | 74760 |
| tgtataatag gtttctaaaa aacttaaaaa tgtggtaaaa tatgtacaaa ataaaatttg | 74820 |
| ccattttagc tgtacaattt ggtggcacag ttgcattcac agtgttgttc gttcattact | 74880 |
| acttttccca gaacttttct atcattccaa acagaaactc tgtacctact aagcagtaat | 74940 |
| ttcccatttc ccttccccga gtctctggca gtgtctaatc tactttctgt ctttatgaat | 75000 |
| ttggctattc tgtatttcat atatagtagt cccccttatc cacagttttg ctttccacaa | 75060 |
| ttttggttat ctgtggtcat ccatggtctg aaaataggtg attatagcac aataagatgt | 75120 |
| tttgagagac cacattcata taactttatt acagtataat tgttctttt tattattgtt | 75180 |
| gttgttaatc ttttactttg cccaatttac agattaaact aataagtata tatgtatagg | 75240 |
| aaaagacata gtatatatag agtttggttc tatctgtggt ttcaagcatc cactgggggg | 75300 |
| tctggaacat atgctctgtg gataagtggg ggactagtgt acttcctgcc ctaccccttg | 75360 |
| gtttggagtc gctgctgtat gaatataagg gcagtctgcc tgtgatgtga ctctccattg | 75420 |
| atcacctggg tgtatgaatt aattgctgtc tataaagagt cttggaatga ctattgagtt | 75480 |
| tgctctgtgt atgtatacat acaacagtat ggctactgtt gtagctgatt tggctatgat | 75540 |
| actgtagtat cttatttgct ccaaagagat ggagtagtga tgaaatctgg tttactaggt | 75600 |
| ggaagctagt gtaaaaatgg gtactctgtt ttattgaatt agcttgattg gaaaaagtga | 75660 |
| agtgctgatg gttttgaaaa tatgatgata atgatgtcat ccttctggtt taaatatttt | 75720 |
| gtagcacttg tggtagattg aatgctggtg tcggtagtaa agtcatgctg cagttatagt | 75780 |
| ctgaaccagc tgtactgttt tgggtagtaa cttagacagt agagaacacc acttttctag | 75840 |
| gcagggctcc tcacctctcc tagggggcca tttcactgca tcttggagtg aatatacaga | 75900 |
| gaggaagtag ctagatccta atttctacaa gttatatcag ttggggaaca gttgtggttg | 75960 |
| tcaacctgtg ttagggctgt attggttttg ctttcagttg tgctataaag tggaaaaaat | 76020 |
| tgaattgttt atttatctct tattgtgaaa ctttcctgtg gcccatagaa gtggcatagc | 76080 |
| aagctgaaca tagctgggtt tgttcttcat tgcaagatcc tacccccacc tcccttcctt | 76140 |
| tcctgcctgg tttcttgtgt ccatactgca agctctttt cccagttaga agtaagttag | 76200 |
| ttcactctta atagagctga tttacaaagg aatttatgt gtgtcatact gtttgattct | 76260 |
| ctgaaaggta gatatgggac tgtggtaaca atccagcatg atgttaactg tgctctcatt | 76320 |
| tttaaatgtg caaatggatg tatgtgaaat ggtggtttgt ctgatacaat attggctgct | 76380 |
| aagacatgtc tgacctagag cctagatgtg ttggcttctt aataatgctg gatgatgtat | 76440 |
| atctggatca ttcttttaa ttgactgaga tgatgcgtat cttctacctc ttgagagtta | 76500 |
| ggaatgtaaa gggcaagtga aaaatttgtt agatgctctt aaaagatgaa aatagatgtg | 76560 |
| ctccatcact agtatagttt cttttgacc actatgtcaa cctgtttaga aagtatatttt | 76620 |
| taggccgggc gcggtggctc acgcctgtaa tcccagcact ttggggaggc tgaggcgggc | 76680 |
| ggatcacgag gtcgggagtt caagaccagc ctggccaaca tggtgaaacc ccatctctac | 76740 |
| taaaaataca aaaattagct gcgcgtggtg gtgcgtgcct gtaatcccag ctacttggga | 76800 |
| ggctgaggca ggagaatctc ttgaacccgg gaggcagagg ttgcagtgag ctgagactgc | 76860 |
| accagtgcac tggcatggca acagagactg ccaacagagc gagactccat ctcaaaaaca | 76920 |
| aaacaaaaca aaacaaaaaa caaagaaagt atattgtaaa catcaaatta aagaatttc | 76980 |

```
ctgaagtaac ttttttttt tttagtaggg gtggggaaga tatgagtaga agagaaatga    77040
attggaaact gagtaccact acccttttc ttaccttcta tccagaaatc tttcttaaat    77100
tccacagtat cagtgtaaca tcttttatct tttgagctgt ctttgagatt ctttactttg    77160
tctccagact gtttgttagg attctactag agaagttgtt ttcagatttt aatttctctg    77220
ctccatttta atcttctaat tttttaatga aaaaaaatcc agttttattg agttcttttt    77280
tttttttttt tttttttgag acagagtctt gctctgtcac ccaggctgga gtgcagtggc    77340
acgatctcag ctcactgcaa gctccgcctc ctgggttcac gccattctcc tgcctcagcc    77400
tcccaagtag ctgggactac aggcgcctgc caccacgccc agctaatttt ttttgtattt    77460
ttagcagaga tggggtttca ccgtgttagc caggatggtc tcgctctcct gacctcgtga    77520
tccgcctgcc tcggcctccc agagtgctgg gattacaggc gtgagccact gcacccggcc    77580
tattgagttc taattaatgc ataatttgtt gagttttgac gtatatgtgc actcatgaaa    77640
ccatcaccac aatgtatata tccagtgaat atatacatca cccttaaaag cctcttgta    77700 atctcttcac tccccacttc gcaggcaacc actgatttgc tttctgttac tgtaggtcag    77760
tttgtatatt cttgaatgtt atgtaggtag aatcatataa tgtgtctcct cttttgtctg    77820
acttctttca accctagctc aatatatttg agatttgtct atattgttgg atgaatgatc    77880
aaaactttgt ttttgttttt ttaactgggg aatagtattt cattttagt atatagtaca    77940 atttattttt tgcccatttc catttagctg ttattgctgg attgggttat taacagttat    78000
tgactattat gaataaagtg gtcacaaatg ttggtgcatg gttttttatg tggacttgtg    78060
ctcttatttc tgctatgagt ggaatggctg attcatatag taggtgtatg tttacctgta    78120
taagacactg ccaaactttt ccggtttgta tcagtttata ttaccacttg cagtgtatga    78180
gcattccagt tgcttcacat cctcagaatt cttggtatgg acagtatttt aatttgattt    78240
gttttagtag ctgtataata atgtcttatt gtggcattca ttaatcatta ggaaaatgcg    78300
aattatgttg aacatcttta cctatgcttg tttgccattc acatcttttt ctgttgaagt    78360
attttctcga atctttgctt attgatttat tgatttattt attttgagta agagtcttgc    78420
tctgtctcct aggctggagt gcagtggtgt gatcatagct cactgcagcc ttgaactcct    78480
gagttcaagt gatcccctg cctcagcctc ctgagtagct gggactacag atgtgtacta    78540
caacacttgg ctgtttttt ttttttttt ttttttttt aaggattttt ttaaagagat    78600
agggcctgac tgttgcccag gctggtctca aacttctggc ctcaagccat ccttccactt    78660
cagcctccag aagtgcaggg attacaggct tgagccacag tgcctaaatt ttttcattgt    78720
attgtttgtc ttattattga attataagag ttctttctat gtgctaaata ctagtccttt    78780
ggataattac ttgcagattt ttttcagttt gtggtttgcc ttttttcttt acccatgtc    78840 ttctcaagtt caagtctttt attttgatga atacacattt atagtttttc ttttatattt    78900
catgcttttt gtgttgtatt ttggcaggcc aaataatgac ccctgaaaga tgtccatatc    78960
ctaatttcca aaagctgtat atatgttacc tgatatggct ccacaaactt tgcatatgtg    79020
attaagttaa agattttgaa atgaggagat tagccaggat tgtccaggtg agcccagtgt    79080
aatcagagag tccttgtaag aaggaggcaa accaatcag ggcagaagag atgaatgact    79140
gcagcagagg ttgaatgat gtgctttgaa gatgaaggga aggggccatg agctaaggcc    79200
atgagataat aaatttgtgt tgcttttacac caagtttata gtaatttctt accacagccc    79260
atatagattt tgcctgtaag tggaatgccg ctgtaacaaa tacctaaaaa ggtgaaagtg    79320
```

```
gctttgaaat tggggtattg gcagaagctg gtagaatttt gaggaacata atggagaaaa    79380
cctagattat cttgaatgta cagatggtag aaatacagat gttaaaggct ctgctggtga    79440
tgccccagaa ggaagtgagg agcacagtag agaaaatgtg tatcgtctta gagaatacct    79500
aaatcatcat aaagagactg ttggtggaaa tgtgaacatt aaaggtgctg ctgcttgtga    79560
gtgctttgaa ggaaatgagg aagatgttat tggaaactga agtgaaggag atccttgttt    79620
agattgtaac agaaagttta cctgaattcc gtcctgtagt tatgtgacta actctcctgt    79680
gttgcctggg tatagcagca atcatttata catacatttg cagttctgtt ctgtacttgt    79740
tataaagtag ttttaattaa agtgacagat ttatgttttt ataaattaaa tttatattta    79800
aaaaatcagt atttagaaca aatatcttag tggactatat tcttgagata ttattattaa    79860
agtcttttta cagcttcctt tcaaataaat ggatatgtaa tttaaacctt taatttctgg    79920
atttcctgat gacttttctt taaaaagaat aatttttaaa aacacatttt aatttataac    79980
taaaatggtt atttaaggaa acacatatat tagttttatt tagatatatg ctttttttatt    80040
attaatttgg aaagtggagg tgcattgttt ggtagaataa ttttaaatgg tagctcttgt    80100
taatggctaa tatttattag tggatacaac ttacaaatat ctgtacattc agtctttatc    80160
cttatcttcc atatcttttt cttctgcatt ctaggttttt ttgtttgttt tttggaagga    80220
ggatatataa agtaattatt actacatttt tagctgttgc caagttgaaa gtcagtgttt    80280
agttttttt aaaagggct atttagtgtg gaattcctaa atattatagt tccctcttct    80340
gtccttcag agctattgca ccctgttaaa ttttttttgc attcagttca accagtgttt    80400
gaaaattacc aatagactta aagtacttct ctgaagttag aagagctcct atgtctgatg    80460
ctatattgct agtatttcta ttcaggttgg aatttggaat agtcattatc aaaagttatt    80520
tgtaggcaaa agaaaacaaa aagaaaaaag ttatctgtag gaaatattgg agactgggt    80580
acaaggtaag tgacacagtg aagaagcaca gacaatttca gaatatgaga cacctaacat    80640
ggtttctgca aggtattggc gtggaaaaaa aaaaaaaagg ggggggggc ttagagagtt    80700
actctccagt aaaagagata taagaagcag tactatagtt atatacaaag ggtagttctt    80760
tggattctgt ttagatcaaa ttaactagaa aatacatttt taaaataaga tgggggaattt    80820
gaatattgac tggtattact taatatcgtg gaaatatact tattttgaat gtgtatagtg    80880
actttgtgag tatgaaaggc agtggccaaa ttatttagtg atacataatg atgtatatgg    80940
atgagggaag taatgacgtg atgtctggaa tttactttaa aataccttgg aaaaaatgaa    81000
taaaagatag ataaagcaat attgctaata tttcagtacc tgttaaatat aggtgacagt    81060
atatatatag aggttcatta tactccttc tccacgtttt gaaaaattc atttaaaaat    81120
tcaaaaaaat tctaaaaaat attttttctt ttagaaacta acacatgctg aaaaaattca    81180
aattttgttc actgaccacg ttttttgctgc caccactctt tcaacattta aaaaatgttc    81240
ttaaatctt aaaaattcga tttacattt cattaagaaa atgaggcatt tgctggccat    81300
ttcatccttc ctcttgtatt ttttctcctt acctgctgcc accgtttact agaaaaatat    81360
ttctcttgtt ttttctgtac cttctccttg aaatataaaa gttcagtgaa ggcaggagag    81420
attttagccc gttttgtat ggctgcatct tccttatcca tacctgcata gcatgtggta    81480
ggtgctgagt aaatatttga atgactgaat gggtgactga atagactgaa tgaaccagag    81540
ttgtagaaga catggggtga cgtgggttt ggctaaggac agaaccaagg agaacccctt    81600
tgaaaattca ctctgtggga tttacagggg aaaatgtggg ctactacata agaaattaag    81660
ataagaaatc atctttcctg tttgactgta aagccttaat atttcaagca tttaacatat    81720
```

```
tctcagcata aataattaag ttttttttctt cttttttctg aaacagtctc actctgttgc    81780
ccaggctgga gtgcaatggt gcgatcttgg ctcactgcaa cctccgcctc ccaggttcaa    81840
gtgattctcc tgcctcagcc tcccgagtag ctgggattac aggcatgtgc caccacgcct    81900
ggctaatttt ttgtattttt agttgagacg ggggtttcac catgttggcc aggctggtct    81960
caaactcctg acctcaggaa cccacctgcc tcagcctccc agagtggtgg gattacaggc    82020
gtgagccact gcgcctggcc agtaattaag tttttatact gtaagttctc taattgtctt    82080
taatgtattc ttgaaagtgt tttcctccta atttatttat tactgcaagg caatccgttc    82140
ttgaggttct atttaaagtt tatgtatttc ttctcaggaa aaaaaattac ttaaaactag    82200
tggtttgtac agtcaagatg agttttagaa gctgttctta aatttctttt ttatgttaaa    82260
catatataat gtcacatttc ccttttccta acaactgatc ttctttcttt ttcaacgtgt    82320
atttataagc tagattttta aattttgctc cagggactgc tgtagttgtt ctactactta    82380
aaaaaagaaa gatgttagta ttgaacacta ttctgagaca cagctgataa caattgtgct    82440
caacaatgaa gatggctaaa aattgggttt taaaaataac agtgaaaatt cagaagcatt    82500
ttatacttgc tattctaaag tgagtatttt tctaatctct gctttaaaat tactgaagtc    82560
cttttaatga ccaacgctgt attttaagga aaaaatgtga gcaaagattt ttagtgattc    82620
taaatttgtt ttgctctctg gatctcttta aactttttaaa aattattgaa gaccccaaaa    82680
agctttgact tatgtgggtt atctctcttg atatttaccc tgttagaaaa taaagctgag    82740
aagtttaaat agttttcatt tattaaattt atttaaaaat aacagctaat tacatgttta    82800
cacaattaac aaagtctggc ttacaggaag acagttggat gctcatatct gcttttgcat    82860
tcagtttgtt aggatattac atgctctata ctctgacaaa aactttactt tgtgtatact    82920
caagagacag agtaaaaaac ataagtaaca tcttagtatt atagaaataa ttttgatctt    82980
agaaactcca tgtaagtgtc tcaggaactc ccagggttca tattttgaaa attgctggag    83040
tcatctctca gaggctatgt gtgacaaatg gtgttttttaa atgaaacaat aattttttaaa    83100 atatagtgtc aattggctaa gtttttattt gatacttttt ttttctttttt ttttttttgag    83160 acagggtctt gctctgtcgt ccaagctgga gtgcggtcac agctcactgc agcctccacc    83220
tcctgggctc aagtgatctt cccactttag cttcccaagt aggaagtagg tgggactaca    83280
ggcaagtgcc accatgcctc agtaattttt gtatgttttg tggagacagg gtttaccatg    83340
ttgcccaggc tgctctcata ctcctgggct caagcagtct acttgcaccc aactcagcat    83400
cccagagttc tgggagccgg attcttattt gatacatttt tacctttagg ggaactataa    83460
aaattagctt atgcttattt atgcaaataa atttgagcat tgaggaagga tgtctcttgt    83520
tcagggttgt gtttgtagat ttcacatctt ttagactacc atttaagaga agtgatcacc    83580
ttgtatctta aggaaatgaa aatcatttga tagaaatgga ttgttaaata ttttttaaaac    83640 aagttttgac agttacttgc aattaaaggg gaaagcaact ttaaaatgca ttagttaatt    83700
gaagaaatac tcaagatcct taattgttgt tagtgagcaa gtattaatgt tctttcctct    83760
ttgaaaacgt atctgtacct agacaaagtt aattataaac tttttcataa acaatattat    83820
gcttcttttt cttctaattt ttaaacctta tctttgttgg tttgccttcc agctccatct    83880
atctgcaacc taagaatcaa caatactata catcaaatta gctgatgtgg aaggaaaatg    83940
ataaataatg aaaatacgtc atattgctta tactctaagt tataattaat ataagatcca    84000
agggatattg gtgtggggga cgaggaggaa ggaacattgc aagtcaagct atttcacaag    84060
```

```
tattctatac ctttgaatct tttatttcat agttttcttt agaaacaata gtgatgcaga    84120
ctgaatagct agtaagataa cttTcattaa tagcagtatg gcagggattt ttaattgatg    84180
cttgttggta atattagaca catgatttat ttataggctt ttaattagaa aactaataca    84240
aatatcaaat tgttatggac aggttataca tttttTggca acacaaatcc taccaggttt    84300
taatgcctgg tacttgtttt tacattagta tgtggtatta attttttcat tactactctt    84360
agcttccCta gcttacccat tgctaggag tacatagcag cactaggaca tttttcgcta    84420
acgtggctgg catgcatctg aaagtgtgac agagcagggg tatagctaga ttttagaagt    84480
tcttttgctc atttaagaaa cttaaacttc agatttgata gtacttcaga ttctacataa    84540
tgtgctcttt cgatgaatag ctgtgtagca gcagcacagg aaaagcagag ttcttggcaa    84600
tacccagttc aattgcatct gcagatgagg atttaaaatt ctgtgcagca gacagtacct    84660
ccagcaggcg agtaaaaggt tactgcatta ttttTcttgt ttgttaccat agcctttatc    84720
taccaaagga ttttTaaaaa attgaatgtg aagtgcatgc ctgttTttag atattctgga    84780
aattgattta agtataacat gaatatcaaa agggcagtgc aaggtgaagg cagaggcagt    84840
gctggatctt tttagcttta aaccagggaa gaaattgagc atgttacata cacaaagaag    84900
aaacctttca gtgtcacaga caatgggaag ttttaaaata cgtattttaa ttcaaggtgt    84960
ttattattta gttttagact atcttcccca aaaagggtgc tcttacatta gcaatcattg    85020
gtctatgaat gttcatttaa gttacagtaa tttgaagtat gattatttgt gaagactata    85080
aagtatttgt attaatgcga ccctcccttg tcctggaaat tgtaatgtgg attaattaca    85140
ttgtataaac aaataccttt gtgcattatt ggcaaaggta gaatgcttaa gtataaaagg    85200
tatagtatag ctagcatact taatattgtt gcttatgttt tcagggtggt ttgtggtttt    85260
taaaataatc ttttaaataa aatgcagaca agtaagtggg agaaaattca gtatcaaaac    85320
aatgaggttt ttgatggctt tttacttgtg gtcagtacct acctatatag ccatatgtcc    85380
ttttttctca ttaaaactct tctaacattt atgatagcag gagcctcctt ggattatcca    85440
gcttgtttat tacatcatta tctgcaccag tattttTgct atagattttt attgttcatt    85500
acttctcaag tctacataaa gtatccagag ggaatttttg cttgtatatt ttattcagtt    85560
accctcctac cctcttccat cagtcctcaa agatttgtat tagctactgt ctacattttg    85620
tttatttaaa aaatacttag gcctatattt ttgtattgta gattgaataa taagattgaa    85680
aacaattctg taaattaatc tatagtatag aagtaaaatt tgttgattat tcttactgtg    85740
agtatttggc aggcttcttg aattgtagag tcataaaagg tcagcagttc tgattggtaa    85800
gttaaagaat ccatccagta atttgctccc tgttgtttct caaagcaatg cagcagcagt    85860
tcttttccag atattaaacg gttcttgaac agtgtgtgtg gagacgggga ggggtggagc    85920
tcattcctgt tggttgttga atcgtgtgc atttacagag ggaacaggtt ggataggctg    85980
agctgaagga gtaggcaaac agatctaaac tgatggaaga cagaaagtgg ttagtataat    86040
tttggggtgt cttgagtttg ctccttTgtt aagtacttgg gctttaatat aaaacaattt    86100
aaaatattaa agcaccttac cttctttcta aagagtagct gggagacttc tgttttaata    86160
tccagttTTt cttggcgatg agtttgtggc tggcatcttc tgtagcaaag ctgttgtttt    86220
attcttTttt agtagtgttt ctttcagcca gagagctgca gaatgaggca gtttgacaat    86280
tttgagtata tatgtgacat caccagttct gatttTttaa gtcaaattct catctaatga    86340
gcaagtcaat gtgtggctgt ggctgcagca ttatttcttc tttaatgaag aggttgagcc    86400
gttcgacctg ctgctccgat tgttctcttt gtagccatac atcagaccag ttgcagagat    86460
```

```
tatccatcga atgtcccagg caaccaaagg taactacata gatttatttc aaataaaaat   86520
atgcaatgaa aatggatgca ttatgactaa gaccaaatga ttaaaaataa aagaccaatt   86580
aaagatgttc ttagcagttt tcttgacctt gcagtagata tccaatatca ttttgtcatc   86640
atcagattgt gtagcaatgg aaatgcactg cagtaattga ttttgtaata ggatcaggtg   86700
atttactagc tgcactgaca accacttgct tgcttgctct gagctgtgga gcactctaat   86760
ggatgttgtg atttcagcct ggagtttatg tgagactgcc ggccacttaa agcagcagca   86820
cttattttaa agattagatt agttttctt tcttgttttc ttcgtttcaa gttttgtgag    86880
tagcctcagt aactttatgg ttaagttgta tgccttcatg aaattttaga gattatatat   86940
tatttcattc atcaattcat agtctttctg ctccatattc ctagctaaat atcaacatat   87000
tctggtattg accatgagag catatctcta aaatatgaga gttattggta actatgctgt   87060
gttatctaaa tgaagtggaa tattcctcac attcgtagat ttcattagct tcagactcta   87120
gctgtaatta gaatgatggt aaggttcttg atctcttgag ttgtactgca gttgttttgc   87180 atccttttt ggtcttttac tttcttagtg gtttcatggg taaggcacca tttaggaaat    87240
atgagttgta ttacttctaa gggatactga tgaggatata taaagctatt ttaaagtagt   87300
gtttaaggat atagcaaatt aaaaatctaa tatcaagtat tataaatttc aaagtgatta   87360
ttttaaaata attttgttt tccttttcta tgccttttaa acaaataatt ggttcaaata    87420
tagaagtgta ggaatattgc taactgtaaa atagaactac tgtcatagaa actcagatgc   87480
tgtcaaagac tttgattact taaaagtttt gctgatggtg ttagattaga aaagaaactc   87540
tcttccactc ccttcctcac caatacctct acctcatgta aagtgtttta tacagactcc   87600
accacataaa aatactgaat tctttatcat tccctgtttc tgttcttgcc atgatagaga   87660
caccatttct ctcaaccaca tctaaaaaca tttacaaaaa ttaaataaga ttaacaattt   87720
actgtagtag aaacggggca taaaattgtc atcacatgtg gtattcaaat caccatgtta   87780
agagaacttt ccttttgat gtactcaaat agtcacttgt agtgtttgaa gccttagtgt    87840
ttctagaaag ttgaaaatat tatctgtgct agtctgcaca tttcctttaa ttcagatact   87900
ttaaacatta attatggaaa attgaaaata atttaaacac tagtatttgt aatcttttat   87960
tattcaacag gtaaaaagtt tatagactct cttgacttcc aagaaaaaaa cccttctgtg   88020
aacactgatg aacataagca tgttaatatc atttaggatt cggtcaagga tgtgtctgaa   88080
tttcatatat attgaaaatg tttaatgatg ggccaccagc aaattaatca tggatatgtt   88140
ttactggagt gccgtctatg acagcttctt ttcatgatgg gttcagcaaa taggaaacga   88200
ggaagtaaac accagagtgt tgactacttt ttataaaagt tagaaagata actatgattg   88260
gtctgtgatt agacagtatt ttatgtaaaa taaatgggca gcgtgaagtt ctagcctcag   88320
tggagctgcc ttttctaaag agccctggat cgagcattaa aagagttgga tttaatttgg   88380
ctctgccatt aatctatttg ataaccttga tcaaattatg tatgaacatt ttaaagtccc   88440
ttaaacatgc tcttaaaatg tccattaaaa agatttcaat ttacccttac cagtgggaag   88500
tattagaata cttgaccttg aagctataga agttagagtt aggaagaagg atgaagtttc   88560
ttaaagaatc aagttgtagg tgatgttaaa acctctcctt tcactttta tgtctttttt    88620 tggggggtg ggtgggtaac atgttttgc taagaatact gttttatctc tttgatatcc     88680
aatatttcct aagtaggata gtaattctgg aaattatcct agtggttaat agaatagacc   88740
tgggattaaa atctggtgct gccaattttt tctagacttt ctaacaaaga taatgtcatt   88800
```

```
agggagttta ttcagtacct aggatatttt ttagtaaaca cgttttaaga aggttggcca   88860
ttatgttatt ggtgctttct tcctgtatgg cctattagat aagcgctgtg cagtcatctt   88920
tgttgcctag gcaaaatggt tgtaggttc attgattgaa ctcttacttt ggaccaagtg    88980
ctgtactaag cactttggtt tttttttttt tttttttttt tttttttttt aaagacagag   89040
tcttgctgtg tcacccaggt tggagtacag tggcgcgatc ttggctcact gcaacctctg   89100
cctcctaggt tcaagtgatt atcctgcctc agcctcccaa gtagctggga ttacaggcac   89160
ctgccaccac acccagctaa ttttttttgta tgtttaatag atgggggtt ctgccatgtt    89220 gcccaggctg atctctaact cctggcctca agtgatctgc cccgcttggc ctcccaaggt   89280
gttgggatta caggtgtgag ccactgtgcc tggcctgtac taagcacttc tatgttaatt   89340
atgtcattta tgagaaagac tctaatgatt attttttaaag atgagagaac tgaagctcag   89400
agaggttcta caactcctaa aaatcacaca actgggaaat agcagaacca atgtcaaaac   89460
tttaggcatc agcctgctgc tcaaaggaag tgctcattga agcgcttcgg attttgaaat   89520
ttctgataag tataatgcaa atattttta aaaatcccaa atctgaaaca tttctggttc   89580
caagcatttc agataagaga tactcagttt gtatttgtac tttcaattaa gctgtgagtg   89640
tagagatgaa gccaaatttc atctgaagat gtaatataaa tgattaccta atttttttag   89700
tcttgaataa gaaatgattt gttcacctct tactcagcaa taattcgtag gaaaaattat   89760
tcatataaag catatttgta ctatttggag taatgttttc caaagtgtgg ttcagggctg   89820
ggcacggtgg ctcacattgg taatcctagc gctttgggag gtagaggcag atgggtcgct   89880
tgagtcgaga agtttgagac cagcctggga cacgtggcaa aacctcatct ctacaaaaaa   89940
tacaagaaaa ttagccaggt gtggtggcat gtgcctgtag tcacagccat gtaggaggat   90000
catctgagtc tggcaggtcg agactgcagt gagctgagct attattgtgc cactgcagtc   90060
cagcctggac agcagagtga gaccctgtct caaacaaaga aagtatggtt caggaatcac   90120
ttgtatctat cactttggat ggtggttaaa agtaccagtt tacatcaggg cacattgaaa   90180
gaatcaccgg aatgggatcc agagatcttt gttttttaaat aagcctctca catgattctt   90240
ggttatacca aattgttaca accaatgata ttgagaatgt tttcctgttt taccttgttt   90300
ctatgccttg cagcttttcc tttaagaatt tgtttacaaa ccatagatgg tttgtaaaat   90360
tatccttctg acttatggtg aaatgtaaat tggttctttt gtggtactca ttttaggaac   90420
ttgtttagga ttaaaagtat tcataaactt tgactcagaa aacctacttc taggaattat   90480
agagataatt cctaaggaga tactcagatt cgcaggaaga cttaggcaca aggatgttcg   90540
taccattatc atctataatg gtgaaaaact ggaaacaact caatttcaaa catcagataa   90600
atggtttgtt ttttatatcc atttgtttgg actaaccatc cagccataaa atgttatatg   90660
gggaagattt tgtaagacat aggaaagtgc tcatgattta atgtaaagtc tcgaagaata   90720
taaaattatg gtcatacata tatgtacata tagtgcatat ggtcttaggt taaatcatat   90780
gaaattaccg ttttgtagg tcaagagtag tagaatatca gcattttcat gtagtgtaac    90840
ctaacatggc acccatttt aaagcacatg tttgtagaga agcacatgtt tgtagagaag    90900
cacatgtttg tagagaacgc tttgtagaga aggagctgga aggaaataca gcaaatttat   90960
aaagtgatta tctctggatg atgatattat ggataatttg aaatatttca tctttacatg   91020
tcttatgttt tcaaattttc tactatacct tagactcaac ctttgaaata ggacaaagta   91080
aattaataaa acagggaaca gttgcaaact ttctctgaaa aacattaaaa ttttttagaa   91140
gattgtaaat cctttaagct agtataagga cccctttata ctaatattct taactcttgt   91200
```

```
attaattatt gagtgtgttt atgcaaatgg atcatatatg cctttaccta cccacccagc    91260
aaattttgat tggattttaa tctgcagtag aaagtgtctt tcaaaagaag agaaaaaaat    91320
caattttcaa agttttaaa aagaattggg ttcttaaaag accgccaact atatgcagga    91380
gtcagttggg tagccacgtt aagcacaaag ccctgtttta ggctgtgtgg ttttgatttt    91440
taattgtaat ttaactgatc gataaaactc tgtagattaa aattagtaat ttgtgtattt    91500
attttaaaat attactgtat ttttttgaaa ggaaaatgtt tctcccactt tcatacactt    91560
taatcgttta attttaaaga aatagcttaa ttaaagtaac agctaccata ttctggttat    91620
ctgccataca ccaggtttg ggtgcttaa tatgttttt gttttgtttt gttttttga    91680 gaaggagttt cactcttgtt gcccaggctg gagtgcaatg gtgcgatttc ggctcaccac    91740
aacctccgcc tcccgggttc aagtgatact ccggcctctg cctcccgagt agctgggatt    91800
acaggcatgc accaccacgc ccggctaatt ttgtatttt agtagagaca gggcttctcc    91860
gtgttggtca agctggtctt gaactcccaa cctcaggtta tccgcctgcc tcggcctccc    91920
aaagtggtgg gattacaggc atgagccacc gcgcctggcc ttgggtgctt taatatgtta    91980 cttcttcaa tcttcaccta gaatgtatta attagatatg agctttgttt tagcgttgag    92040
gaggcactga aactattata agctttcctg agatcatatt aagtggtgga tctaggtttt    92100
tacctcagta atgtctaact taaagaccca tgttcttatc cctgatactg tccttgttgg    92160
tctgtctgaa acttttaagt gttcataact tgggaaacaa aactgttgta taagccttcc    92220
taattcagac tgtcaaagtg tagagcaaag tatataatga gtcattattg ctgatttta    92280 ttcaactatt tgttacctgt cctttaatct ggtcagtaca tgtgtactgg catttaacga    92340
tcgcctgcta atagctaacc tcttgtgtaa accactggaa atactaaaac agagaagcca    92400
aaaattactt ccttggagtt tacagtccta atgagagaga cagacaacaa aatagttaca    92460
aggtatttca gaacataggt atggaataga acctgttgga acagaaagtt tttaaactaa    92520
taatgtttgg gagtagtggt gaagagttac ttgggaagcc atcttggaag aggtgaattt    92580
agaaggagcc atagatttcg tttttgctac cagcctagga atttacattt taatacaaga    92640
acccctgcct ccagagtgat ctgtaattct actgaagttt gagaaccacc actgtagatt    92700
gtagttgatg ctacgagaaa gcatataata ccctgaggaa gctgtgtgga gtgggaaatg    92760
agaagttgga aacctcagag caacaacatt gctttgataa gtaggggaag ttatatgata    92820
gttacgatta atatattata agcaatatct tttagtgcct agaagtaaga ttggaaatgt    92880
cttgaatttt gtataagatc acaaaactta caggaagaat atcaaaattc cgattgaggt    92940
tacttttttc tgggagggat ggtgaaatgt tattctttac cctacaatgt gtgattaaga    93000
gtgaataaaa atcgtgttaa cctttttaaag ataatgttta agaaacaggt ttaattttta    93060
aaagaaaagt gagcatagga gcaaagtttt gtaacatatt ctgcttctat ataggaaatt    93120
aattcctaaa ttttggaaat gactagttga aagtaatagc agtctatcct ccaaagagag    93180 cttttttaaaa tttatttttt agaatcagac ctgggttaac ttttagatat aatttggcat    93240
aaccagcaag tcattggtta ttcaaaaata aagattggaa ataattgcca tatagtcttg    93300
gctctttgcg tattttgtga tactgattgt tgcttcctcc tttacttcca ttttattatt    93360
agagcttcat taagagtgaa ttgaaagaa aactgaattt tattatttta aaaatctgaa    93420
tagttggatt ggggcaactt tcttcctatt tatgagactt cactcattta tgttggtctt    93480
atattgacat taaagaatca gtgtcatata ctggtgaata ttaacaaaga gacaagatta    93540
```

| | |
|---|---|
| agattaaaga aattgaacct ttaagcagga ggcgtgtgac taatggagca aatttctgaa | 93600 |
| aggcttaggg gtagagaaaa tcaaagctac tgatggtatt aatagtctta gaaatgatgg | 93660 |
| agattacatt tttcctctca gagacaggcg acaaagaagg gaggagtaaa gaaacaaaac | 93720 |
| ctttgagatt gagatatcac aagttgatag gtacacagct ctctgaaagc ttcagtcatc | 93780 |
| tcaataagga gaggaacata cttagccata taagttcgag ttgctgaata tacattctat | 93840 |
| gtaggtaggt ctgtgtaatt ttgatacgta ttttctgttt atcacagtgg aaattgttct | 93900 |
| tgatcaatgt ttttatttca ataagaaaga tatattgccg cttccatctt aaaatttcta | 93960 |
| catagaagag acatgacgct tagtgaacgt tattgaaaaa aaaaaaccgt ataaacttaa | 94020 |
| gcaatgaaga aagagaaaca gtgtttcaga atgttacagt attgaacctg aattggtaga | 94080 |
| gagaatagaa agtggtgtga acagtcaggg tccaaatgac attctatata aagcatatag | 94140 |
| gacatgattt ggagcaggga gtgggatggg gaatgcttag attacatctc tttactagat | 94200 |
| gggtgtactt gttctgtgca aggtaccatt ttctcccctt ttttgttagc tcatatatcc | 94260 |
| cttcccagtt ttgaagagtg ctccactggt atttataact ttagtgattt gacatttcag | 94320 |
| gatatacctg tttcagaaaa tcataagaag ttttaaaaat gccttgatgt aaaacaaaat | 94380 |
| ttcaggtaaa cttaaatatt ttaagttttt aataatttgt gttaccaaaa ttaaatttg | 94440 |
| gttagagttt gacattccta agtgatagaa tcatcttaaa cacatgttgt caacagaaat | 94500 |
| ttgaatgctg aagtcaattt ttgttattgt tattgttctg cttagtgaag aaatgtatcc | 94560 |
| tctctaacca gggacagtat gtactgcttt ctccttaata ctttgagatt ttcataaaga | 94620 |
| aaataatttc aaaggtgttg tgctgcaagc taaagagatt atttctaaag gaagaatttg | 94680 |
| tcattctaat ggttgtcatc ttccttgtgg cattattata aaattaagaa actgaaaaaa | 94740 |
| aattttttta gaagacatag tatataccag aatttaaatt tagtttggca taagaggcca | 94800 |
| catattctac ctatgctatt acagtctgta tttgttattg cctaattttg actcattttg | 94860 |
| aatatctcac tccagtcctt tttattagta tttcttaaaa caaaaatggg caatatgttg | 94920 |
| gattgactga aaataatttt taagtgttta gtagcaataa aatttaatct tttagtgcag | 94980 |
| attggtttac cccataacag cacatatgga agaagtaaag ccaggtctgt atgaagcagg | 95040 |
| aggtgacatt ggacttttt tttttttttt tttttgtgac ggagtcttgc tctgtcaccc | 95100 |
| aggctggagt gcagtggcac gatcttggct cactgcaagc tccacctcct gggttcacac | 95160 |
| cattctcctg cctcagcctc ctgagtagct gggactacag gtgcctgcca ccacacctgg | 95220 |
| ctaatttttt tgtattttt agtagagacg gggtttcact gggttagcca ggatgtctca | 95280 |
| atctcctgac ctcgtgatcg gcccgcctca gcctcccgaa gtgctgggat tacaggcctg | 95340 |
| agccaccgtg gacttcttta aataaccata gtacaggcag ttacttttgt tatataacag | 95400 |
| tatagttgtc tctgaagaaa acctgaagct ctgcaaaatc gggccctgaa aatcggtttc | 95460 |
| tgagtggctt gttcctgtgt aaacttgtaa tctctgtagt aacgaaacca gtacccattc | 95520 |
| taataaaaat attatatagc taaatattta ccccagttag ttctaagttc taggatttat | 95580 |
| gctttctcct ttgaaatgta ggtcctcgag aacattcatt tctacttatg atgaaattgt | 95640 |
| gaaaactagt aaatcgatc cagggtgtag ttttttatcag ttgcctctca ccccttaaaa | 95700 |
| aaaaaaatta acgtgggaaa aatattgtca tggattttct atctgtactc acagcttgac | 95760 |
| cagatggttt taacattgtg gaatgcctag cagtttaaag ccattaacta gcctctggtt | 95820 |
| accctcttct ggatttctag tttttttctt aaggtcatca tgtattgctt aagctctgtc | 95880 |
| tttgtgagaa agcttgtccc tgctggcttt aaaactttac tatgctgggg aaaattttgg | 95940 |

```
actaaagtga cattcacatt atactgacct catcgcccaa atgatgaatg aatgaactaa    96000
tgtacactac aagaacatgt cttaatagga aagtagactg ttgtctgtag ttgtcccatt    96060
gttttatcat tgctgctact atattgacat gaagtagcag tgggtgtgca tgtttgtata    96120 tttttctgt  gctgttaaat aagtccacgc acatctccca tgtgggtagg gtagtactgg    96180
gtgatggagt aggtttacca gtaccatttg tcccttactt tacttgtata gctttatgtt    96240
ttaaaataga gtgtttttgt tttttgaga  cagagtctca gtctgtcacc caggctcgag    96300
tgcagtgatg taatctcggc tcactgcaac ttttgcctct ggggttcaag tgattctcgt    96360
tcctcagcct cctgagtagc tgagattaca ggtgtgtgcc actcctggct aattttatg     96420 tttttagtag agacagtgtt tcaccatgtt ggccaagttg gtctcgaact cctgacctca    96480
agtgatccac ctggcttggc ctcccaaagt gctgagatta caggcatgag ccaccgtgcc    96540
tggccacttt ttgttagaat aatactttg  aagataccat ggatttggtt ctagaccact    96600
acaattaagc aaatatcata ataaagttag tcacaagaat ttattgtttc cccagtgcat    96660
ataaagttat atttacatgg cattgtagcc tattaagtat gcaatagcat tctgtctaaa    96720
aagtgtgcat accttaacta aaaaatactt tactatttat ttatttattg agacagtctt    96780
gctctgttgc ccaggctgga gtgcagtggt atggtattgg ctcgctgtaa cctccgcctc    96840
tcaggttcaa gcgattctct tgcctctgcc ttccaagtag ctgggattac aggcacccgc    96900
caccacaccc ggctaatttt atattttag  tagagaccgg gtttcaccat gttggccagg    96960
ctggtcttga actcctgacc tcaagtgatc tgcccacctc tgcctcccaa agtgctgaga    97020
ttacaagcgt gagccatcgc gcctggctaa aaaatacttg attgctaaaa aatgctaaca    97080
atcacctgag ccttcaggga gtcacgatca ttttactgct gtagtcttgc ctcagtgttg    97140
atggctgctg actgatagag tgatgttgct gagggttgga atggctgtgt cagtttctta    97200
aaataacaat gaagtttgct gcattgattg actcttcctg tcatgaacga tttctctgta    97260
gcgtgtgatg ctgtttgata gcattttatg cagagtagaa cttctttcaa aactggaggc    97320
aatcctttca aatcctgccg ctggtttatc aattaagtgt atgcagtatt ctaaattgtt    97380
taactttgtc tcaggaaact actttccttg ctcattcaga agaaacaaca ccttatccat    97440
tcaagtttta ttatgagatt gcaacagttt agtcacattg tcaaactcca gttctaattc    97500
tagttctctt gctatttcta cgcgcctgca gtgacttccg ccactgaatt ttttttttt     97560 ttgagatgga gtctggctct gtctcccagg ctggagtgca gtggcacgat ctcagtcagc    97620
tcactgcaac ttgcgcctgc cgggttcaag tgattcttct gcctcagcct cctgagtagc    97680
cctccactga agtcttgaac ccctcaaagt catccacgag ggttggaatc aacttcttcc    97740
aaactcctgt tgatgttgat attttgacct ccttctgtga aacacagata ttcttaatgg    97800
tatctggagt gcagttatcc ttctcaaaag gttttcaatt tactttgccc agatccatca    97860
gaggattcac tatgtatata tataaaacag ctaatgtatt tctaaaacaa gactggaaag    97920
tagaaatgac ccttgattaa tgggctgcag aatgggtatt gtattattag gcatgaaaac    97980
aacatgaatc tccatgtaca tctccatcag agctcttggg tgaccaggtt cgttgtcatt    98040
gagcaatgag taatatttga aaggaatctt tcattctgag cagtaggtct caacagtggg    98100
cttaaaatgt ctagtaaagt cttgcaataa atggatgtgc tgccatctag gctctgttat    98160
tccatttgta gagcacaggg agagtatatt tagcctaatt cttaagagct ctacagtttt    98220
tggaatggta aatgagcact gttctaccta aagtcaacag cagcatcagc ccctaacaag    98280
```

```
agagtcagcc tgtcctttag tttggaaggc aggtattgac ttcacctgtc cagctagaag    98340
agtcatggat ggcatcttcc agcagggggc tgtttcatct acagtgaaaa tctgttgttt    98400
agtgtagcca ccttcgtcag tgatcttagt tagctagacc ttttaggtaa cttgctgcag    98460
cttctgcatc agcatttgct gctttaccttt gtacttatat gttatcaaga cagcttcttt    98520
ttttaagccc gtgaaccaac ctctgctagc ttccagcttt tcttctgaag ctttctcacc    98580
tctctcagcc ttcatagaat tgaagtgagt tagggcctg ctctggataa agctttggtc     98640
taaggaaatg ttatggttga tttgaccttt tattcagatc actcaaaact ttttccatat    98700
caacaataag gctatttcac tttcttatca tttatgtgtt cactggagta gcacttttaa    98760
tttccttcaa gaacttttct tttgcatttc tagcttttga tttaaagtga gactcttcct    98820
ttttgcctga atgcttagag gccattttag gattattaat tggcctaatt ttaatattgt    98880
tttgtcttag gggatagaga ggcctaagga gagggacaaa gatgggggaa tggctggttg    98940
gtgtagtagt cagaatacac aacatttttg ccgtcttcca tgggtgcggt ttgtggcacc    99000
ccaaaacaat tacagtagta acatgaaaga tcactgatca ttgatcatca taatagatac    99060
aataataatg aaaaagtttg aaatactgca agaattacca aaatgtgata cagagacatg    99120
aagttaccac atgcttttga aaaaattgtg ctgatagact tgctcaacat aggattgcca    99180
caaacttcca atttttaaaa aaatatacta tttgtgaagt gcagtaaact gcagtccagt    99240
aaaatgaggt atgcctgtaa aacaaacccg cagaaaaaaa atcgtctact cagaagagca    99300
ctgacaagta tcattgaatt attatatcta caacttgcta atcaagctaa tgtagtgtga    99360
gttgtagata caaccatttt aatgcagggg ttcctgagat ctgaaaatta ttttaagtgt    99420
gcctccagtg tagaaagatt gagaaaggtt gaaagtgaag atcaataatg ggatgaactg    99480
gaaatatgcc tacctgataa tacaaagcaa tgagagaaac atagtatcac ttccgtcata    99540
ttcctgcctg cgatgcataa tgtgaatcca aaattagaca aaccaaaatt aagggccgtt    99600
atacaaaatg aatggcttat aatctttcaa agttgttaaa ggaatgaaaa taagaaaagg    99660
atcaaggaag tatttcagat acaaaactca aatgggttct gaggaataga cagtctgata    99720
tgtcagtgcc attttcctta ctttaacatt tatattgtga ttatgaagaa gtatgtcctt    99780
tttataagaa atgcatactt acgtgtttgg taggggatgg tgcatcatgt tggaaacccc    99840
tcccctcccc tcccctcccc tcccctcccc tccccaggcc tctcgttagt agtttccaaa    99900
ccttttgcat gctgaaccca ttgctcaaat gaaggcagaa tattaaacat gtaaaggaag    99960
agcttgtgtg tggggggggg ggagcggggg gaaaggaggt tgggggaaca gagaattagg   100020 aaccctgag tgactacaga acttctgaaa accactgttc tgtaggataa aatctaaact    100080
ctgaagcaca ttatacaaac ctctatctat acacatcagt ttgtctgaaa ttgtatattt   100140
ctcaacaata ttgatctatt tgtatttcaa tatgttgtat gctctcatat gtctgtatct   100200
ttgcaaatga tattttcttc tctttaacga tttttgtctt accctgctgg taaggaagtc   100260
accttccctc tcccttctgt atatccttgt caaggaacta tggaaattga atggcatagg   100320
tcttgataca agaacctctc ttttctcttt ataaaaagt cagtaaatag tggtggaaca    100380
ttcaggagaa agttggggac atagagacta agaaggcaat gcagtattat taggacaggg   100440
ggtaaactaa ggcatagagg acagatttga tgaacatatt atctttttta tatacattat   100500
aagaagtaga aggctagaaa agtgaacatg cttgctattg cacgtctcac tttccaattt   100560
catgaagaaa gcaaaaacta cttctacttt attacttctt tttgatgtta attggtacca   100620
catagcaagt ttgcattata gtactgagct ttaaaatgca aggatatact catgtatata   100680
```

```
cacagacaat aaataatagg ttctttttcca cattcaggaa gtgaaactca gctgtccgta   100740
cgacacttac tgtccatata taggcatccc tcagtatctg caggggattg gttccaggac   100800
cctcacacca aaatctaggt atactagtcc tgcagaacca acatatatgc aaagttggtc   100860
ctctgtatac ttgggtttct atatcccatt aatgtggaga atactttga tatgtggata    100920
tggagagctg actgtattta ttgaaaaaaa atccacgtat aagtgcacct gtgctgttca   100980
aactcatgtt gtttgaggga caactgtatt ctgttacttc ctatagtttc taaaagcatt   101040
aaccaacaaa tacatgtaag atgcgtggaa taatttttcc atttcctaga aaatagtcaa   101100
tcattttttt ttcagattgt gaactagaaa gcatagtgaa tatagatttt taaacatgaa   101160
aatgtaagtg tccattttaa attgttatgg atatttctgt ttgctgaagt tcaagactga   101220
agactactgg aaaaaatcct gtgactgaga gcacatagat tccttctttt taggtagagc   101280
gcaacagtca ccatgacttc agtgtttgca tatggaagct aaaatctgtc tgagaaaggg   101340
caaacaatca caggagtcat tgatttattt atttgttcat ttttaatgca aattttaatt   101400
gagtgaaaaa gtggtggaaa aaacagttga ctaaagaaga tatgagaagg gttaatacat   101460
gaagaagtcc tcaataatat tagccaccat ggagatgcag attaaaacca caatgccata   101520
ctactttcca tccacaagaa tagctaaaat taaagaagt cagtcaccac tgaatgttgg    101580
tgaaaatagg aagcagctga aactctctta catggctggt ggaagtgtaa aatggtacca   101640
ttcctgtgga aaactaattg acagtttctt agaaaaaaca ctcaccctat gagcaagcac   101700
tcctagttat ttacccagga gaatgtcca caaataggct ggcacaagaa tgcttatagc    101760
agctttattc agaatgacca aaactgaaa acaactcccc aacattcatc aagagaagtg    101820
ataaataaat tgaggtatat tcatacaata gaaagtacac agggacagaa aagaatggat   101880
ttctgataca tgcgacaaca cgaatatcaa aaacagtatg ctgaattaag gaaaaagaca   101940
acaaagtaa tgcagcatga gtcatataaa catcatataa aaatgatgtt tcaaaatcca    102000
caaaactaat ctgcactgat ggaacagtag ttatctaaat gtgctaagga gtgattagaa   102060
tgggaatggg acatgagaaa agagggaact ttatggagtg atgaaaatat tcaatacctt   102120
tttcttttg agacagtgtc tcgctctgtt tcccaggctg gagtgcagtg tcgcgatctc    102180
gtctcactgc aacctgtgcc tcccaggttc aagtgattct cctgcctcag cctctttagt   102240
agctgggact gcaggcttgt gccgccatac ccggctaatt ttttttttgt gttttagta    102300
gagatggggg ttcactatgt tggtcaggct ggtcttgaac tcctgacctc aaatgatcca   102360
cctgccttgg cccccaaag tgctgggatt gcaggcatga gccaccgcac ctggctgaaa    102420
tattctgtgt cttgattaag gtgttgtata tatagatata tatgttttc aaaactcact    102480
gcgctttcta ctttatataa aaagtacctc aattaaatta catattaatt gaaggcaaat   102540
taaaaacatc tctgtctgta actctcctac tgtgagtctg ttccatgttg aagaatgctc   102600
ttgtcttctt ttctttgctc ttcttggttg ggacttccct gttctaatat caggtatgct   102660
cacgttagaa agctaggaca gaggcctaga atactgattt ttttccattt caacaggcaa   102720
ggtgacagtt ttcctagagt tcacaactct tggtattcca agtcagcaca tagttcacgg   102780
tgaaacattc tctaggaggt agagagaatt gtgaccgaag aatatgatag gaccaaataa   102840
gtagctatac tagaaggaag cacatttgag accactaccc taaacagcca atgactacag   102900
aaccagagaa aaccgaatc tgccaaattt cagaaataac tcagcatctt tacagggagc    102960
ctctacacaa tcacaatgag actctgaaga gtagcaagta ctgattcaaa tccttttagc   103020
```

```
tgtggactcc actctgcctc acaatcattt tagaagaggg ttttgagctt tagaataagc 103080
ccaccactgt ataaaactag tgagtctgtt ttttaaggta ggattcccat cttagtaatc 103140
ataattttgg catggcaatt attaaatatg aaccacaagg agaaaaaaat gtcctcttgt 103200
tattactttt taaattaggc atttaatttt catttactac tgcttgatac tctcttctct 103260
gggttcctgg gaggtttcat ttggtaagta ttgttcagta aaaattatgg acaccattg 103320 ttttggactg tgctcctgcc ctaggcccca gtggaccaga tcaaactaaa atgtagtcat 103380
tcatgttaac tgccacataa tcaaatagaa acttccagga agcagacaga tcccaaagca 103440
gaccattttt ttccctgaga acaggagatt ccagtctagc tgaatcccct gtgctttaaa 103500
cccttagaaa aagtaaactg aagtaacctg atattaacaa atcagctttt ttttcctgtt 103560
ctgtttcctt gttcccacct tacaaaaccc actgttgtgc tgttgctcag taggacctct 103620
cattctacct tgcagaatgg gggctgccct gattcatgaa atgcaaataa atgccagtta 103680
gatctgtaac taaactgttg taattttgtc ttttgacaga atgcagttaa aactcaggta 103740
tatccacact gcttttattt cgtctccttc ccatttcaga aactcctgtc tagatttctt 103800
ttcttgctct ctaaggcaaa caattaccac agttagatga atatgcctgg caatcgctat 103860
tgacagatag actctcagaa acactcgttc cattttcctt ttcaaattct tggcaggaag 103920
actgggtgga tatattgaag gaggtactgt ttgattgtac tgcacacagt gtggtttcaa 103980
aaatgtgtat ttgaattgga aaagagaaat atatgtcagg cactggggat acaatactga 104040
ccaaaggtat ataccctgaa tccaaaaata aatataatgt agttgctgta aacatattaa 104100
ttttaaagat tgtcagaaga atatccatct tagttagacc tttgcaagat atatagataa 104160
gaaaatttct gaaagttaca taactaaaat agaaaccagt caaaatgaac ttcattctac 104220 cctggttttct tccctctaat gttcttatct gtcaatactg tgactgaaaa agccaaacct 104280
accaccacca ccaccactga caaaatccaa aaaactacag atatctacaa cattaattct 104340
aacaccaagt aacattataa cccacttaaa actgttcttt tttctttctt tttttagtac 104400
agacagaact ttttttttttt taatggtaag aaatatcatg attttcttat aaagaccttc 104460
tgtatgtaca aataaagcta tactatcata gtggataaat cagtaaacaa tatcttatgt 104520
aatctgtaat ttttcacaca agaaatttaa aaagttttttc aggttataga acagtatttc 104580
tggacacacc taacaaggca gtagctgaca ttctcaaact tcaaaacacc ctcactttca 104640
atacaaataa tgctgtgttg tacatttaac ctaaaactaa gagaaagcat tgttggttgg 104700
ccacaacttg aatttcttat tacaatgagg actgcttcag gattttacca ctaaactcag 104760
ccgttcagag aactaggaag atagtaacca tggtcactgt tcttcaaaag cactgatttc 104820
agatttgttg aagggatatt tcttagatct tcaagtttct gaaaaggttt ccttcattct 104880
ggttttctgg atttccttgt cattctgaag ttattcctct tgcacaggca aaattagagt 104940
actcattcaa taacaacaac aacaacaaca acaaagccat aaaatatgcc ttcttttttc 105000
tacaacacca atttagctac tcaagataca gaactaaaat attagcagaa atcttgtag 105060 gtatgaagcc agttatgtat tcacattagt aaagatgatt ccactgcatt catttaatca 105120
gcaaacattt acagaatgcc tactacatac caacaatata ttagtgactg catattcatt 105180
taatcccgaa ctctgaaatc attattcctg gtttacaaaa taggaaacag gcttggatta 105240
aggttgcttg cccaaagatt tatagttagt aagattcact accaagtttg aaactcagat 105300
atgtctgagc caaaatttct gctccttcca ctaagccaag ctgtcttcca gcatggcttc 105360
cagcatactt agtatcttgc tgtatcaaga gaaaacaagg tacaggtgac agtgacgtga 105420
```

```
tgccattatg actatctctt tttatataaa aagacccttg ttgagataac tacaactctc 105480
tctttctcag acctcctaca cattgctttt ccttcaatca tcagggtcat gagccttctc 105540
ccctctcctc ccccgccgcc ccccaccacc caacttcccc ctaacaaagt aaaagaaatc 105600
aaatgagatt tgattaaagt gttttgtcta gactgcttca ggactaaagg gtcttggtaa 105660
tttgtaccag cacctcactt cttccccacg cccaaaaact cacgtacaca gtttgattgt 105720
tcttgctttc taaagtgttc tcttttttt gagatggagt ttcgctcttg ttgcccatgc 105780
tggagtgcaa tgacccgatc tcggctcaac acaacctccg cctcccaggt tcaagtgatt 105840
ctcctgcctc ggcctcccaa gtagctggga ttataggcat gtgtcaccat gcccagctaa 105900 ttttttgtatt tttagtagag acggagtttc tccatgttgg ttaggctggt ctcaaactcc 105960
ctacctcagg tgatccaccc gccttggcct cccaaagtgc tgggattaca ggcatgagcc 106020
cggccaaagt gttctgaaag ctatgtgtga atctgttaag tacaatctat acttacattt 106080
gattataaat atttttgacga tctgaattgg taagatttta ggcaaaacaa caaaatcaaa 106140
tcccgtggac tctgacccaa agaatatatt cagctttgtt tgaatatatt tcatcttgct 106200
tccttaccaa ttctcaacac aactccagaa taactgttat taactcttat tgaatcttat 106260
tttgtactaa gccttgttaa atgttttacc tatgaattgt gatttcattg ttacagcaaa 106320
cctatgatat agatgctata taacagatga agaaatgagg ttcagaacct gtgctacgct 106380
gcctcgcagg cacaatccat ctgataaaag tagtcccttg aatctctctt tctgaattcc 106440
agtcccagga cagtggaaat acacagtatt gtggtcaaag ataaaccatt cttggctcca 106500
ggtgagctaa tggttttaga taagaataaa gaatatttat tagaaataaa aaattttgta 106560
agtataaaat tagactagga aaagctcccc ggttgaattt tatatttata aaatccttta 106620
ctgaagttga aatcttctcc ttgaaaattc tgcttggtat ggcctctctg tttgcctcac 106680
aagtgaaatt taatcctaat gttaccttat ttccaagca taaccacacc agtaggctgc 106740
tttgtcatga gtttagtatg gtgtcagtag aaacgagacc agcagtcatt agggttacct 106800
aattcaaatc ttgactcatt tgggtactt cctacaagat tagaataatt atcttccaaa 106860
ccaaaaacat acccaaggtt ccatgggaaa gggtgtagct tcaactcttt ttaggtggca 106920
agaaaatcat tctctaacct ctcaaaggtc aggaataggg tcgatggtcc ttaaaatttg 106980
gtctggggac cactggttgc tgaaccttt gcaggaggtc tgaaaggtca gacctgtttt 107040
cacaatacat gttaagaagt taatggcttt tttgttgtca ttcttttcca agtgtatttg 107100
attatacaac ttgggatgat gttcctctga tagttaatgc aattatactt atgttttaaa 107160
agtttgttag ttttgatttc taatacagta agtctcaaca gatagaactc acataacaaa 107220
acacttttgg gagtccttca taattttttaa gagtgtaaag gaggttctaa gaccaaaagg 107280
tgtggaaact gctcttctag gtttcagaat tatgaagcat acaaagactc ttcatctgga 107340 aggggtttaga ggtaattta tctaatcccc ttattttaca ggtttagaaa ctgattctag 107400
acatttaagt tcccagacta atgtcacaga agctaatgaa ttgcagaggt taattggaag 107460
cctggtctta acactcccag gttatcttaa tgagttcatg aggatggcat atggataatg 107520
cacttcaaag ggtgttgtaa gtattaacta agttaataca ggtcaaatgc atatattagc 107580
actcaatgca cggccattga tcaataaatg ctagtggttc tgatcagtga gaatctaacc 107640
tctgcttaaa tacctttagt catcagcagc ttccactccc tgagtaacat gttgcatttc 107700
ttgatcaatt atattttac agaattcttc ctttactgaa gttgaaatcg tctccttgaa 107760
```

```
atttctactt ggtatggcct ctctgtttgc tacacaaata aatttaatcc taattttatc  107820
tagcttattt tccaagcata accacaccaa tttcattaaa tgattcctca tgtggcatga  107880
ctttaaactc cgtcaccatc ctatttgttt ttctcaaaga gctccagttg actgctcctg  107940
tgaaattgtc catctattaa tgtaaatgtt ttttctaatt ttacagagct ccccgttgta  108000
ttgtgtacag tgttaaaata gttttctgag atttcttgac tctgttttcc caagtttctt  108060
gtggcccttc tctttccttc gtctctattc tgtgcggttt ttatttcact cccacagttt  108120
ctcattgctg tgaggccctg ttatggaatg agagccctgg ttttgaaagt tcacagaggc  108180
tagacttctc ttgtccctgt agtcctggct gagggcccac tacacttgtc tgttatccga  108240
gtgggcaaac gacctacccg ttttcatctg ctgggcggcc ggttatttgg ggggatcccc  108300
ctgttacagg tctgatctct gttgcttcct ttgggaggcc gaggcgggcg gatcaccagg  108360
tcaggagttt gagaccagcc tgaccaatat ggtgacactc ctgtctctac taaaaatgca  108420
aaaactagct gggcatggtg acgtgcgcct gtagtcccag ctactctgga ggctgaggca  108480
gaagaatcgc ttgaacccgg gaggcggagg ctacagtgag tcgagattgt gccactgcac  108540
tccagcctgg gcaacagagc gagactgttt aaaaaaaaaa aaaaaagtt tgtagccatt  108600
atctctggaa atatttactc ttcctcattc ttctgcttat ctcttctctgg aactccaact  108660
agatatatac tagaccttg attctatttt tccacacctc ttaacctgtc tagcttattt  108720
agtcatacat ctctcaagct gcattcttcc ttggagcttt atctgtagga attctttgag  108780
ccttgattga gtttatattg cttcagagaa aactaaggtt tgcttcagct agttgcccag  108840
gaacattacc acctggttac cacttttaat taaggtcact gcttgaggat ttcagagcga  108900
cacagagccc tgtatgaggg cctgtttatg gttataaatt cttggggtgt aggcaggggt  108960
ggggatcctg cttctttacc tggagctaaa actgagacag aaaaatccct gactgtccat  109020
ttttgtgtgg tgggtttatt ttctgttcac cctgaacaat gataggtgtt caccttgtag  109080
agctccccgc tttatgtggg ggtttcctat tagagaacta tcatatgtgg cctgttggct  109140
tattttcttg ccttcagcac ctgtgccagt acataagtta gaaacccaag gtttccaggt  109200
ttcgaaaaac tctcagggca aaagttcgtt ttagcctatg cttagctccc agggtccttt  109260
gtacttggcc atatggattt cttttttttt ttttcttcat gtcaacactg tggttatatt  109320
tatctgtcta acctactctt ttaatttttg ttttatctgg tattttaatt gtttcatttg  109380
agaaagtttt tcatagtatc tgtttggtag ttggccattc tactaggagt ttaggagtta  109440
tacttaactc cttccaggga gatgttggaa gattttact aaaaatacaa tatttaaggt  109500
gggtattgaa gtactatcag aggggacctg gggtggagta tgaaaacaaa acaaaacctt  109560
acaaacggga ataattaaga gttaggatat gtgagatgtt tggttttgct gggcttaaaa  109620
tagaattgtg gggtatggaa ttgctgcaaa tgaggaagat ggactcagag atgaggctca  109680
agagaggcca catgcaactt ttgagagtct ttgtgtgtca cagtaaggaa gatgaacttg  109740
tgaaatcacc aaagggtgga atatataagg aggaagctga cactgtcata tctatgcctt  109800
aggatgttta ttttggcagc agtgaaaaca aatcaggtag acaagagtgg agcattgctc  109860
ttcaaaattt agtcattgac tggcagtaat ggcatcatct gggagcttgt tagaaatgca  109920
gaatctcggg tcctatttca gatttaccaa ctcagaatct gcattttaac aagactccta  109980
agtgttttcat atgcatagtc agttgatgtc tcaaccagtg acctgcagag ccagtgatct  110040
gcaaagcaag tgaacgttag ctttatttta aatttcaaga aagaagtctt aatttgccta  110100
gagtacatat catttgatgt tcacagtgtc actttatttg cctaataact agctgactct  110160
```

```
agatccttag cagcattaga tttagtattt gaggttttga ccctatgtac ctttgataag  110220
tagtgatttg taacttatga attaaatttg aattccttaa catgttgcta gttacaaaac  110280
tctagtgtct ctagcagact attaagaaat tgagcaggtt tcgttctcca ttcactgtta  110340
acacatgcgg taactcacca ggcgcttaaa acaagtgggc tgtggtgcag ggtacttctt  110400
gtttagtgac agaaatgaaa agatctaaga atatgatggt tttaaataaa tatgataaga  110460
gatgaagaga gttttaagta atagaactat tctaagtttt ggatgtttgg tttagtgtct  110520
ctagctatat ttctgtttaa tgtcaaggca taatatattc gaaccatttt atttattaaa  110580
tttaataaac attgattgtc ctattagtca aagtttcaga aaaatgcaaa aagtcttgtt  110640
ctcaaaggaa tgctccctgg accatgcaca tcaaagtcgt gggtggctgc ttgtggggt  110700 agaaaatatt aaaaatgcag aaactgggcc ctactgccga atcccaatgt acattttaaa  110760
ataagcagct tcctggccag gtacggtggc tttcacctgt aatcccagta ttttgggagg  110820
ctgaggcagg aggatcactt gaactcagga gttcaagcct gggcaacata gtgggacccc  110880
catctctgca aaaatggaa aaaagtaaa agcatctccc aaggaattct gccagcagga  110940
aagttgtgtt ttcccccctc aaatctggaa accataattg ttcactttt gaccttttac  111000 tggaatacag catactctga gaaagtaac aacactcaaa taaaaaata gaacattcta  111060 ttccagaacc tcctctagtg actccttcta gaaagcagtc tagcaccca ccctccaaa  111120 cacaaacata accaccatag tgactttaa caccatagat tagttttcc ttttttgaac  111180 tctttaaagt ggaataatac aatttatact ctgtctgttt tgtgttgttt ttgcttagca  111240
ttatgtctgt aaaatttgtc tatattgtta gctgcagttt gtcattctca ttctcattgc  111300
tgtgtggttc tctgttgttt aaagtacca gtggtaaaat tatcatttat gtggtttatc  111360
tctgatggac attagaggta tggtggtacc actgataggc accaaaatca agtttaataa  111420
ccactgttgt atattatttg ggaaaatgtg tactcttgac atgtttggca aatttttatt  111480
tctccaatct aaaatttaga aaattataat tttaaaatta tcaataaaaa tttacaaagt  111540
ttttactgtc aaatattatc taatagctca actagctcat gctagagtaa tacagccatg  111600
taatacagca ttaccaactt ttctaagtgg tctatagcac tgaggaatta aatagcaaat  111660
aagggaagca tttcttcatg aaatcatttc ttttaataaa ttaaaagaa atgagagtat  111720 tagaatacca ccattttgcc accttcagtg tattaatgga tggaggcaat gaatatcaac  111780
agctgctaaa atcataagaa ggaaaccaga tgctagatga cacataatga agtaacacat  111840
tattagacaa aggaacaaac caagttcaat aaagcctctg gatccagctt ccaatttgcc  111900
acaaataaag agaccagatg aatatgctga attgcattat gtgtaaataa tcagtcaaat  111960
ctacactacg aaaagtcaga tcaaacataa attttaagaa aaagaaaaga atggaaaata  112020
aacctgtaga ttaaaagaga ctgaatagaa gtagcaactc ttcttaaaaa tggtcaagat  112080
taaataatag ttatctaggg aggcttactt agctgataaa gtgataaata caggatgtaa  112140
ttaagaataa tttaaaagaa gtgagttact tagaggaagg gaaggggcta tgactgaatc  112200
agcacttgga ggagcttctg ggctcgctgg caaattgctg tgtggtggtc acaagaatgt  112260
attctcttaa tatgctaagg tataaagttt ttgtatagtt ttctgtatct gtattttatt  112320
ttactctaaa ggaagtagtt ttttaaaaaa gattatagat ttgctaatct aatataaact  112380
cccctagagc ttcatcagta atagtctagt gtcatctgga ttatcttcag caatcatttt  112440
cattctaaat tgtcatagtg tcatctcaaa gcagaaagag acagagagtt tgacaaagtg  112500
```

```
tcttaaaatg cctgatgtct gtcttaatga ttctaataga aactcttcag tacaatactc 112560
agacttactg cgcttacaac tacataatgg cttataaatt tgggaaactc aacagatttg 112620
ggaatacaac acatatcttg aagccagtta atttacttt  tacatacctc ttcactattc 112680
cactaccagt gtgcaactgg taattcagtt gaattcataa agaattcact gagttttct  112740 gaatttcttc tgatttcaag aggctagaag aactcagatt ataaagcatc aggttatcac 112800
ttttactata taggcacacc atggtttatt gcactttgct tctgattttt ttttaaaca  112860 aattgaaggg ttggagcaat cctgtgttga gcaagtctct tggtgccatt ttccagcagc 112920
tcactgtgtg tctctgtgtc ccattttggt aattctggca atatttcaat cttttcatt  112980 attattatac ctattatggt tatctatgat cagcgatctc ttttatgtta ctatcataat 113040
tgtttgggga tgccatgaac cacacccata gaagaataaa agatggcaaa cttaataaat 113100
gttgtatgta ttctgaccac tccaccaacc agctgttccc atctctcttt tctcaggcct 113160
ttttattccc tgagacacaa cattgaaatt ttgccaatta ataacctac  agtggcttct 113220 aagtgttcaa gtgaaaagaa gagttgcatg tctctcattt taaatcaaaa gctagaaatg 113280
attagtgaag aaggcatgtt gaaagcagag acagggcaaa agctaggcct tttgtgccaa 113340
acatccaagt tgtgagtaca gaggaaaagt tcctttcttt ttttcacttt ttcgtatgtt 113400
taaaaagtag agacagggtc tcgctatgtt gatcaggctg ttcttgaact cctgacctca 113460
agcagtcctc ccacctcggc ttcctcaagt gctgggatta taagcatgag ccactacacc 113520
cagctgaaaa gttcttgaag gaaattaaaa gtgctactct ggtgaacaca tgaattataa 113580
gcaaaacagc cttattgctg atatggagaa agttttagtg tctggataga agatcaaatc 113640
aaccataaca ttcccttaaa caaaagccta atccagagca aggcccgaac ttacttcaat 113700
tctatgaagg gtaagagggg aggaagcttc agaagaaaag ttggaagcta gcagtttggt 113760
tcctgaggtt taaggaaata agctgtctcg ataacatgta agtacaaggt aaagtagcaa 113820
gtgctgatgg agaagctgct gcagcatgtt atctagaatg tctagctaag atcactgatg 113880
aaggtggcta ccctaaaaga ttttcaatgt agatgaaaca gcactctatt ggaagatgcc 113940
atctaagact tttctagctg gataggggaa gtcagtacct ggcttcaaaa catcaaagga 114000
caggctgact ctcttgttag gggctaatgc tgctggtgac ctcaagtgga agccagtgct 114060
cattggtcat tccgaaaatc acagggtcct aagaattatg ctaaatctac tctgcccatg 114120
ctctgtaaat ggaacagagc ctggatgaca gcacagtttg ctagatatgt taagcccact 114180
cttgagtcct actgctctca gtgaaagatt cctttcaaaa tattactgct cactgacaat 114240
gcacctggta acccaagaac tctgatggag atgtacaagg agattcctat tttttcatgc 114300
ttgataaaca taataacatc tattgtgtag cccgtggatc aaggagtcat ttctactttc 114360 aagtttatt  atttaaaaaa tatatttctt aaggctgtag ctgccgcagt gattcctgtg 114420
atgaatctgg gcaaagtaaa ccaaaaacct tctgggaagg attcaccatt ctaagtacca 114480
ttgagaacat tcgtgattta tgggagggg  tcaaaatatc agcattaata agagttggga 114540
agaaattgat tctaccccca tgggcaactt tgaagggctc aagactacag tggaggaagt 114600
cactgcagtt gtggtagaaa tagcaagaga agtagaagta gaacttgaca cagcgtgaca 114660
attgctgaaa tctcaagata aaatttgaat ggctgaggtg ttgcttttta ttgatgagca 114720
aagaaagctg tttcttgaga tggaacctac tcctagtgaa gaggctttga aaattgttga 114780
aatatcaaca aaggacttag aatattacat aaaattagtt gacaaattga taaagcagcg 114840
gtggtttggg aggattgcct ccaatcttga aagaagatct acagttaggt aaaatgctgt 114900
```

```
cacatagcct agtgtctttc atgaaaggaa gagtcaattg atgtggctaa ctttattgtt  114960
gtcttatttt aagaaattgc cacagccata ctgattagtc agcagccatc aatatcaaga  115020
taagaccccc caccggcaaa aaaattggac tcactgaagt ctcagttgat cattagcatt  115080
tttttaagca gtatagtcct tttaaattaa ggtatgtaca tttttttttac acataatgct  115140
attacacact taatagtagt gtaaatataa cttttattgc actgggaaac caaacatttt  115200
tttgtgacct gctgtattgc aatattacct ttattgcagt ggtctggaat tgaacctgca  115260
gttttctgag gtgtaagtat tggtgaaatc attaacctcc tcctctgtgt gtgtggtttc  115320
ttcaactcac aaaggatagc agccccagtg aaagtcgtta cagaaggcag ataaactcca  115380
ttttttttaa gactttgcca ctctgtgtgt gtgtgtgtgt gtgtgtgtgt gtgtgtgtgt  115440
gtgtgtttac cttatcctag tgggccttac cacacatttc tattatgtga gatccaaaag  115500
tgatgtggta tacacaagag taattttcac cccattctta aaactgaaaa tgatgtttaa  115560
atcactttt cttgggggaa aattcaaccc cgtggtaatt aagcttcact tttcctgaaa  115620
ttaatctttt tataaatttt ataaacttat aagaaatgta atacattttg cttaagtaac  115680
tagcataagc caaaatggca cttcattttt cttaggctca gcagatttaa tttaataaag  115740
attataaatt gattttaatt aatgatgttt acgaaatgaa aattaattga cagtgttgaa  115800
tagtaaagct gctaaaacca taagccaaag caatatgaat aaaagtataa tttagacaca  115860
attttaaacc agattttgaa aaactttact cggtgatatg gtcaggctca attgtatgcc  115920
tgctagttag attacttctt gtataggctg atatatgcat aaaattatta tttttgaatt  115980
ttaaataaaa ttatatttat ctctttaatg tgaatttacc tctttaatgt aaaaattata  116040
tttgtttttt gtccttgttt cttactgcac atatcaattc caggtcaagc atgagataag  116100
caaatcatgt taatttcatt ttcaactgaa ataagactat ttctgagctt attcttgttt  116160
gctgaataaa aaaagattgt tcatatgtgc gagaaattgc tgcagcataa tgttcactgt  116220
ttttctgtga gtagcaggat aatcttttct tcatagaaat ctacatcttg tctgggaaag  116280
attagtaaaa ctcatcttta atgtatgata aaactgcaga tctttttcct ttttctcaa  116340
gtcaaatttt cacagtcaga acattcagaa acaggatccc ttttccagtt ctacacttgt  116400
gttcaagtga aggaaaatct gttcagtttt ttttctgcag ctcctccagg tgatttccag  116460
taagacttga gacttgctga tatccttcct cactctcaag cccaaacagc aatagaaaca  116520
tttcaagatt ttcttttgta acatgttttt caaaagctca ttttccttttt acatccaaga  116580
atgttgtcct ttgaaataaa gaaaacccaa ccatttctt cacaccttac agagactgaa  116640
aaataagtac tacgtaggct agtttctaca gccattaatg tttaagtatt caacagactg  116700
tagcctactg ttttctttaa aggacccatt tcagttcaaa taccctattg agaagttttc  116760
cactgctaag tggattttgt gtgtgtgtgt gtgtgtgtgt gtgtgtgtgt gtggtaagag  116820
ctgttcttta aatgagtgaa atgacctttg tttaatgaag ttaaccattt tataacatct  116880
ttcagatgtt aaaacatttt gccccaagag cttttgatat cagtactctt aacacagatg  116940
tttttttgtgt tagtttgggt cttctgagac acagatgtca agacaagatt tgatgcgcag  117000
ggaatctccc acccccaccct actaccctcc tattgtcctt tggagcaatc cccattctag  117060
tacttctgcc ctgcttggta gcttgctggg agaagcccag aggcagcaag gccaggggtg  117120
gttgccatgg attccaaggt gcgatagatg gaggctgtca agcagttctg ttcctcatag  117180
caggttaggt tgaggggata tctgagtagg gtaccactgt ggccactgca ccctcctctt  117240
```

```
cagcctttga catctttccc tcatgtggac actctttact gtgttacgca cccacaggga    117300
tgttgtcact gtgttctgcc tttgacctac gggggcttct ttactatatg gattattcct    117360
catgcttctt agagtcaagc tttgccacct tgcccccttg ttggtctgcc tctgttcctc    117420
cccgccgcca tccctcacta cagaaaggct cttttcattc tgctttgact cccaaatttt    117480
ggactacctg cctgccacat acatacctaa cttgcttggc tccatctaat agcttttga    117540 ctaaattttt gaggaaaaga aggaagaaga gccatctggg tttcttacat ctgcaactag    117600
ctagaatatg attccattca ctgaaataga gaaaataata ggaggctcta agaacaaatt    117660
tgggccttac gtatgtgtgc atgttgtggg gaaatagaag tttggatgtt aaaataatga    117720
atttggtgtg actttgggac accttcttga aattaatagg ctcagtagag gagtctgact    117780
ggagataata gtatggggag tcattagctt ctgtgtgata gttggaaccc tgactttcaa    117840
cgaaacaaca aaggagggag gagctagcga tggagcacag taacagtgct gcctgaggga    117900
tgcactgagg aatgtaccaa ggaaaattaa gggacaggag agagttgtaa agagagctag    117960
tgaccaacag aatataaaga tacaaaaatg gcaaagagt ctttgagatt taacaaccag    118020
tttaaaattt agttattatg gagtaagccc atatcacaca ggtggtggcg tatcacacag    118080
ggattaaatt tagccaaaac aaaatatgta ttataattca aataacaaaa aatatatatt    118140
gtcatgtgga ctgaggaata gtcttttgca tcctttccag taaagatata tatgattgac    118200
tagtgaagtc tatttaaatt attcagtgta catccataaa actttatcaa ttactttctg    118260
tgtatatgat gacacttgcc agtattgccc attttgtgct gattttgtta gtgtacatta    118320
ctaaggagct tttcatcaaa ttttgcagtc cctgaaagat tttcatcttt aaagttacaa    118380
atgtgatttc tcagctgcag tatagaatat atggaaccag aaatactcaa aaaataattg    118440
ttttcgaagt attaatcttt ttagtcacag ttgttttttt acatcctgtg ctgaaaataa    118500
caagaaattt gatacagagg gaaaaatgat ttattatgac ttagtagaca atttacaaat    118560
gtgtgttaag atattaggat atatgtccta ccagtttcaa aagtactaca agtgacttgt    118620
tcaatacaga gtacaacttt aaaaaatgta tttaaagtaa ttgacgttgt gtttgtgacc    118680
tggctcgaag ttcttttttg gtgaagagca tgcttagtac atgattgtct ttaaaaagat    118740
ctgataatta tttactcagt aaatgttttg agtgccttat gagtcaggca ttttgtggg    118800 tgctggagat aatagtgatg aaaaacaaaa gtcccttttc cttatagaac ttaaattcta    118860
gtgtgggaag gcagatagta cagaaataaa ttgatggatg gatagatgga taggtaggta    118920
tttgctatat agcaggtact attttttgctt ttatatagtg ctgtggaaat gagtaaagtc    118980
aggacaaagg aaaagagaag gtgatgctgg ggggtattat tttaagttgg atggttaggg    119040
aaagtatcat tgaataggg acatttgaac agagtcctct atgaaggaag taaaagaaat    119100
aaaaagagga atagctagca caaagactct gaggttgcag cacactttac ccctcaagaa    119160
agaacggtga cagaaagggt ggaacaaagt gagagagtag taaaatatga gttcacagtg    119220 gtgggatgt atgtagatga tagaaggacc caacaggcaa ccataaaaga cattggcttt    119280
tactctgagt gaaatgggaa gctcttagtg ggtgttgagc agtggagtaa taagataaaa    119340
cttatttcat catgcatttc aggtacttac tcctaatcat agtaattaat aaattattaa    119400
tttggggtat agaaagttca tatatgaagt ggagggtgtt ggctctttta agaattcagt    119460
gaaaatccta aacttcttgc agaaagtgat tccaagcttt gagttattct tcctgatgat    119520
cagtacagtt ggtttacttt cttgttatct ttgtcctaaa gcttcttaaa tcactttgta    119580
gctcaagcct aatggattat acctgcccat gtaaattctg aaaatgttaa tgttgcctag    119640
```

```
tgattcagag gctttagtaa tttacttaaa ctacttcttg ttttattggt ataaactgta   119700
ttcctcagtg tctactatga tttcaaagtt agtatttgcc ttggaatttt tctttgaagc   119760
tggcaactct agttcaatat aagacaggct ctcagagctc cacttattta acaactgtat   119820
ctatgcccac ttttattcct ctaagcattc ctagaataag catttcaaat ggttttgaat   119880
tatcaaaggt cttttgaaa aacaaggtta ttgagaaaat gtttaaaaag ttcatgagaa    119940
agttgtctaa aatacacccc cctcccccaa ggtaggcctg aaatgccact aaatcaacaa   120000
aggatagtca ctaaaagtta ccctgtattt tctaggactt ggggaaagtc atggagtagc   120060
tgtgcttttct ctaagtaacc tattttaaat ttttttgaag agcaaaatta ttatacctct  120120
ttttcatcca gaatggagct gactgtaggc atcttttttaa agtacccata ggtcaggacc  120180
tctctggact ttccactacc ttgaaagaca ctgccagaag aatgttgttc cccacactta   120240
aaaaaggaaa agtaatgttc ttttctccag ccattatttt atgcaaagtc caactttatt   120300
ttatctgagc tatctgaact ttcaatttat ttgaaacatt tattgattaa tatctataat   120360
ggagctttta atttctctga tcatttatcc tttgttaggt tagcagaact gtaacaacac   120420
agtcactttc acagccacga atgatacttt tatagtcatt tgtggacata tactgtgcag   120480
agtatcacaa agtttgagcc acctgacaaa cttatttcca gttgagatct gcagggtgat   120540
gctctgcctt cttgttgcag ctctcatacc atgaacaagt gtcattttca tggtccatga   120600
ggaaaaagca ttttcctcat tttggtgctt tttgttagtg attgtgcagt ttagaatggc   120660
ccccaaacat agcctgaagt tctgtttaat gttccgaagt gcaggaaggc tgtaatttgc   120720
cttaaagata aactaatgtg tgttaaagaa acttaattca ggcattagtt ataatgctgt   120780
tgaccatgag ttcgatgcta atgaatcaat gtatattaaa gatatattta ggcagaaaca   120840
cgcataaaaa aggttatgca ttgatcagtt ggcaacagtg ttgtgaccag aggcttgtga   120900
gaactgtatt tcccctagga gcaatggctc agtatttgtt aattcagtgg ttgcagcaat   120960
tttatagaac acaattactg tgaatgggaa tcaactgtat ttgattaacg gtggtgattt   121020
atagggactt tagataccag aaatgtttca taattcccct tctctgaaat cactgtttta   121080
atatgtttaa atgcatgcat gcagagttgt gatgttaaac ataattttac tgtgggttct   121140
ggtcaaaaaa gatgaaatgt cattggttaa cttgaaagag acattattct aaacattatc   121200
ctccagaaaa ttgacatgta caggaagcat attgaatgct cagcaaataa tttgttttag   121260
agtaataatc tttgagtatt gtagtgattc gagttttgga aaagaaggca gtatcagtgt   121320
tagagaataa tattctttca ggattttatg tagttactttt aaggtgcatg aaaggagact   121380
cagttgggtg ttaaattctt gtccctgctt tacttgaaac tagtaatctt gagaaattta   121440
ctaaatcatt ttgagccttg attaccttgc ctgcaaagtg aggaacattt tcaatttaaa   121500
attctatttc ttttattagt attcttcctg accttgaatc atttctattc ccatcatgtc   121560
cagttgccaa gaaaaccatg caacttaatg ttgtttgtta gccatcagat tttattttac   121620
tgaactcaag ttcagtcaca tcagttaccg ataaaataat aagttctata ttaatatttg   121680
atatatcttg acatttttgta ttatggtagg aagaaataaa agaccttcct caaatttag    121740
gatatgggct tctgtttgtt gatgtttgtg ttttatgata cactgttgta aatcatacta   121800
aaggttttct ctgaaaaaga ctagaattga caatacttca tttgttagca gtttcaagtt   121860
ttagatcacg ggtgcataat ttcttgtgtg tgcacaacat gttggcattt tatctgactt   121920
caaagatgtc catatagata ccagcaaagg ataaaatgta agaatgaata tcatgaaaag   121980
```

-continued

```
atgctgtatc agataaaatt ctagagccta ggttaaaaaa cataaaggca aacatgcttg   122040
atatataaaa attgagaaat atgataaaaa gaagtaagtt taaagcatca gtaataccac   122100
tgcctaagat gcagtttatt ttgaaatgtt gtcttctagt cttcatacag tttaaaaatc   122160
atactataat cacaatttcc agcattttcc ccttagcata atatattata acatccatgt   122220 tttaaaaat attttatgaa cgtcatgttt agggattaca ccatatatat cccatctcat   122280
agattccttt atattgaaca tttggatttt tatttacatt tttatttaca tttattttta   122340
tctttatttt ttgctttcgt ggataaactg cagtgagcat cctctgtata aatttttttt   122400
ttctgtttta ggattacttc cttaggatag attgccagaa gtggagttac tgggtcagag   122460
ggtatgaact tatgaactt tttttaaat aaatttttg ttcattttct gtccagtcat   122520
ttgtaaaaaa attaaaataa taatgattat aattgttacc tgctagaaaa ctgtgtctga   122580
aggcaagatt ctgtgatcag aaaagtttgg gaaatatccca gggtaaaaag ccttttaatc   122640
tgatttacct cagcatttcc caaattaact gaacactgaa aattttttt gatacacttc   122700 ttaaattt gtggaagttt tatataggat atagtctatg aactactgat gtaaaattaa   122760
aattgtttta tttgcttgaa atattatgtt ttattggtca aaggaattaa actataaatc   122820
ttcatgctaa aaattattaa aagggattag tgttgtttac tatggttttt gtgcatgtct   122880
ttataaagtc ttataacttt taaaattgaa atgttctata ttgtttacta aagaacattt   122940
taatgccttg gtggcatcaa tacttttttg caatcattaa tgatatttag aaagtagaca   123000
tataacatga aagtagaaca taatatagat tgtacaaatc ttgttttta ccctatttc   123060 ccctgcag                                                          123068
```

<210> SEQ ID NO 5
<211> LENGTH: 23
<212> TYPE: RNA
<213> ORGANISM: Homo sapiens

<400> SEQUENCE: 5

```
uuauugcuua agaauacgcg uag                                              23
```

<210> SEQ ID NO 6
<211> LENGTH: 102
<212> TYPE: RNA
<213> ORGANISM: Homo sapiens

<400> SEQUENCE: 6

```
gguccucuga cucucuucgg ugacggguau ucuuggguggg auaauacgga uuacguuguu   60
auugcuuaag aauacgcgua gucgaggaga guaccagcgg ca                        102
```

<210> SEQ ID NO 7
<211> LENGTH: 2469
<212> TYPE: DNA
<213> ORGANISM: Homo sapiens

<400> SEQUENCE: 7

```
agatggtgta gatcagatcg atttgattgc attagatgat ttttccctt ccccactcct      60 ttctggaagc tcgcatcagc tgaaggctat cgcctgggac tcctcggaag catgagcaag    120
ccgccaccac gcgaaggcac tggggcacag ccagcgcgag gcgccgaggt cccttcccaa    180
ggcttgttaa cactgtaacc cggcactcgg agagaagaag cagctcacac tgcccagagc    240
ctacctcact gcacatcaga tgactccctg gcttctacac acagttggag ttccgcttga    300
aacctggatt tagaggggtt ctctggccgc catggcactc aatcatacca cctagagtgg    360
```

```
actggccgag accagactgg gtaccaagca gagaagtgca gaggaaagca ctgggagagc    420
accagaattg gaaatagagc ggccatttgg atttgggcag gaagcagccg agcacagctt    480
tggatccttc tttagggaaa tcgagttatg gatttatggt cccggtcaag ctcagcccat    540
ccccaggcag gggcgggctc agcgagcagc aagagttctg gtggcggcgg cggcggcagt    600
agcagcggca gcggtagcag cggcagcggt agcagcggca gcggcagctt ggtcctctga    660
ctctcttcgg tgacgggtat tcttgggtgg ataatacgga ttacgttgtt attgcttaag    720
aatacgcgta gtcgaggaga gtaccagcgg caggggggca gcggccgccc tccccagccc    780
accagctggc cactaaacgc ccgtggttgc caaggcatcc aaagcctctg ggatgtgttc    840
tgactgtaaa aactctgatg ttgtgaaaaa agcttacgct ttgcctccac tcaaaccaga    900
tggtgtttcg ctcttattgc ccaggctgga gtgcaatgac gtgatcttga ctcaccacag    960
cctctgcatc caggattcaa gctattcccc tgcctcagcc tcccaaaatg ctgggattat   1020
aggcgtgagc caccacgcct ggccagcatt cccaattttt aaaaatgaat gattggcaca   1080
aatcttagaa agccatttc tgtagatttg aaagcaatgc tatttacatt gttactactt   1140
tcttgttaaa tcttgcatgt ctgcagtatg tgttgtaata gaaacctaag attatgatct   1200
gctgtattca tatttgaaga agaaaatttc agactgtata atcaactagt tgatgattca   1260
tatttgcttg tacaaagtta aaagtgtaac ttgccagaaa agaaggaagc ctgaaaagta   1320
ttctaaatac attaataaga agggttctac atgaattaat ttttgttttg ccatctacag   1380
agttcctgcc acattctagg cacttcatat ttgctgcaac attattcag acattgacag    1440
aacaagagaa acgaagttaa attttaagta ccatggattg aaattaaatt tagggaagat   1500
atttatagt atgaattgtt catctgtatt taacaaggta ttcatttatt ttgggcgatt    1560
taaggaaggt cctttctgga aacaggatta caaacatatg gacctattta gtcaatttca   1620
accttgtgat tttgaatctg acaggttctc agctgctttt attaaataac ggattttctt   1680
aataattact gtactcaaac ttagcaaaaa gctctattta tagcccagtt ttttagtcac   1740
acactattgt gtcttgtcaa attgaaacca tatactacat tctttactta ttaagatggt   1800
cttttctttgt aataattttg gagtaaatag tttacttatc taaacctctg atttctgatt   1860
taacagattt ttgaagcatt tattttcctt accatacata aaaattgtca gttgaggaca   1920
aggaaggatt aacctggact acggtgaata attgttcagg ttgcttactg tgtaactcca   1980
gaggagcatt cacatggtac aatttgcaga tttaagtatt tattacaacc attttctggc   2040
agataacagt ggaacaccct gttctgttaa aattagttta ttatgacaaa ttgcctacag   2100
atggacataa actgtcttga ggaagggcac ctgctttgga ctgaatcgtg tccccccaaa   2160
atcaaatgtt gaagcctaat ctctaatatg atggtatttg gagatggggc ctttgggaga   2220
taactaggtt tagatgaggt caagagtgtg gggccttcct gattagtacc ctgaaaagag   2280
aaaacaccag agagcttgcc ctctctccct cttaccccac aggcacacaa agaggtcatg   2340
tgagtacaca gtgagataac aaccacctat gagaaaacag aagaggcttc agagtgaaat   2400
ctactttgct ggtactgtaa tcttggacat tattctctag aactgtgaga taataaattt   2460
atcttattt                                                          2469

<210> SEQ ID NO 8
<211> LENGTH: 21
<212> TYPE: RNA
<213> ORGANISM: Homo sapiens
```

-continued

```
<400> SEQUENCE: 8
agaccuggcc cagaccucag c                                              21

<210> SEQ ID NO 9
<211> LENGTH: 75
<212> TYPE: RNA
<213> ORGANISM: Homo sapiens

<400> SEQUENCE: 9 gugggggagcc ugguuagacc uggcccagac cucagcuaca caagcugaug gacugaguca   60
ggggccacac ucucc                                                     75

<210> SEQ ID NO 10
<211> LENGTH: 1037
<212> TYPE: DNA
<213> ORGANISM: Homo sapiens

<400> SEQUENCE: 10
ctgtgggaca gaggaacagg cagagatcag agggcaggct caggttggga ggagtgggga   60
gcctggttag acctggccca gacctcagct acacaagctg atggactgag tcaggggcca  120
cactctccct cctctggtga tgtgacctca gctggtttct tcccactcgg ccatgggttt  180
cccatcctgg agtgggatta agaatccttg tcctggccct gtgcagtggc cacacctgta  240
atcccgacac tttgggaagc ttagatggga gaatccctag gggccaggag ttcaatacca  300
gcctgggcaa catagggaga ccctgtctct acaaaaaaaa tttttaacaa ttagcccggt  360
gtggtggtgt gagcctgtag tcctagctac ttagaggcag atgtgggagg atcacttgag  420
cccagtttga ggctagtcca ggcaacatgg caagatccta tctctaccaa aaatatatat  480
aaacgtgcgt gtgtgtgtgt gtgtgtgtgt gtgtataaat atataaaaga atccttgtcc  540
tgcctgtctc atgggcagct tggaggaaac actgtttttt tgtttttttt tttttgaga   600 tggagttttg ctcttgttgc ccaggctgga gtgcaatggc acgatctcag ctcaactgca  660
acctccacct cctgggttta agcgattttc ctgcctcatc ctcccgagta gctgagatta  720
caggtgccca ccaccacacc tggctaattt tttgcatttt tagtagagat ggggtttcac  780
catgttggcc aggatggtct cgaactcctg acctcaggtg agccacccca ctcggcctcc  840
cgaagtgctg ggattacagg catgagccac tgcgcccagc ctggaaacac tattgacaag  900
tgaggaggcc tagtccattg agtatcagct agggctacaa acttccaaat cggtgaatca  960
ggtccagaga gggacaagtg ccccagggtt acacaatcat ttgctgaagc agaggttgct 1020
gccatctttg gcctcac                                                1037

<210> SEQ ID NO 11
<211> LENGTH: 23
<212> TYPE: RNA
<213> ORGANISM: Homo sapiens

<400> SEQUENCE: 11
ggcagguucu cacccucucu agg                                            23

<210> SEQ ID NO 12
<211> LENGTH: 98
<212> TYPE: RNA
<213> ORGANISM: Homo sapiens

<400> SEQUENCE: 12
guguaguaga gcuaggagga gagggccug gagaagcgug gaccggcccg ggugggcguucc   60
```

```
ggcagguucu caccucucu aggccccauu cuccucug                                98
```

<210> SEQ ID NO 13
<211> LENGTH: 1412
<212> TYPE: DNA
<213> ORGANISM: Homo sapiens

<400> SEQUENCE: 13

```
gtgagggcgg gcgcgggcca gcggccggga agccctaggc caggcccctc ccctgaagga      60
agggcatagg gcgggtcctg cctcaggggg cttgcgagga ccggccaggt tcatctcatg     120
cagcatcaga caaccactat gcagagggat tttatgacgt ttttgaaaaa ttgggaagac     180
aatggtttga cacccacttt gcaggtttag acgaagagat gcgtactgtc aagctggcct     240
gttctctgtc cccgaggcag tcagccagca ccctgcagcc ccgcgccaac cccacactct     300
gctaagccct cgctttgggg cttgagggag acagaccctg cttcgaagga ccctggaggg     360
agggttctgt cctgcttggg ccaggatgcc cagcccctgg gaccccgggg ggacatgct     420
ggaagaagtg gcgaaggaca cgtggccccg tcagcccag acgccgcacg gctgtcctct      480
ccaacaatat cctggtgctg agtgatgact caggcgactc cagcatcagt gattttgttg     540
aagagggcag ctgccagcct cccgacctgc ctgccgggcc ccagctgccc tgcccccaac     600
cccaacccac cccactccac cccctaggcc caggacacat ggccctgtag cgatcccctg     660
gcacgcagac atgggtttta tgtggggagg acaggctgg gttggcctct gtccccaccc      720
tgagtcctga gcacagaagt aatacggcag ctgtggtaat atctacccag taccctgtgc     780
ctcctcacac ccacgtgacc agccaggcag ggttcaaagc cagcagccaa ggcaggctgg     840
gttggaggta gtgccaggcg taacctgcat tctttccaga ccctacccaa ccctggggcc     900
agtggtggct caagtgagag tgagctccag ctctgagtgg gcatggcagg gctggaccct     960
aaaactggac tccggcagcc ggcaggaccc ctgggacact ccaggcctca gtttccccat    1020
caattcccac ctcctgggga gccgagagtg atagtgtagt agagctagga ggagagggtc    1080
ctggagaagc gtggaccggt ccgggtgggt tccggcaggt tctcaccctc tctaggcccc    1140
attctcctct gcactgtaac atttgaggcc cacgcacaca gtccctcccc aggtctcagg    1200
gttgggcaca gagtagggcc ctgggcaggg atgggggtg gcagtgtctc caacgcccct    1260
tccagcctgg actgtgagcc atccaagtgt tggcaaagga ccctgtgctg gatgcccccg    1320
cccggcacac cccactgacc ctccccctgc ccccacccgg cacaccctgc tcaccctgct    1380
cacccctgccc ctgccctgc ccctgcctgc ag                                  1412
```

<210> SEQ ID NO 14
<211> LENGTH: 6
<212> TYPE: PRT
<213> ORGANISM: Artificial Sequence
<220> FEATURE:
<223> OTHER INFORMATION: synthetic peptide

<400> SEQUENCE: 14

Gly Gly Gly Gly Asp Asp
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic peptide

<400> SEQUENCE: 15

Gly Gly Gly Gly Gly Gly Asp Asp
1               5

<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Gly Gly Gly Gly Gly Gly Gly Gly Asp Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Gly Gly Gly Gly Gly Gly Gly Gly Gly Gly Asp Asp
1               5                   10

<210> SEQ ID NO 18
<211> LENGTH: 7
<212> TYPE: PRT
<213> ORGANISM: Artificial Sequence
<220> FEATURE:
<223> OTHER INFORMATION: synthetic peptide

<400> SEQUENCE: 18

Ala Ala Ala Ala Ala Ala Asp
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic peptide

<400> SEQUENCE: 19

Ala Ala Ala Ala Ala Ala Asp Asp
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ala Ala Ala Ala Ala Ala Lys
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic peptide

```
<400> SEQUENCE: 21

Ala Ala Ala Ala Ala Ala Lys Lys
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic peptide

<400> SEQUENCE: 22

Val Val Val Val Val Val Asp
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Val Val Val Val Val Val Asp Asp
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic peptide

<400> SEQUENCE: 24

Val Val Val Val Val Val Lys
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic peptide

<400> SEQUENCE: 25

Val Val Val Val Val Val Lys Lys
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic peptide

<400> SEQUENCE: 26

Leu Leu Leu Leu Leu Leu Asp
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27
```

Leu Leu Leu Leu Leu Leu Asp Asp
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28

Leu Leu Leu Leu Leu Leu Lys
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Leu Leu Leu Leu Leu Leu Lys Lys
1               5

<210> SEQ ID NO 30
<211> LENGTH: 19
<212> TYPE: RNA
<213> ORGANISM: Artificial Sequence
<220> FEATURE:
<223> OTHER INFORMATION: synthetic RNA

<400> SEQUENCE: 30
uucuccgaac gugucacgu                                              19

<210> SEQ ID NO 31
<211> LENGTH: 19
<212> TYPE: RNA
<213> ORGANISM: Artificial Sequence
<220> FEATURE:
<223> OTHER INFORMATION: synthetic RNA

<400> SEQUENCE: 31
acgucacacg uucggagaa                                              19

<210> SEQ ID NO 32
<211> LENGTH: 22
<212> TYPE: RNA
<213> ORGANISM: Artificial Sequence
<220> FEATURE:
<223> OTHER INFORMATION: synthetic RNA

<400> SEQUENCE: 32
uaccugaauu cccaaaagcu uu                                          22

THERAPEUTIC PHARMACEUTICAL COMPOSITION FOR CANCER INCLUDING MIRNA

TECHNICAL FIELD

The present invention relates to a pharmaceutical composition for cancer therapy comprising a transcription or processing product of a gene encoding a particular miRNA.

BACKGROUND ART

MicroRNA (hereinafter miRNA) is a functional nucleic acid that is encoded on the genome and ultimately becomes a minuscule RNA of about 20-25 bases long through a multistep production process. miRNA is classified as a functional ncRNA (non-coding RNA), and it is being elucidated that it plays an important role in various biological phenomena (such as regulation of gene expression etc.). Various miRNAs that has come to be well-known thus far including human miRNA are registered in the miRBase (see http://www.mirbase.org/).

miRNA is indicated to be associated with the onset and progression of e.g. cancer, cardiovascular disease, neurodegenerative disease, psychiatric disease, chronic inflammatory disease, and the like. Particularly in recent years, it has been indicated that miRNA is deeply involved in canceration or aging of cells.

For example, Patent Literature 1 describes that miR-22 promotes the aging of cells and suppresses invasion and metastasis of cancer. Moreover, Patent Literature 2 describes that a composition comprising miR-34 may be employed for cancer therapy.

CITATION LIST

[Patent Literature 1] WO2011/078037
[Patent Literature 2] WO2008/137867

SUMMARY OF THE INVENTION

Problems to be Solved by the Invention

The present inventors diligently searched for miRNAs having therapeutic effect against cancer from among a great number of miRNAs.

Means for Solving the Problems

As a result, the present inventors found particular miRNAs that have significantly stronger cancer therapeutic effect than the miRNAs described in prior art, thus arriving at the completion of the present invention.

In other words, the present invention relates to a pharmaceutical composition for cancer therapy comprising a transcription or processing product of a gene encoding a miRNA, characterized in that said miRNA is one or more miRNAs selected from the group consisting of miR-3140, miR-137, miR-631, and miR-657.

One embodiment of the present invention is characterized in that said cancer is a solid cancer.

One embodiment of the present invention is characterized in that said solid cancer is colon cancer, pancreatic cancer, tongue cancer, mesothelioma, uterine sarcoma, osteosarcoma, breast cancer, lung cancer, or head and neck cancer.

One embodiment of the present invention is characterized in that said transcription or processing product of a gene encoding a miRNA is a pri-miRNA, a pre-miRNA, a double-stranded mature-miRNA, a single-strand mature-miRNA expressed from the 5'-end of a pre-miRNA, or a single-strand mature-miRNA expressed from the 3'-end of a pre-miRNA.

One embodiment of the present invention is characterized in that said miRNA is: (i) a mature-miRNA consisting of a sequence represented by SEQ ID NO. 1, SEQ ID NO. 2, SEQ ID NO. 5, SEQ ID NO. 8, or SEQ ID NO. 11; (ii) a miRNA having substitution, addition, and/or deletion of 1-5 bases to a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect; or (iii) a miRNA having 80% or more sequence homology against a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect.

One embodiment of the present invention is characterized in that said miRNA is chemically modified.

One embodiment of the present invention is characterized in that said chemical modification is one or more chemical modifications selected from the group consisting of LNA-tion, BNA-tion, ENA-ation, 2'-OMe modification, phosphorothioation, S-TuD-ation, morpholino modification, peptide addition, glycosylation, aptamer addition, hydrophobic molecule addition, polymer addition, and addition of unmodified DNA.

One embodiment of the present invention is characterized in that said pharmaceutical composition further comprises a nucleic acid transfection agent.

One embodiment of the present invention is characterized in that said transfection agent is a lipid-based transfection agent, a polymer-based transfection agent, a magnetic particle-based transfection agent, an exosome for nucleic acid delivery, or a viral protein for nucleic acid delivery.

One embodiment of the present invention is characterized in that said transfection agent is a transfection agent comprising a peptide represented by amino acid sequences GGGGDD (G4D2), GGGGGGDD (G6D2), GGGGGGGGDD (G8D2), GGGGGGGGGGDD (G10D2), AAAAAAD (A6D), AAAAAADD (A6D2), AAAAAAK (A6K), AAAAAAKK (A6K2), VVVVVVD (V6D), VVVVVVDD (V6D2), VVVVVVK (V6K), VVVVVVKK (V6K2), LLLLLLD (L6D), LLLLLLDD (L6D2), LLLLLLK (L6K), or LLLLLLKK (L6K2).

One embodiment of the present invention is characterized in that the pharmaceutical composition of the present invention is for topical administration.

One embodiment of the present invention is characterized in that the pharmaceutical composition of the present invention is used in combination with other anticancer agents.

One embodiment of the present invention is characterized in that said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

Another embodiment of the present invention relates to the use of a transcription or processing product of a gene encoding a miRNA for manufacturing a pharmaceutical composition for cancer therapy, characterized in that said miRNA is one or more miRNAs selected from the group consisting of miR-3140, miR-137, miR-631, and miR-657.

Another embodiment of the present invention relates to a cancer therapy method comprising a step of applying to a cancer patient a therapeutically effective amount of an anti-cancerous pharmaceutical composition comprising a transcription or processing product of a gene encoding a miRNA, characterized in that said miRNA is one or more miRNAs selected from the group consisting of miR-3140, miR-137, miR-631, and miR-657.

An invention of any combination of one or more characteristics listed above is encompassed by the scope of the present invention.

DESCRIPTION OF EMBODIMENTS

Figure 1:
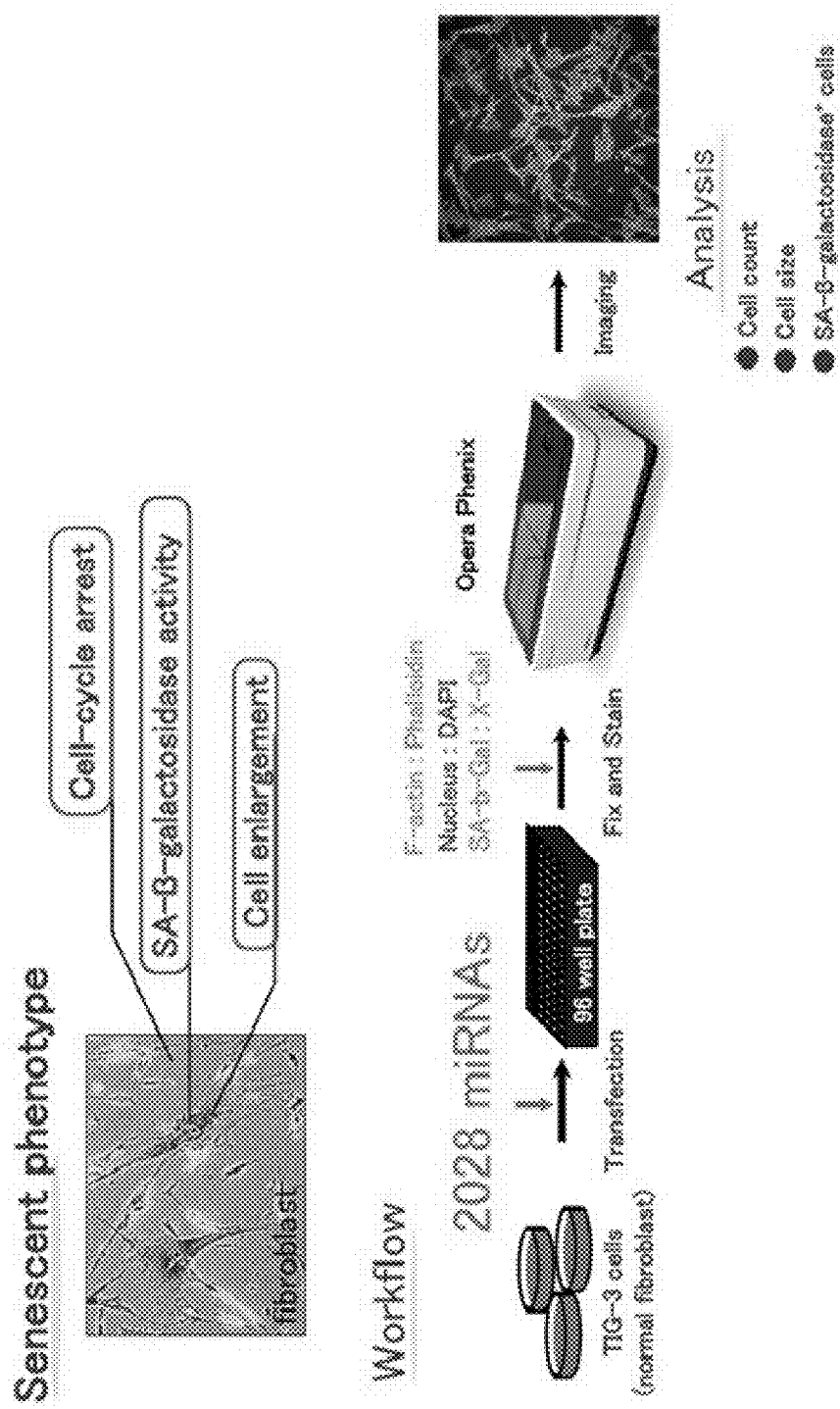
FIG. 1 describes the flow of miRNA screening in the Examples.

The present invention relates to a pharmaceutical composition for cancer therapy comprising a transcription or processing product of a gene encoding a miRNA (microRNA). A general miRNA is biosynthesized via a continuous process. The primary transcription product of a gene encoding a miRNA is called a Primary miRNA transcript (pri-miRNA), and generally has a stem-loop hairpin structure. Pri-miRNA is cleaved by a microprocessor complex, takes a hairpin form by Drosha which is a RNase III-series enzyme, and precursor miRNA (pre-miRNA) which is an intermediate precursor of about 70 bases is produced. The pre-miRNA is then transported from the nucleus to the cytoplasm. In the cytoplasm, it is further cleaved by Dicer which is another RNase III enzyme, and a double-stranded mature miRNA is produced. In general, among the two strands, "-5p" is added to that expressed from the 5'-end of the precursor and "-3p" is added to that expressed from the 3'-end, and are represented as "hsa-miR-21-5p" and "hsa-miR-21-3p". Note that in principle, well-known miRNAs are registered in the miRBase (http://www.mirbase.org/).

Note that only one of the strands in the mature miRNA may exert the desired effect, or each of the stands may exert the desired effect, or the desired effect may be exerted in the double-stranded state. Moreover, the desired effect may also be exerted in pri-miRNA state or pre-miRNA state.

The nucleic acid comprised in the composition of the present invention may be a transcription or processing product of a gene encoding one or more miRNAs selected from the group consisting of miR-3140, miR-137, miR-631, and miR-657, and may also be a variant or a modification that retains the function of the aforementioned nucleic acid.

The sequence of the transcription or processing product of the gene encoding miR-3140 used in one embodiment of the present invention is as follows.

TABLE 1

| Name | Sequence |
| --- | --- |
| Mature-miRNA (miR-3140-5p) | ACCUGAAUUACCAAAAGCUUU (SEQ ID NO. 1) |
| Mature-miRNA (miR-3140-3p) | AGCUUUUGGGAAUUCAGGUAGU (SEQ ID NO. 2) |
| Pre-miRNA | CCUCUUGAGGUACCUGAAUUACCAAAAGCUUUAUG UAUUCUGAAGUUAUUGAAAAUAAGAGCUUUUGGGA AUUCAGGUAGUUCAGGAGUG (SEQ ID NO. 3) |

Note that the sequence of the intron region encoding the pri-miRNA of miR-3140 is shown in SEQ ID NO. 4.

The sequence of the transcription or processing product of the gene encoding miR-137 used in one embodiment of the present invention is as follows.

TABLE 2

| Name | Sequence |
|---|---|
| Mature-miRNA (miR-137-3p) | UUAUUGCUUAAGAAUACGCGUAG (SEQ ID NO. 5) |
| Pre-miRNA | GGUCCUCUGACUCUCUUCGGUGACGGGUAUUCUUG GGUGGAUAAUACGGAUUACGUUGUUAUUGCUUAAG AAUACGCGUAGUCGAGGAGAGUACCAGCGGCA (SEQ ID NO. 6) |

Note that the sequence of the intron region encoding the pri-miRNA of miR-137 is shown in SEQ ID NO. 7.

The sequence of the transcription or processing product of the gene encoding miR-631 used in one embodiment of the present invention is as follows.

TABLE 3

| Name | Sequence |
|---|---|
| Mature-miRNA (miR-631-5p) | AGACCUGGCCCAGACCUCAGC (SEQ ID NO. 8) |
| Pre-miRNA | GUGGGGAGCCUGGUUAGACCUGGCCCAGACCUCAG CUACACAAGCUGAUGGACUGAGUCAGGGGCCACAC UCUCC (SEQ ID NO. 9) |

Note that the sequence of the intron region encoding the pri-miRNA of miR-631 is shown in SEQ ID NO. 10.

The sequence of the transcription or processing product of the gene encoding miR-657 used in one embodiment of the present invention is as follows.

TABLE 4

| Name | Sequence |
|---|---|
| Mature-miRNA (miR-657-3p) | GGCAGGUUCUCACCCUCUCUAGG (SEQ ID NO. 11) |
| Pre-miRNA | GUGUAGUAGAGCUAGGAGGAGAGGGUCCUGGAGAA GCGUGGACCGGUCCGGUGGGUUCCGGCAGGUUCU CACCCUCUCUAGGCCCCAUUCUCCUCUG (SEQ ID NO. 12) |

Note that the sequence of the intron region encoding the pri-miRNA of miR-657 is shown in SEQ ID NO. 13.

The nucleic acid comprised in the composition of the present invention may be e.g. a nucleic acid having substitution, addition, and/or deletion of 1, 2, 3, 4, or 5 bases to a mature-miRNA consisting of a sequence represented by SEQ ID NO. 1, SEQ ID NO. 2, SEQ ID NO. 5, SEQ ID NO. 8, or SEQ ID NO. 11, as well as having the effect of inhibiting cancer cell growth. The substitution of a base to the mature-miRNA may be e.g. a conservative substitution of RNA known in the art.

Moreover, the nucleic acid comprised in the composition of the present invention may be e.g. a nucleic acid having 80% or more (preferably, 85% or more, 90% or more, 95% or more) sequence homology (or sequence identity) to a mature-miRNA consisting of a sequence represented by SEQ ID NO. 1, SEQ ID NO. 2, SEQ ID NO. 5, SEQ ID NO. 8, or SEQ ID NO. 11, as well as having the effect of inhibiting cancer cell growth.

A mature-miRNA consisting of a sequence represented by SEQ ID NO. 1, SEQ ID NO. 2, SEQ ID NO. 5, SEQ ID NO. 8, or SEQ ID NO. 11 can be easily manufactured by a RNA synthesis equipment commonly used in the art, and a nucleic acid having a particular base substituted, added, and/or deleted can similarly be easily manufactured. Moreover, numerous companies accept commissioned synthesis of nucleic acids, and it is also easy to obtain RNA of the desired sequence from such companies. Accordingly, those skilled in the art will be able to investigate the nature and function of a variant or modification of a mature-miRNA consisting of a sequence represented by SEQ ID NO. 1, SEQ ID NO. 2, SEQ ID NO. 5, SEQ ID NO. 8, or SEQ ID NO. 11 by conventional means without excessive burden.

Moreover, the nucleic acid comprised in the composition of the present invention may have received a chemical modification well-known in the art with the purpose of improving the stability or specificity etc. of RNA. Chemical modification that may be employed in the present invention may be e.g. LNA (Locked Nucleic Acid)-tion, BNA (Bridged Nucleic Acid)-tion, ENA (2'-O,4'-C-Ethylene-bridged Nucleic Acids)-tion, 2'-OMe modification, phosphorothioation (S-ation), S-TuD (Synthetic Tough Decoy)-ation, morpholino modification, peptide addition, glycosylation, aptamer addition, hydrophobic molecule addition such as cholesterol, polymer addition such as PEG, or addition of unmodified DNA. These chemical modifications can be performed by a well-known means known in the art.

The present invention can be employed for various cancer therapies, e.g. it can be favorably employed for solid cancer. More preferably, the subject of the present invention may be colon cancer, pancreatic cancer, tongue cancer, mesothelioma, uterine sarcoma, osteosarcoma, breast cancer, lung cancer, or head and neck cancer.

In order to appropriately introduce the present invention to cancer cells, the composition of the present invention may further comprise a nucleic acid transfection agent. Examples of the nucleic acid transfection agent that may be employed for the present invention include a lipid-based transfection agent, a polymer-based transfection agent, a magnetic particle-based transfection agent, an exosome for nucleic acid delivery, or a viral protein for nucleic acid delivery.

An example of the lipid-based transfection agent includes a cationic lipid. With a cationic lipid, nucleic acid-cationic lipid complexes are incorporated into cells via endocytosis and released into the cytoplasm, thus introducing the nucleic acid into cells (lipofection). Specifically, e.g. various commercially available reagents for lipofection may be employed.

An example of the polymer-based transfection agent includes e.g. a cationic polymer. When a cationic polymer comes in contact with a nucleic acid, a nucleic acid-polymer complex is formed, and the complex attaches to the cell membrane via electrostatic interaction and is incorporated into the cell via endocytosis. Specifically, a cationic peptide and a derivative thereof (such as polylysine and polyornithine), a linear or branched-chain synthetic polymer (such as polybrene and polyethyleneimine), a polysaccharide-based introduction molecule (such as cyclodextrin and chitosan), a natural polymer (such as histone and collagen), as well as active and inactive dendrimers, and the like may be employed. Moreover, transfection agents employed in so-called nanoDDS, such as a transfection agent that employs a block copolymer that forms micellar nanoparticles and a transfection agent that employs carbon nanohorns can also be used for the present invention.

An example of the magnetic particle-based transfection agent includes a transfection agent that employs magnetic particles coated with cation molecules. A magnetic particle-based transfection agent carries out transfection by adhering the nucleic acid on the surface of magnetic particles, and then magnetically introducing the aforementioned magnetic particles into cells. Specifically, for example various commercially available magnetic particles for transfection may be employed.

Moreover, nucleic acid transfection agent that employs a generally available exosome or a transfection agent that utilizes viral proteins such as adenovirus can also be used for the present invention.

Further, in the present invention, a transfection agent comprising a peptide represented by amino acid sequences GGGGDD (G4D2) (SEQ ID NO. 14), GGGGGGDD (G6D2) (SEQ ID NO. 15), GGGGGGGGDD (G8D2) (SEQ ID NO. 16), GGGGGGGGGGDD (G10D2) (SEQ ID NO. 17), AAAAAAD (A6D) (SEQ ID NO. 18), AAAAAADD (A6D2) (SEQ ID NO. 19), AAAAAAK (A6K) (SEQ ID NO. 20), AAAAAAKK (A6K2) (SEQ ID NO. 21), VVVVVVD (V6D) (SEQ ID NO. 22), VVVVVVDD (V6D2) (SEQ ID NO. 23), VVVVVVK (V6K) (SEQ ID NO. 24), VVVVVVKK (V6K2) (SEQ ID NO. 25), LLLLLLD (L6D) (SEQ ID NO. 26), LLLLLLDD (L6D2) (SEQ ID NO. 27), LLLLLLK (L6K) (SEQ ID NO. 28), or LLLLLLKK (L6K2) (SEQ ID NO. 29) may be employed, and in particular AAAAAAD (A6D) or AAAAAAK (A6K) can be favorably employed. The effects of these peptides as transfection agents are disclosed in e.g. WO2010/024262.

The pharmaceutical composition for cancer therapy of the present invention can be used in combination with other anticancer agents well-known in the art. Other anticancer agents used in combination are not limited, and e.g. one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation can be employed.

The aspects of combination use of the pharmaceutical composition for cancer therapy of the present invention and the other anticancer agents well-known in the art are not limited, and can be carried out by those skilled in the art (such as a physician) in various aspects according to the type of cancer to be the subject or therapeutic stage and the like. The pharmaceutical composition for cancer therapy of the present invention and the other anticancer agents may be administered to the subject at the same or different times. The pharmaceutical composition for cancer therapy of the present invention and the other anticancer agents may also be prepared as formulations comprising each and administered to a subject. The pharmaceutical composition for cancer therapy of the present invention and the other anticancer agents may also be prepared as a kit that separately comprises each.

An aspect of administering the pharmaceutical composition for cancer therapy of the present invention and the other anticancer agents at the same time may be e.g. an aspect of administering to a subject a formulation comprising the pharmaceutical composition for cancer therapy of the present invention and the other anticancer agents.

In the present invention, an aspect of administering the pharmaceutical composition for cancer therapy of the present invention and the other anticancer agents at different times may be e.g. an aspect of administering each of the pharmaceutical composition for cancer therapy of the present invention and the other anticancer agents with staggered time, and e.g. an aspect of administering the pharmaceutical composition for cancer therapy of the present invention and the other anticancer agents from different administration routes.

The administration route of the pharmaceutical composition for cancer therapy of the present invention is not limited, and may be systemic administration or topical administration. Administration routes can include e.g. oral administration including sublingual administration, parenteral administration such as inhalation administration, direct administration to target tissue by catheter or injection, intravenous administration including infusion, transdermal administration by patches and the like, suppositories, or administration by forced enteral nutrition employing a nasogastric tube, a nasointestinal tube, a gastrostomy tube, or enterostomy tube, and the like.

The dosage form of the pharmaceutical composition for cancer therapy of the present invention may be appropriately determined according to said administration route, and can include, but is not limited to, injections, infusions, tablets, capsules, fine granules, powders, liquids, solutions dissolved in syrups etc., patches, suppositories, and the like.

The subject for administering the pharmaceutical composition of the present invention is not limited, and e.g. the present invention can be employed for mammals (humans, pigs, cows, monkeys, baboons, dogs, cats, rats, mice, and the like). However, when it is unfavorable, humans can be removed from subjects.

The administration method of the pharmaceutical composition of the present invention to a subject (administration route, dosage, administration frequency per day, administration timing, and the like) is not limited, and can be appropriately determined by those skilled in the art (such as a physician) according to the health state of the subject, the extent of disease, the type of agent used in combination, and the like.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, shall not be construed as being limited to the Examples described herein.

EXAMPLES

Experiment 1: Screening of MiRNA with High Cell Aging Inducibility (1) Transfection of all miRNAs into TIG-3 Cells (FIG. 1)

A total of 2028 types of miRNAs (mirVana; Ambion) were transfected into TIG-3 cells (human fibroblasts) with an auto dispenser Bravo (Agilent). Transfection was carried out by the following protocol.

1: To 70 μL of serum free medium (SFM) was added 0.35 μL of RNAiMAX (Invitrogen).
2: The solution from 1 was added to a 96-well plate (μ-plate; ibidi) with Bravo.
3: To 2 was added 0.7 μL of miRNA (Stock Conc. 2 μM) with Bravo, and this was mixed by pipetting.
4: This was incubated at room temperature for 20 minutes.
5: A cell suspension diluted to $3.5 \times 10^4$ cells/mL was dispensed at 70 μL each with Bravo.
6: This was incubated at 37° C. under 5% $CO_2$ condition.

(2-1) Staining of transfected cells

Setting the day of transfection as Day 0, staining was performed five days later in order to evaluate the number of cells and cell size. The protocol therefor is shown below.

1: Washing twice with PBS (-) was carried out.
2: 3.7% formalin solution was added, and this was incubated at room temperature for 10 minutes to fix the cells.
3: Washing twice with PBS (-) was carried out.
4: Staining solution was added, and this was incubated at room temperature for 30 minutes for staining.
5: Washing three times with PBS (-) was carried out.
6: The plate after completion of staining was subjected to full visual field photographing with an automatic photographing equipment Operetta (Perkin Elmer).
7: The photographs taken were subjected to quantitative analysis with an image analysis software Columbus (Perkin Elmer).

TABLE 5

Table 1: Composition of the staining solution

| Reagent name | 1 mL | final Conc. |
| --- | --- | --- |
| PBS(-) | 1 mL | |
| Triton X-100 (NACALAI TESQUE) | 1 μL | 0.1% |
| BSA (Sigma-Aldrich) | 10 mg | 1% |
| Alexa Fluor® 488 Phalloidin (Thermo Fisher Scientific) | 4 μL | 0.8 Unit |
| DAPI (1 mg/mL) (DOJINDO) | 0.1 μL | 0.1 μg/mL |

(2-2) SA-β-galactosidase assay of transfected cells

Setting the day of transfection as Day 0, SA-β-galactosidase assay was performed on Day 7. The operating protocol is shown below.

1: Washing twice with PBS (-) was carried out.
2: 2% formalin solution was added, and this was incubated at room temperature for 5 minutes to fix the cells.
3: Washing twice with PBS (-) was carried out.
4: β-Gal staining solution was prepared at the time of use and added to the wells.
5: This was incubated at 37° C. for 12-16 hours.
6: The plate after completion of staining was photographed with an automatic photographing equipment Opera (Perkin Elmer).

TABLE 6

Table 2: Composition of β-Gal staining solution

| Reagent name | stock conc. | final conc. |
| --- | --- | --- |
| citric acid/Na phosphate buffer *[1] | 0.2M | 40 mM |
| $K_4(Fe(CN)_6)3H_2O$ | 100 mM | 5 mM |
| $K_3(Fe(CN)_6)$ | 100 mM | 5 mM |
| NaCl | 5M | 150 mM |
| $MgCl_2 \cdot 6H_2O$ | 1M | 2 mM |
| $H_2O$ | | |
| X-gal *[2] | 20 mg/mL | 1 mg/mL |

*[1] Prepared so that pH is 6.0.
*[2] X-gal (5-Bromo-4-chloro-3-indolyl-(β)-D-Galactopyranoside: Wako) was prepared at the time of use with N,N-dimethyl formamide.

Figure 2:
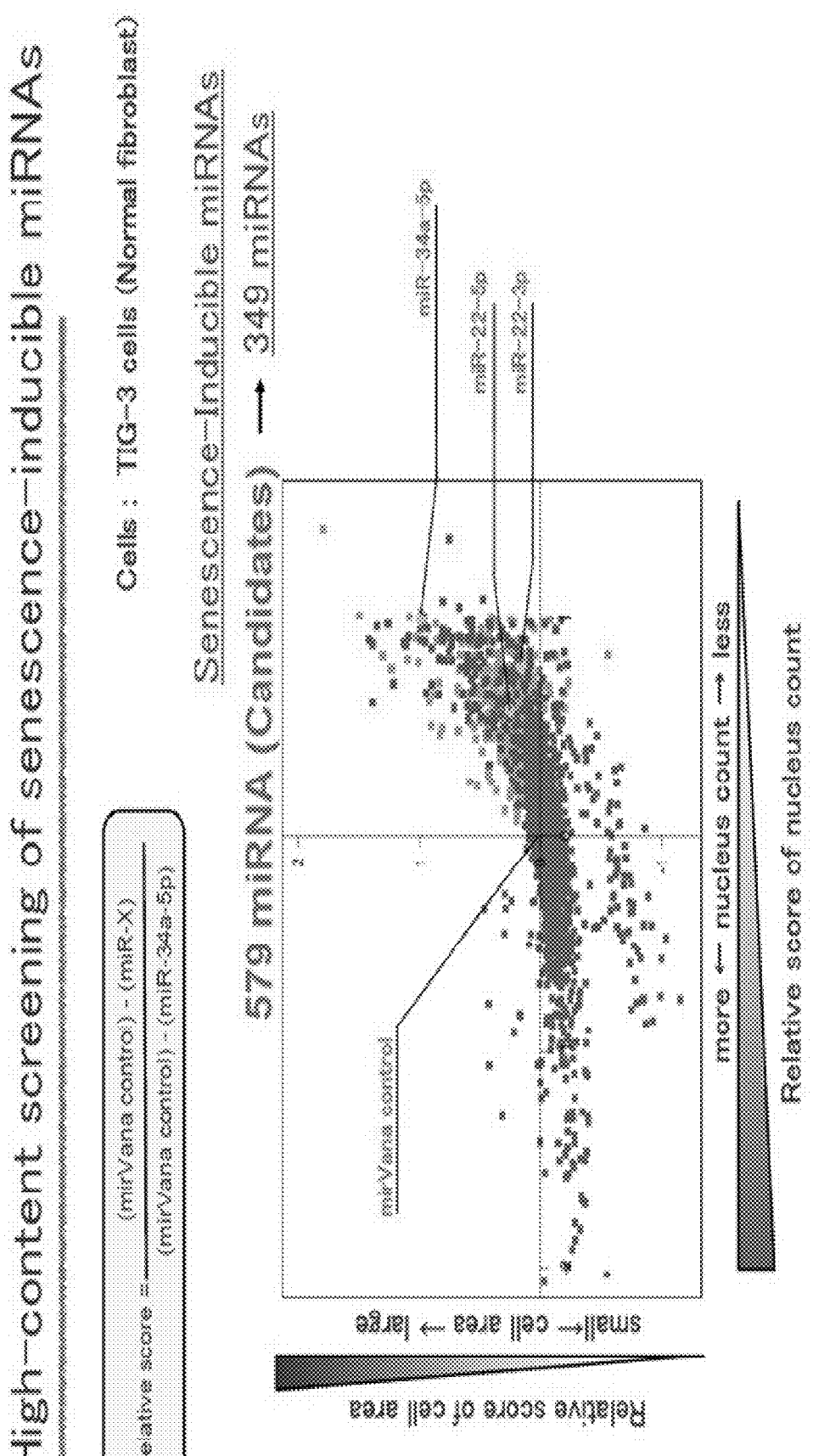
FIG. 2 describes the flow of miRNA screening in the Examples.

(3) Analysis of the screening result (FIG. 2)

Each of the values of the number of cells and cell size obtained were scored with the numeric values of random sequence miRNA which is the negative control and the numeric values of miR-34a-5p which is the positive control. The scoring method is shown below.

Within each plate
1: The value of the positive control was subtracted from the value of the negative control.
2: The value of each miRNA was subtracted from the value of the negative control.
3: The value from 2 was divided by the value from 1 to obtain a score value.
4: A scatter diagram was drawn by taking the score value of the number of cells on the horizontal axis and the score value of the cell size on the vertical axis.
5: 579 types of miRNAs where at least one of the two showed a score value higher than the score values of miR-22-3p and miR-22-5p were identified as aging induction miRNA candidates.
6: Out of the 579 types of candidates, 349 types of miRNAs that induced activation of β-galactosidase which is a cell aging marker were identified as aging induction miRNAs.

Experiment 2: Further screening employing cancer cell strains

The 349 types of aging induction miRNA (mirVana; Ambion) obtained from screening were transfected into various cancer cell strains (large intestine cancer cell strain HCT116 (p53 wildtype and p53 deletion), pancreatic cancer cell strains BxPC-3 and CFPAC-1, and tongue cancer cell strain HSC-4) with an auto dispenser Bravo (Agilent).

Transfection was carried out with the following protocol.

1: To 70 μL of serum free medium (SFM) was added 0.35 μL of RNAiMAX (Invitrogen).
2: The solution from 1 was added to a 96-well plate (μ-plate; ibidi) with Bravo.
3: To 2 was added 0.7 μL of miRNA (Stock Conc. 200 nM) with Bravo, and this was mixed by pipetting.
4: This was incubated at room temperature for 20 minutes.
5: A cell suspension diluted to $3.5 \times 10^4$ cells/mL was dispensed at 70 μL each with Bravo.
6: This was incubated at 37° C. under 5% $CO_2$ condition.

Setting the day of transfection as Day 0, on Day 5 the cell survival rate was evaluated with PrestoBlue (Invitrogen). The operating protocol is shown below.

1. The medium was exchanged to a medium comprising PrestoBlue diluted 20-folds, and this was incubated at 37° C. for 1 hour. 2. The fluorescence value (Ex/Em=560 nm/590 nm) was measured with Enspire (Perkin Elmer).
3. The cell survival rate was determined by setting the fluorescence value obtained from the well with only the reagent as the background.

The above protocol was carried out for each cancer cell strain (large intestine cancer cell strain HCT116 (p53 wild-type and p53 deletion), pancreatic cancer cell strains BxPC-3 and CFPAC-1, and tongue cancer cell strain HSC-4), and the miRNAs that suppress cell proliferation more significantly than miR-34a-5p were sorted.

Figure 3:
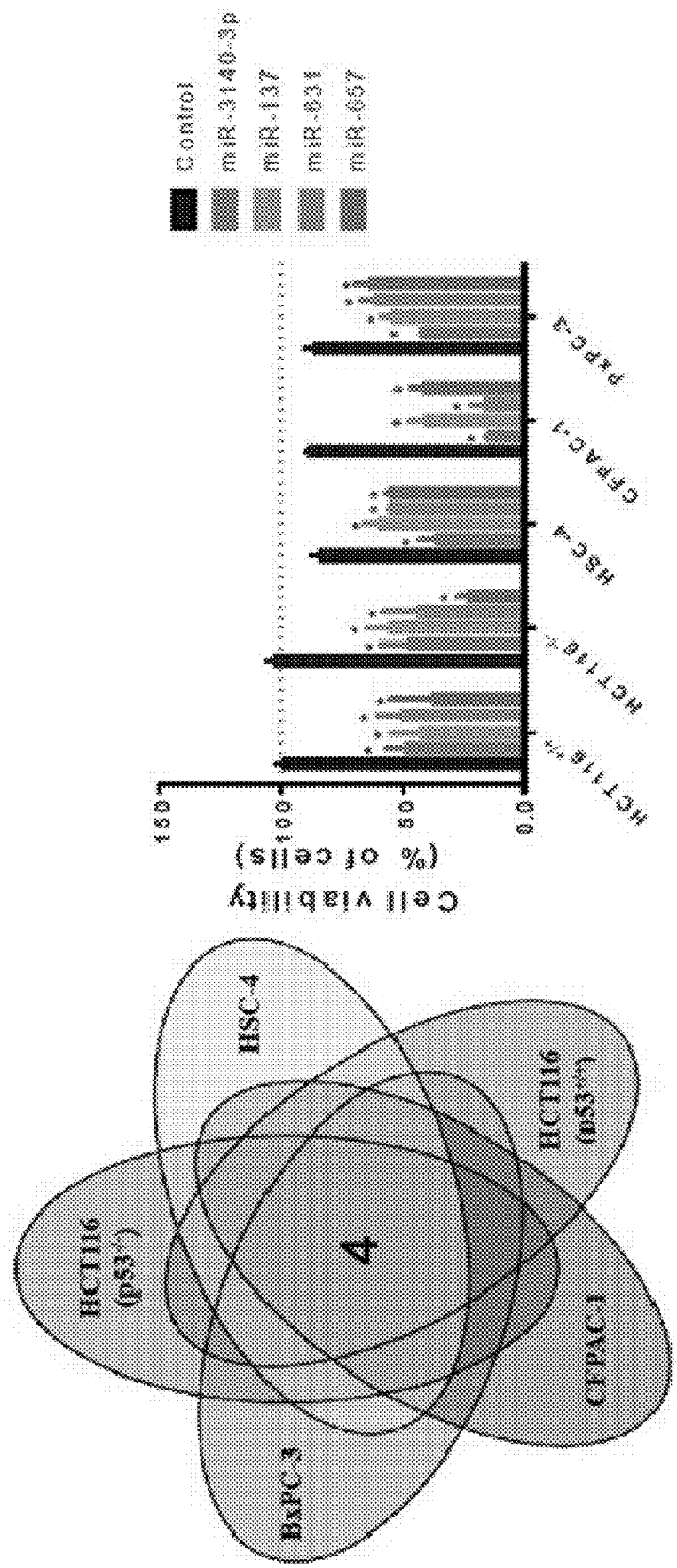
FIG. 3 shows four miRNAs that show growth inhibition effect against numerous types of cancer cells sorted in miRNA screening.

As a result of sorting the miRNAs that suppress cell proliferation more significantly than miR-34-5p commonly in all cell strains, four miRNAs (miR-137-3p, miR-631-5p, miR-657-3p, and miR-3140-3p) were found (FIG. 3).

Figure 4:
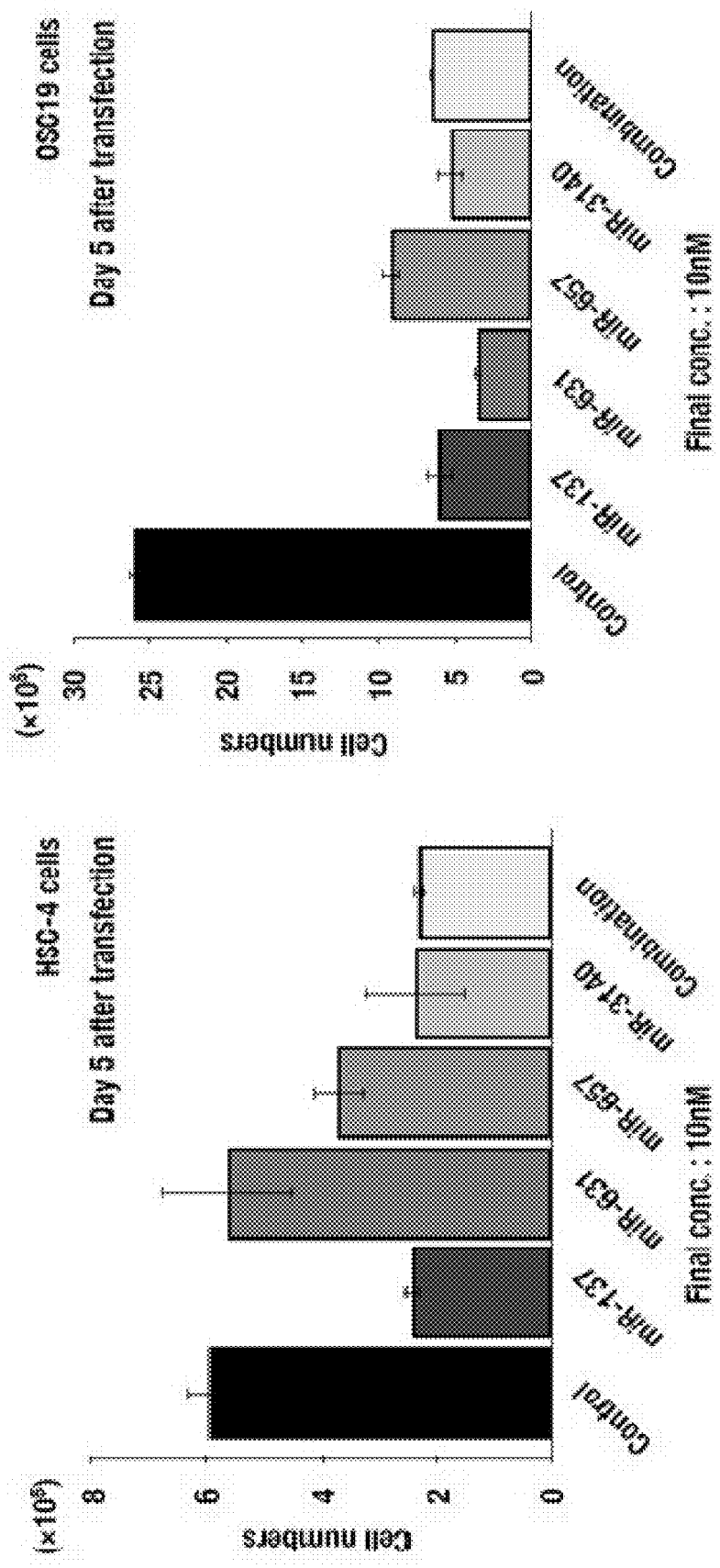
FIG. 4 shows the effect of the miRNA of the present invention on tongue cancer cell strains (HSC-4 cells and OSC19 cells).

Experiment 3. Confirmation of cell growth inhibition effect employing various cancer cell strains (1) Tongue cancer cell strain (HSC-4 and OSC-19) (FIG. 4)

Four miRNAs (miR-137-3p, miR-631-5p, miR-657-3p, and miR-3140-3p) were transfected into tongue cancer cell strains (HSC-4 and OSC-19), and cell proliferation was observed. Transfection was carried out with the following protocol.

1: To a 35 mm dish were added 500 μL of serum free medium (SFM) and 5 μL of RNAiMAX (Invitrogen).

2: To the solution from 1 was added 1 μL each of nucleic acids (Control, miR-137-3p, miR-631-5p, miR-657-3p, miR-3140-3p, and a mixture of equal amounts of the four miRNAs (final concentration 10 nM).

3: This was incubated at room temperature for 20 minutes.

4: A cell suspension diluted to $6.7 \times 10^4$ cells/mL was added to the 35 mm dish at 1.5 mL each.

5: This was incubated at 37° C. under 5% $CO_2$ condition.

6: The cells were counted five days after transfection.

As shown in FIG. 4, the four miRNAs showed cell growth inhibition effect in both tongue cancer cell strains.

Figure 5:
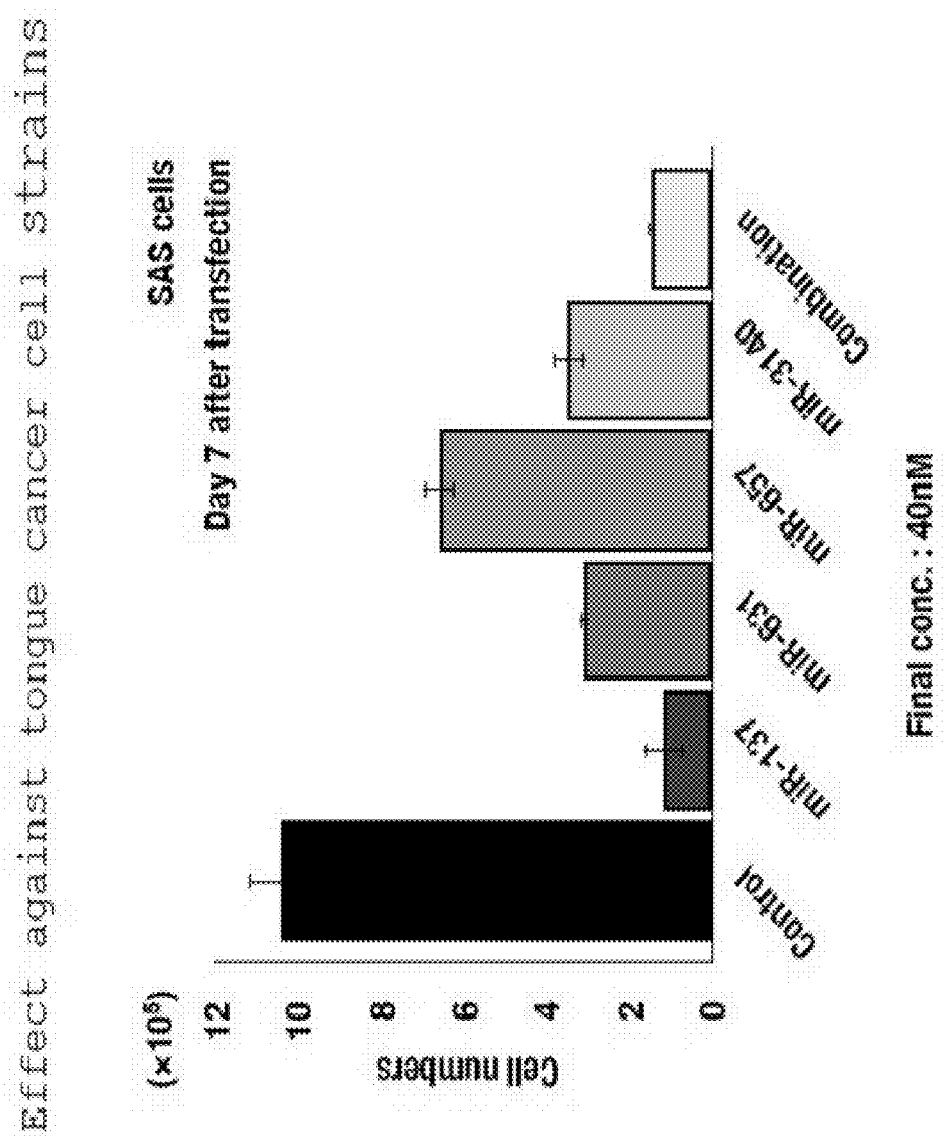
FIG. 5 shows the effect of the miRNA of the present invention on tongue cancer cell strain (SAS cells).
Figure 6:
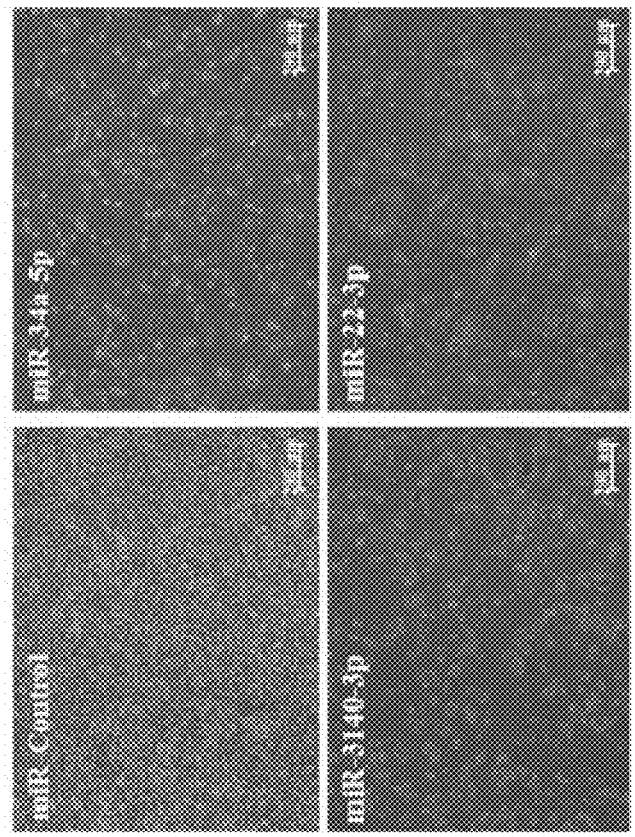
FIG. 6 shows the effect of the miRNA of the present invention on mesothelioma cell strain (MSTO-211H cells).
Figure 6:
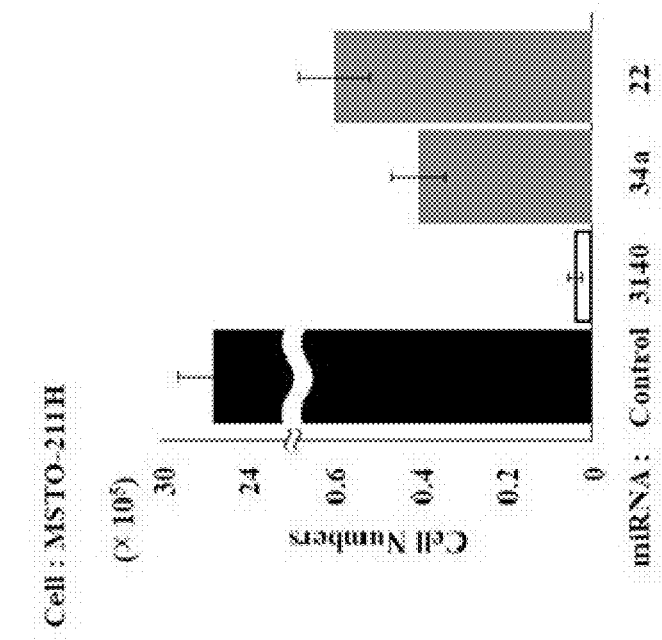
Figure 7:
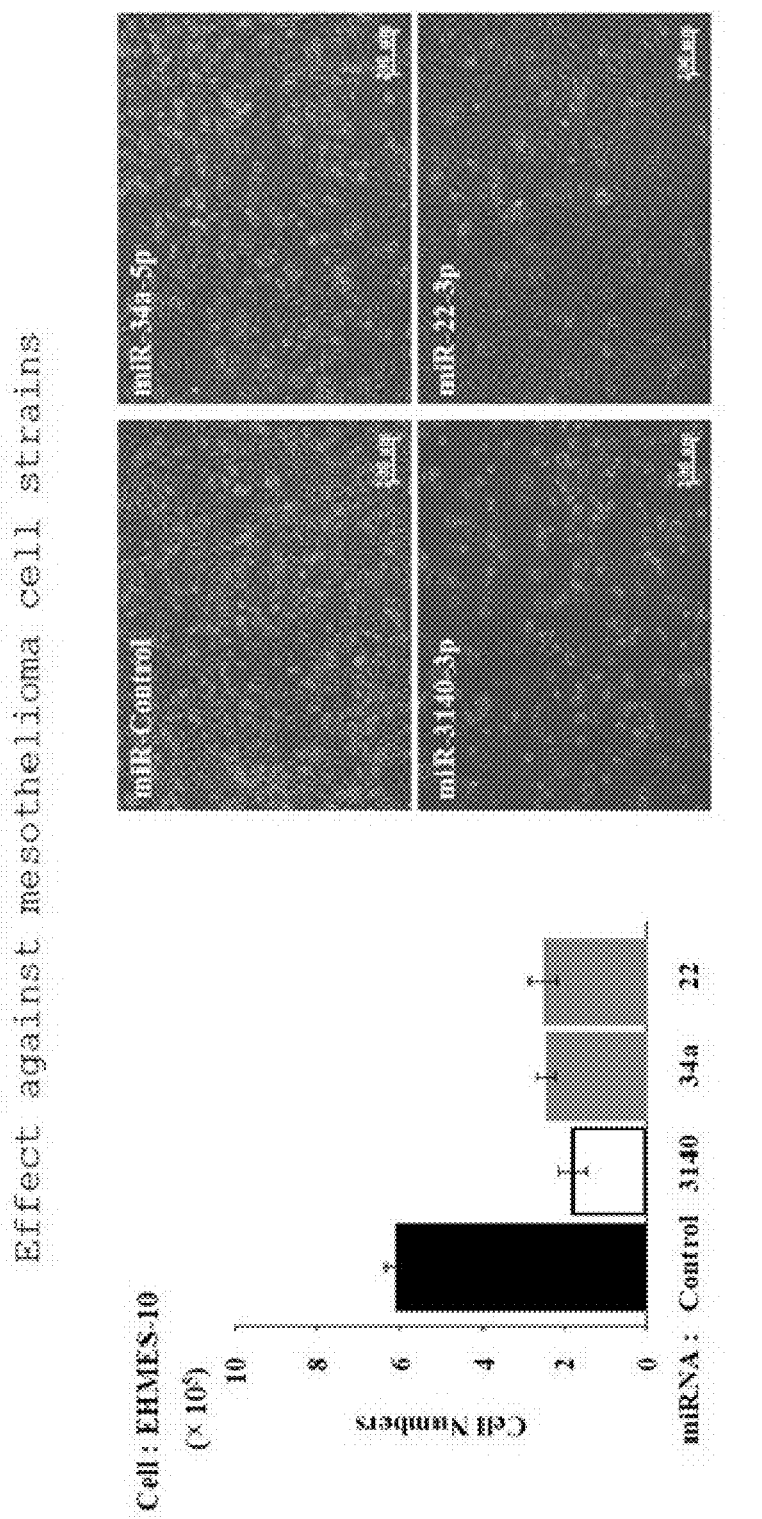
FIG. 7 shows the effect of the miRNA of the present invention on mesothelioma cell strain (EHMES-10 cells).
Figure 8:
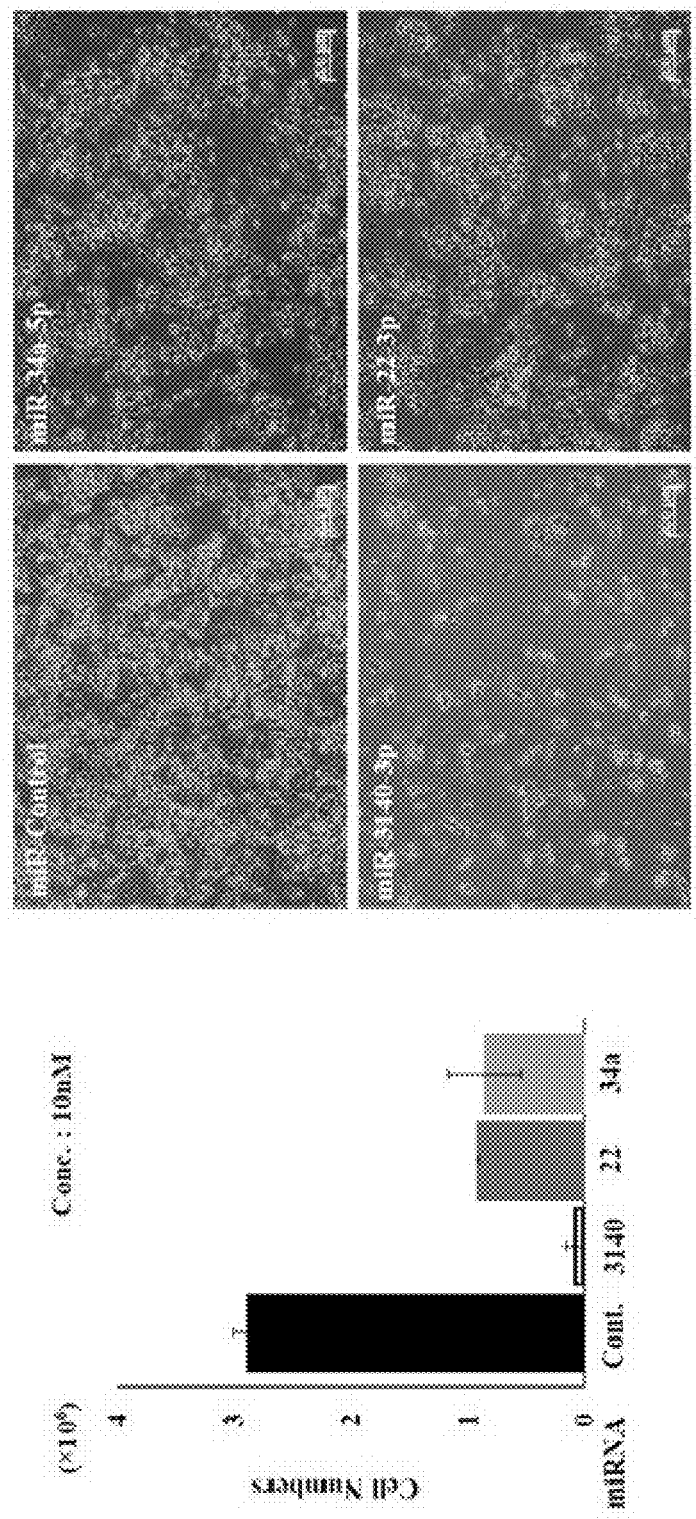
FIG. 8 shows the effect of the miRNA of the present invention on uterine sarcoma cell strain (MES-SA cell).
Figure 9:
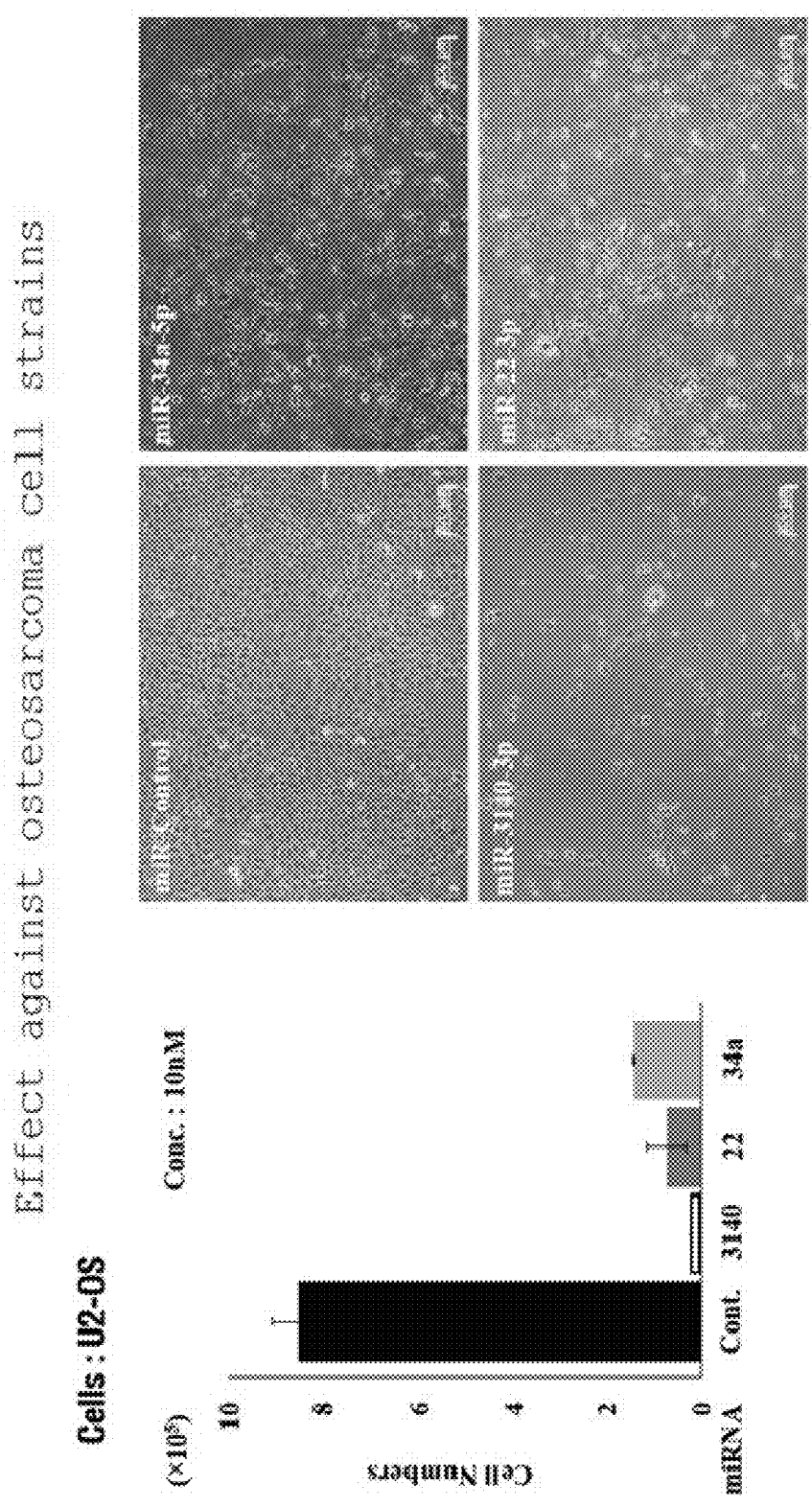
FIG. 9 shows the effect of the miRNA of the present invention on osteosarcoma cell strain (U2-OS cells).

(2) Tongue cancer cell strain (SAS) (FIG. 5)

Four miRNAs (miR-137-3p, miR-631-5p, miR-657-3p, and miR-3140-3p) were transfected into a tongue cancer cell strain (SAS), and cell proliferation was observed. Transfection was carried out with the following protocol.

1: To a 35 mm dish were added 500 μL of serum free medium (SFM) and 5 μL of RNAiMAX (Invitrogen).

2: To the solution from 1 was added 4 μL each of the miRNA solutions (see Table 3) (final concentration 10 nM).

3: This was incubated at room temperature for 20 minutes.

4: 1.5 mL of a cell suspension diluted to $6.7 \times 10^4$ cells/mL was added to the 35 mm dish.

5: This was incubated at 37° C. under 5% $CO_2$ condition.

6: Operations from 1-3 were repeated two days after transfection.

7: The solutions prepared in 6 were each added to the dish cultured in 5.

8: The cells were counted seven days after the first transfection.

As shown in FIG. 5, any of the four miRNAs showed cell growth inhibition effect against tongue cancer cell strain SAS.

TABLE 7

Table 3: miRNA dosage

| Stock(20 μM) | Control | miR 137 3p | miR 631 5p | miR 657 3p | miR 3140 3p | Combination |
|---|---|---|---|---|---|---|
| miR Control | 4 μL | 3 μL | 3 μL | 3 μL | 3 μL | |
| miR 137 3p | | 1 μL | | | | 1 μL |
| miR 631 5p | | | 1 μL | | | 1 μL |
| miR 657 3p | | | | 1 μL | | 1 μL |
| miR 3140 3p | | | | | 1 μL | 1 μL |
| Total | 4 μL | 4 μL | 4 μL | 4 μL | 4 μL | 4 μL |

(3) Malignant pleural mesothelioma cell strains, uterine sarcoma cell strain, and osteosarcoma cell strain (FIGS. 6-9)

Among the above four miRNAs, miR-3140-3p which had particularly high cell growth inhibition effect was transfected in each of malignant pleural mesothelioma cell strains (MSTO-211H and EHMES-10), uterine sarcoma cell strain (MES-SA), and osteosarcoma cell strain (U2-OS), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).

2: To the solution from 1 was added 1 μL each of miR-Control or miR-3140-3p, miR-22-3p, and miR-34a-5p (stock conc. 20 μM) (final concentration 10 nM).

3: This was incubated at room temperature for 20 minutes.

4: 1.5 mL of a cell suspension diluted to $6.7 \times 10^4$ cells/mL was added to the 35 mm dish.

5: This was incubated at 37° C. under 5% $CO_2$ condition.

6: The cells were counted four days after transfection.

As shown in FIGS. 6-9, in any of the cell strains, miR-3140-3p showed extremely high cell growth inhibition effect compared to prior art miR-22-3p and miR-34a-5p.

Figure 10:
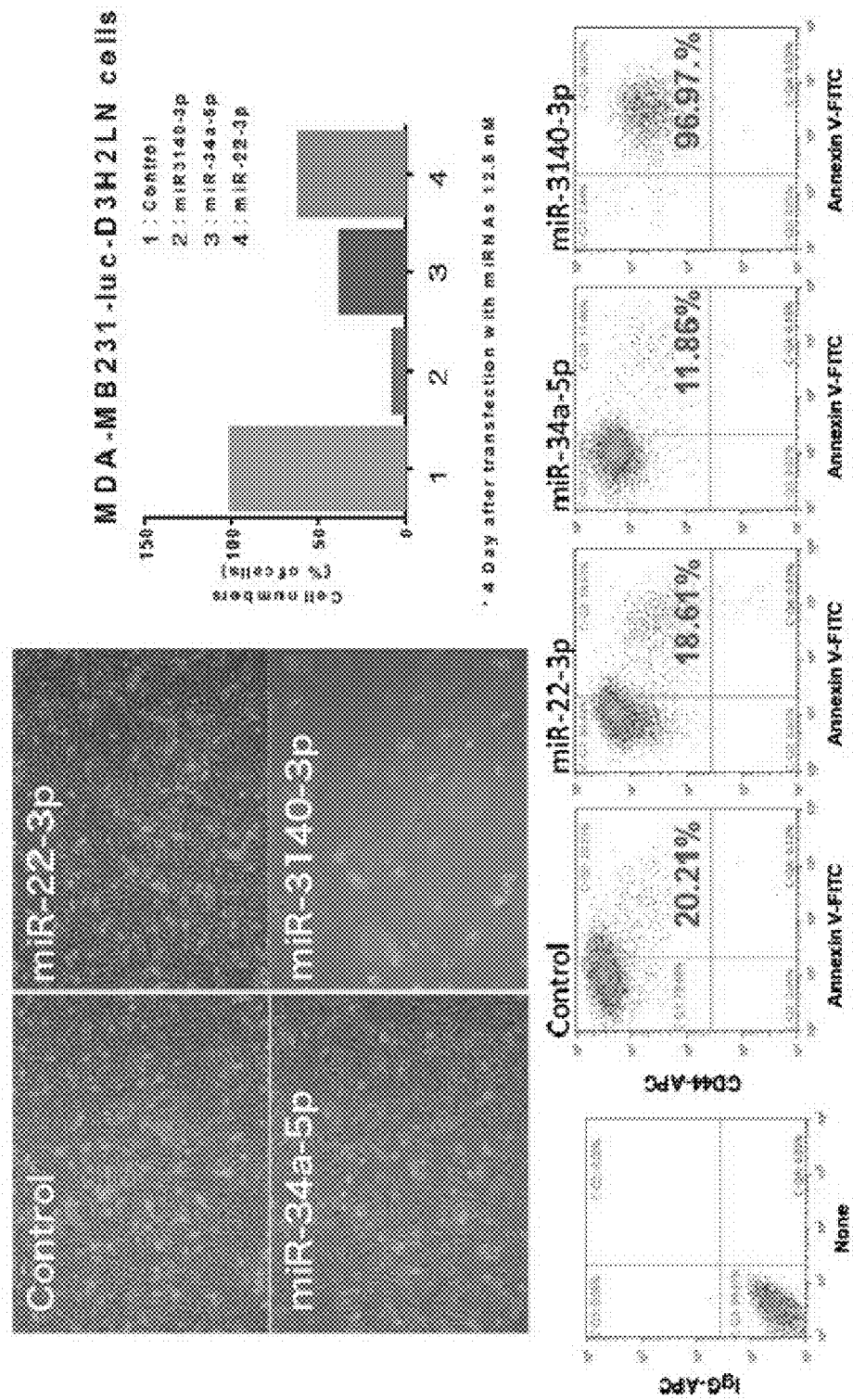
FIG. 10 shows the effect of the miRNA of the present invention on cancer stem cell strains (MDA-MB231-luc-D3H2LN cells).

(4) Breast cancer stem cell strain (MDA-MB231-luc-D3H2LN cells) (FIG. 10)

miR-3140-3p was transfected in a highly metastatic cancer cell strain of breast cancer (MDA-MB231-luc-D3H2LN cells), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).

2: To the solution from 1 was added 12.5 μL each of miR-Control or miR-3140-3p, miR-22-3p, and miR-34a-5p (stock conc. 2 μM) (final concentration 12.5 nM).

3: This was incubated at room temperature for 20 minutes.

4: 1.5 mL of a cell suspension diluted to 6.7×104 cells/mL was added to the 35 mm dish.

5: This was incubated at 37° C. under 5% CO2 condition.

6: The cells were counted four days after transfection.

Moreover, by the protocol below, the expression of apoptosis marker Annexin V in breast cancer cells transfected with miR-3140-3p was analyzed.

1: Transfection of miR-3140-3p was performed with a protocol similar to that described above.

2: Six days after transfection, cells were recovered together with the supernatant.

3: Samples for FACS were prepared according to the protocol of the Annexin V assay kit.

4: Cells stained by Annexin V-FITC were stained with an antibody against cancer stem cell marker CD44 (eBioscience).

5: The prepared samples were analyzed with Cell Sorter (SONY).

As shown in FIG. 10 top, miR-3140-3p showed extremely high cell growth inhibition effect against breast cancer stem cell strain (MDA-MB231-luc-D3H2LN cells).

Moreover, as shown in FIG. 10 bottom, in breast cancer stem cells at six days after transfection of miR-3140-3p, apoptosis marker Annexin V was highly positive (96.97%). In other words, it was shown that miR-3140-3p significantly induces apoptosis against cancer stem cells.

Figure 11:
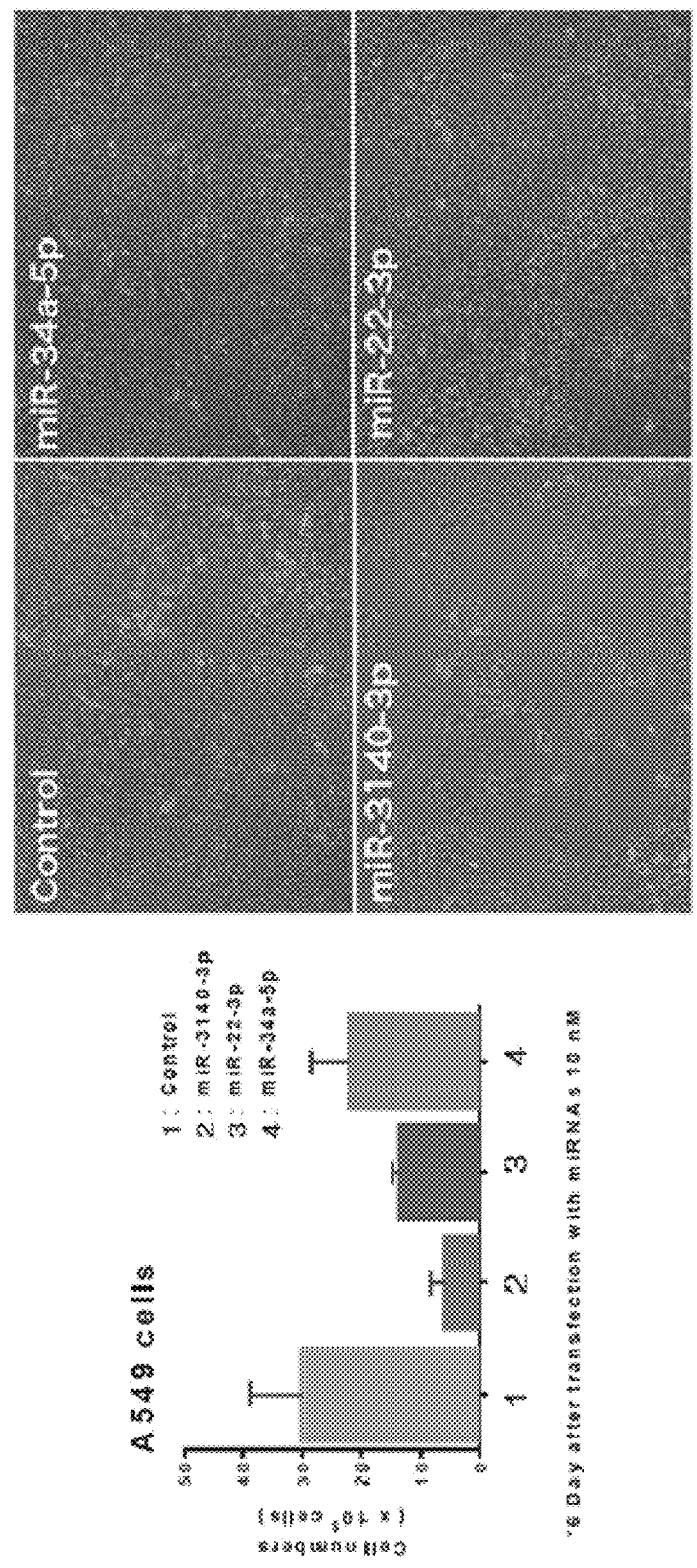
FIG. 11 shows the effect of the miRNA of the present invention on lung cancer cell strain (A549 cells).

(5) Lung cancer cell strain (A549) (FIG. 11)

miR-3140-3p was transfected into lung cancer cell strain (A549), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).

2: To the solution from 1 was added 1 μL each of miR-Control or miR-3140-3p, miR-22-3p, and miR-34a-5p (stock conc. 20 μM) (final concentration 10.0 nM).

3: This was incubated at room temperature for 20 minutes.

4: 1.5 mL of a cell suspension diluted to $6.7 \times 10^4$ cells/mL was added to the 35 mm dish.

5: This was incubated at 37° C. under 5% CO2 condition.

6: The cells were counted six days after transfection.

As shown in FIG. 11, miR-3140-3p showed extremely high cell growth inhibition effect against lung cancer cell strain (A549).

Figure 12:
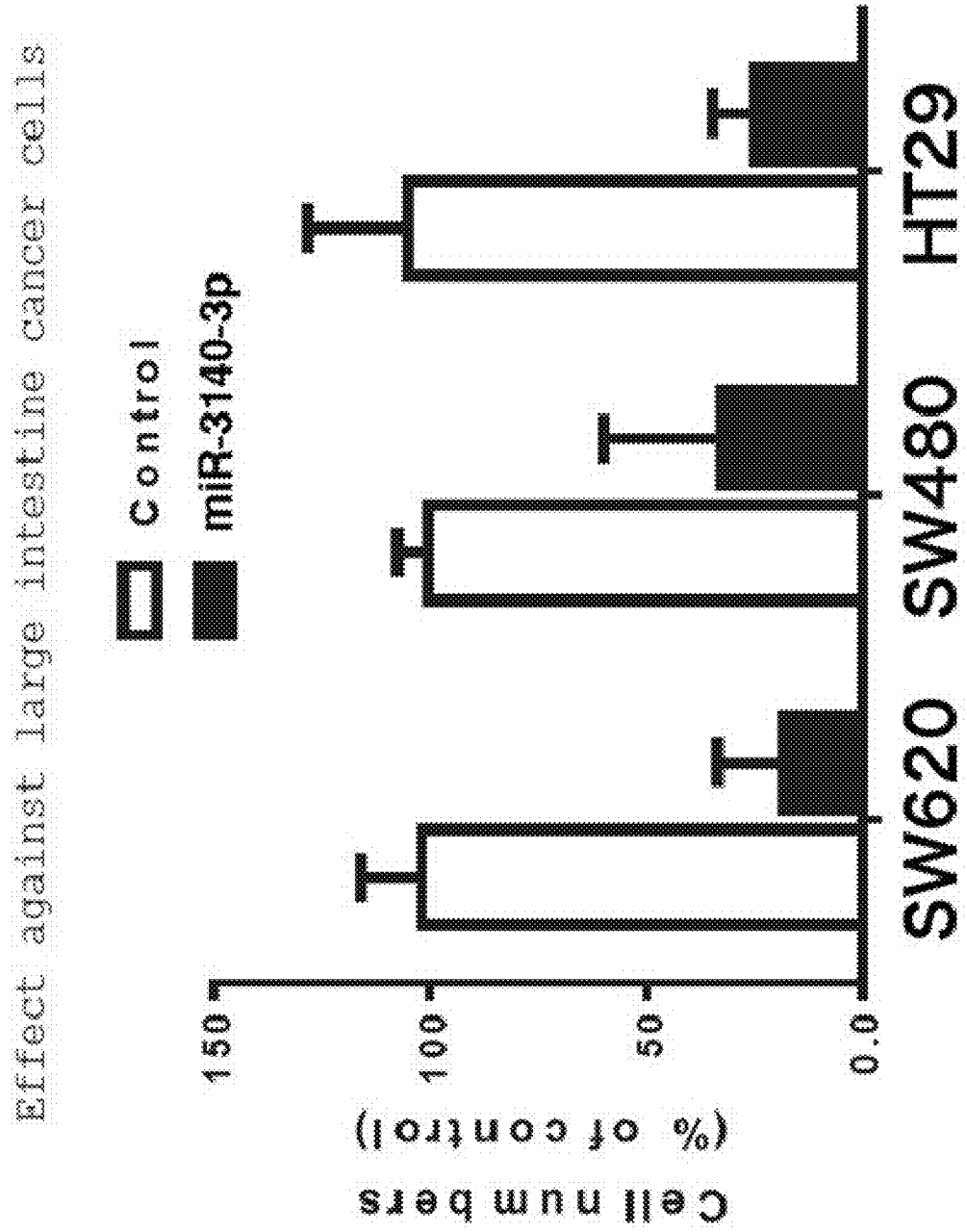
FIG. 12 shows the effect of the miRNA of the present invention on large intestine cancer cell strains (SW620 cells, SW480 cells, and HT29 cells).

(6) Large intestine cancer cell strains (SW620, SW480, and HT29) (FIG. 12)

miR-3140-3p was transfected into large intestine cancer cell strains (SW620, SW480, and HT29), and cell proliferation was observed. Transfection was carried out with the following protocol.

1: To a 35 mm dish were added 500 μL of serum free medium (SFM) and 5 μL of RNAiMAX (Invitrogen).

2: To the solution from 1 was added 12.5 μL each of miR-Control or miR-3140-3p, miR-22-3p, and miR-34a-5p (stock conc. 2 μM) (final concentration 10.0 nM).

3: This was incubated at room temperature for 20 minutes.

4: 1.5 mL of a cell suspension diluted to 6.7×104 cells/mL was added to the 35 mm dish.

5: This was incubated at 37° C. under 5% CO2 condition.

6: The cells were counted seven days after transfection.

Results are shown in FIG. 12. Setting the number of control introduction cells as 100%, the survival rate of cells in which miR-3140-3p was introduced was shown in %. As shown in FIG. 12, miR-3140-3p showed extremely high cell growth inhibition effect against any of the large intestine cancer cell strains.

Figure 13:
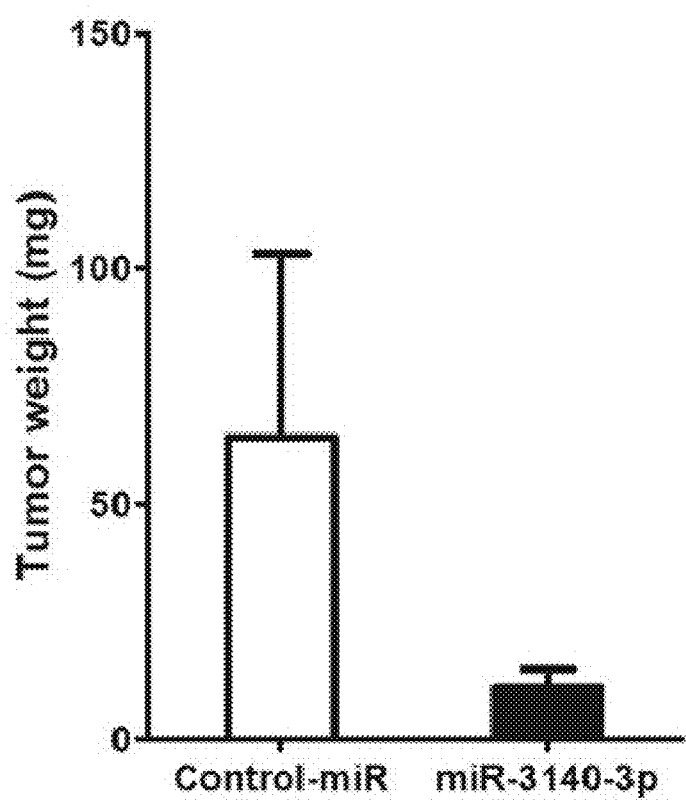
FIG. 13 shows the cancer therapeutic effect of the miRNA of the present invention in vivo.

Experiment 4. Antitumor effect of the miRNA of the present invention in vivo (malignant pleural mesothelioma cells) (FIG. 13)

In order to verify the antitumor effect of the miRNA of the present invention in vivo, experiments was performed with laboratory animals transplanted with malignant pleural mesothelioma cells.

(1) Preparation of cells

Malignant pleural mesothelioma cells MSTO-211H cells were used.

1: The cells on the dish were washed twice with PBS (-).

2: The cells were detached with trypsin.

3: This was suspended in a medium, and cells were counted.

4: Centrifugation at a condition of 1000 rpm for 3 min was performed to pellet down.

5: The cells were resuspended in PBS (-) in order to obtain $2.0 \times 10^7$ cells/mL.

(2) Cell transplantation to mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA administration

Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From four days after transplantation, the nucleic acid was administered every one or two days.

2: A total of 13 administrations were performed, and 34 days after transplantation was set as the endpoint.

3: Mice were dissected, and the subcutaneous tumor was resected and weighed.

Experimental results are shown in FIG. 13 (n=3). As shown in FIG. 13, compared to the control group, the tumor weight was significantly lower in mice in which miR-3140-3p was introduced at the tumor site.

Figure 14:
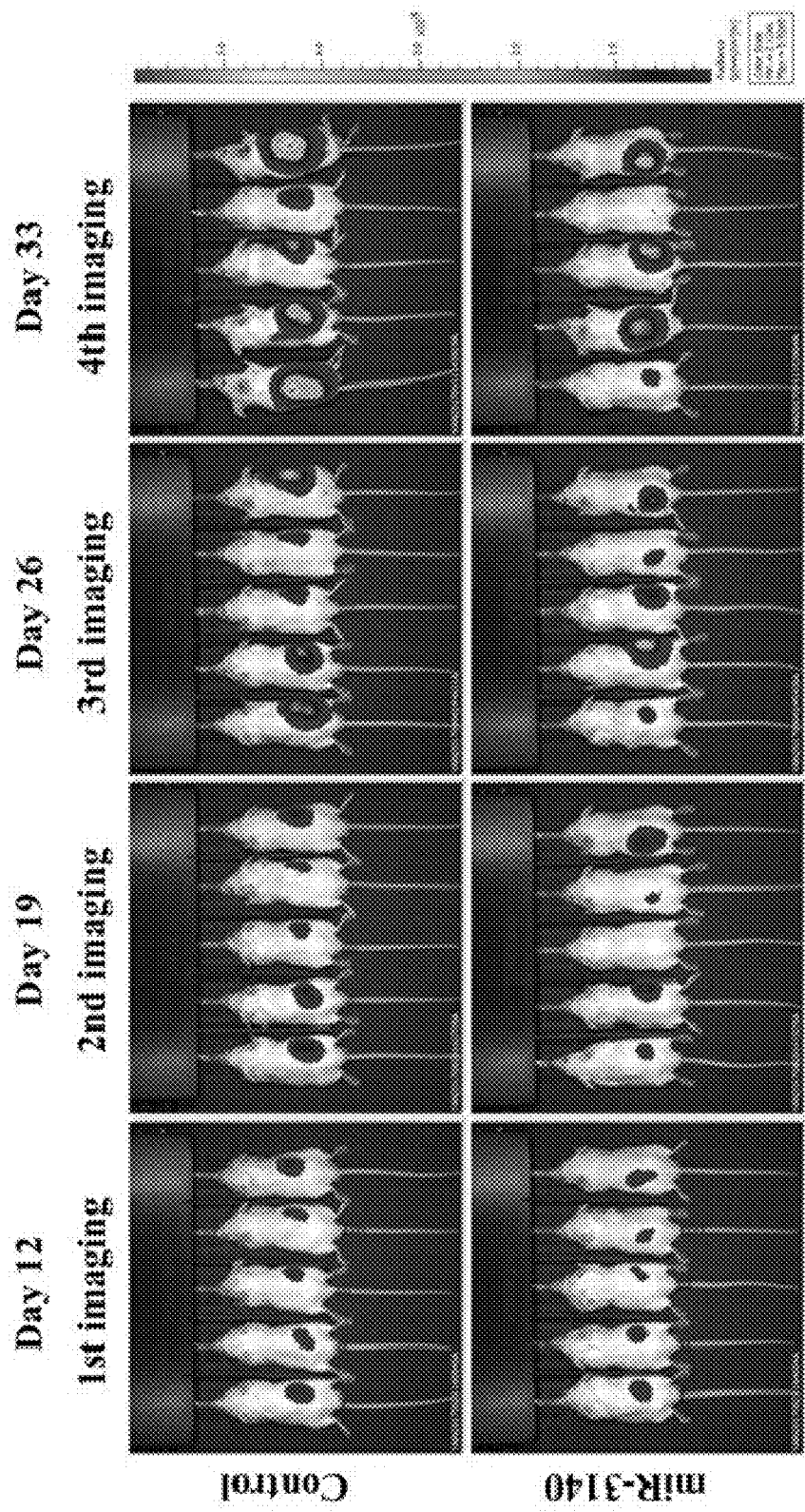
FIG. 14 shows imaging analysis results of tumor tissues at 12, 19, 26, and 33 days after tumor cell transplantation.
Figure 15:
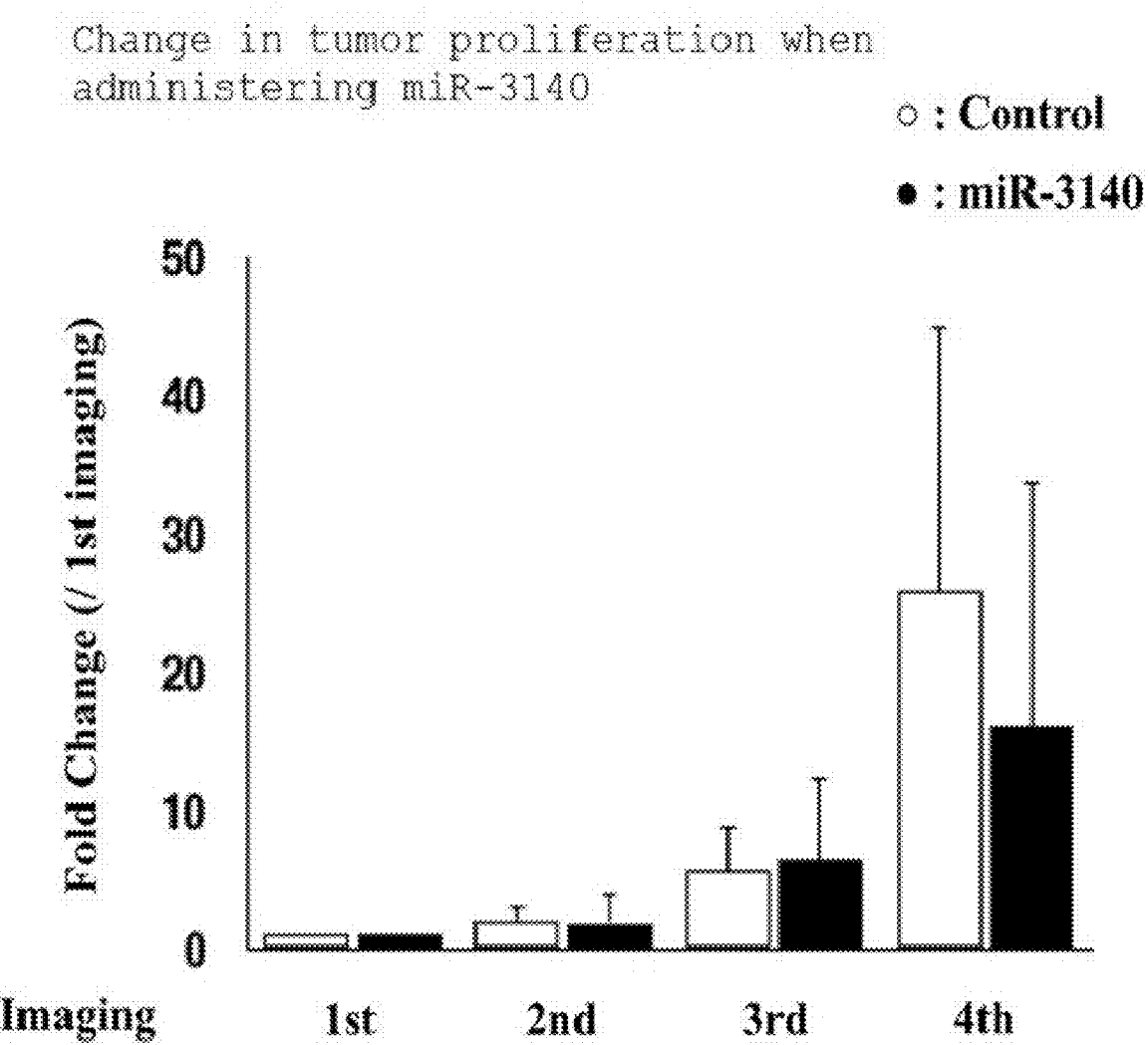
FIG. 15 shows a graph quantifying the imaging analysis results from FIG. 14.
Figure 16:
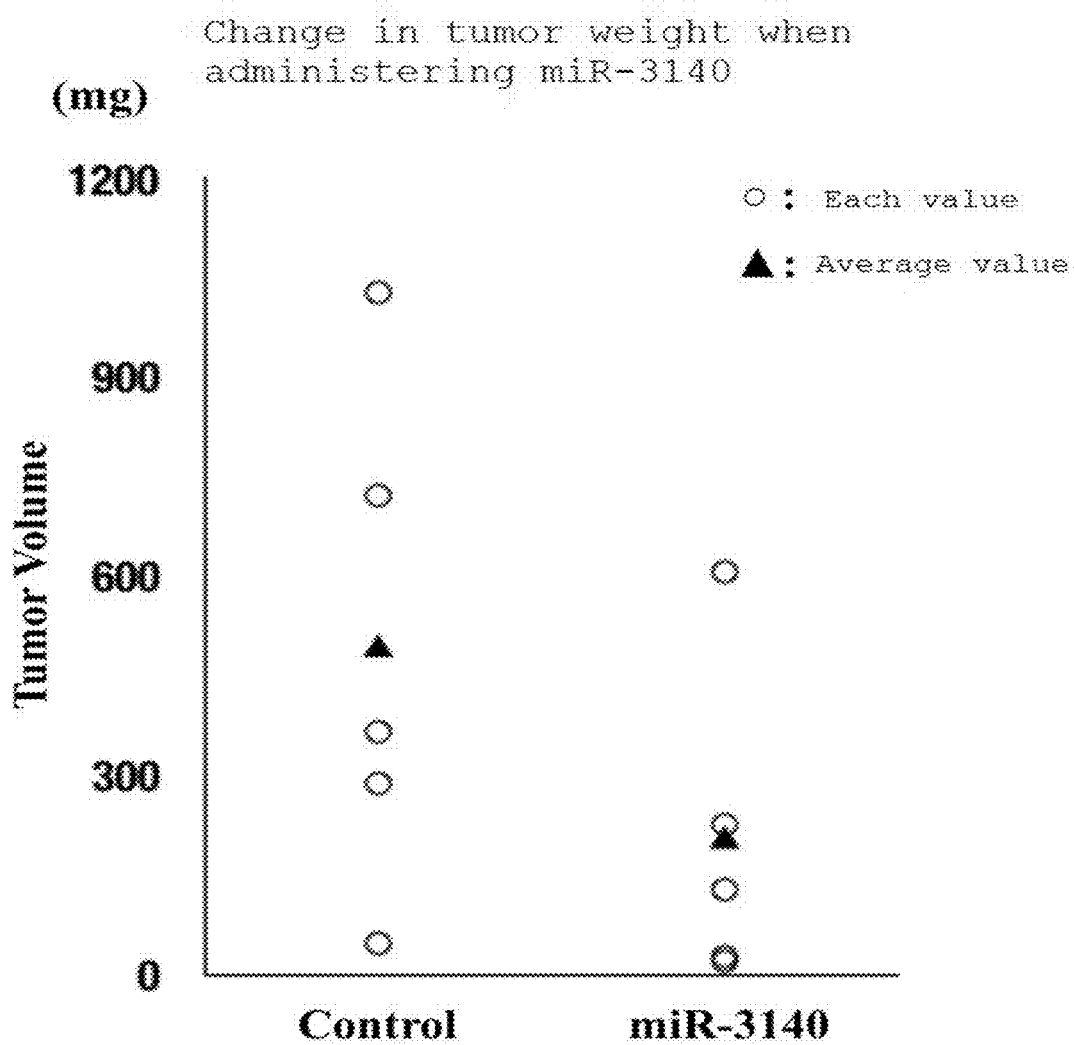
FIG. 16 shows the results of comparing tumor weights at endpoint.

Experiment 5. Antitumor effect of the miRNA of the present invention in vivo (malignant pleural mesothelioma cells) (FIG. 14-16)

(1) Preparation of cells

Malignant pleural mesothelioma cells EHMES-10 cells were used.

1: The cells on the dish were washed twice with PBS (-).

2: The cells were detached with trypsin.

3: This was suspended in a medium, and cells were counted.

4: Centrifugation at a condition of 1000 rpm for 3 min was performed to pellet down.

5: The cells were resuspended in PBS (-) in order to obtain $2.0 \times 10^7$ cells/mL.

(2) Cell transplantation to mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA administration

Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From two days after transplantation, the nucleic acid was administered every one or two days.

2: A total of 13 administrations were performed, and 33 days after transplantation was set as the endpoint.

3: At 12, 19, 26, and 33 days after transplantation, luciferin was intraperitoneally administered for imaging in order to trace the tumor size.

4: Mice were dissected at the endpoint, and the subcutaneous tumor was resected and weighed.

Imaging analysis results of tumor tissues at 12, 19, 26, and 33 days after tumor cell transplantation are shown in FIG. 14 and FIG. 15. As shown in FIGS. 14 and FIG. 15, compared to the control group, expansion of the tumor was suppressed in mice in which miR-3140-3p was introduced at the tumor site. Moreover, a similar result was shown in FIG. 16 which compares the tumor weight at endpoint.

Figure 17:
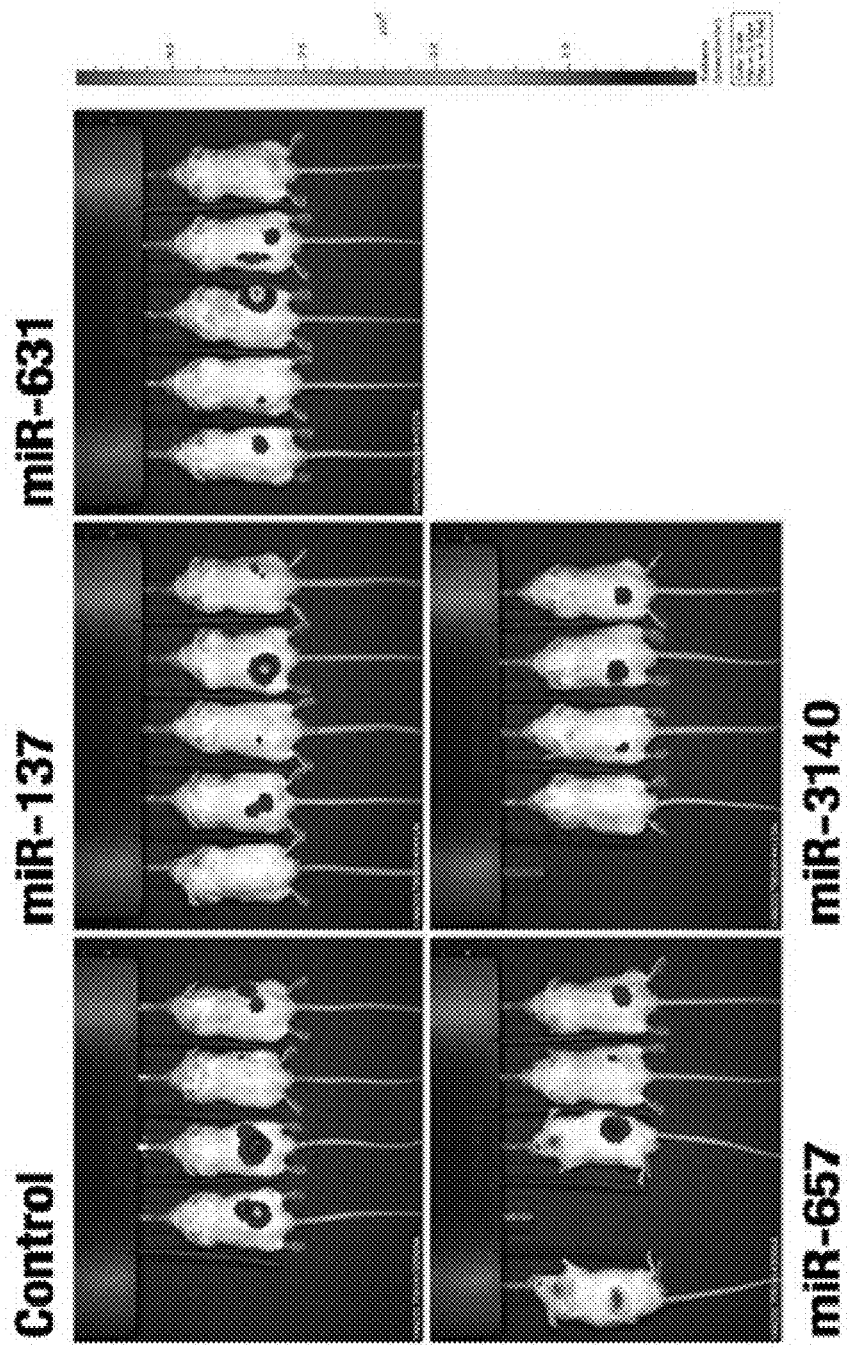
FIG. 17 shows imaging analysis results of tumor tissues after tumor cell transplantation.
Figure 18:
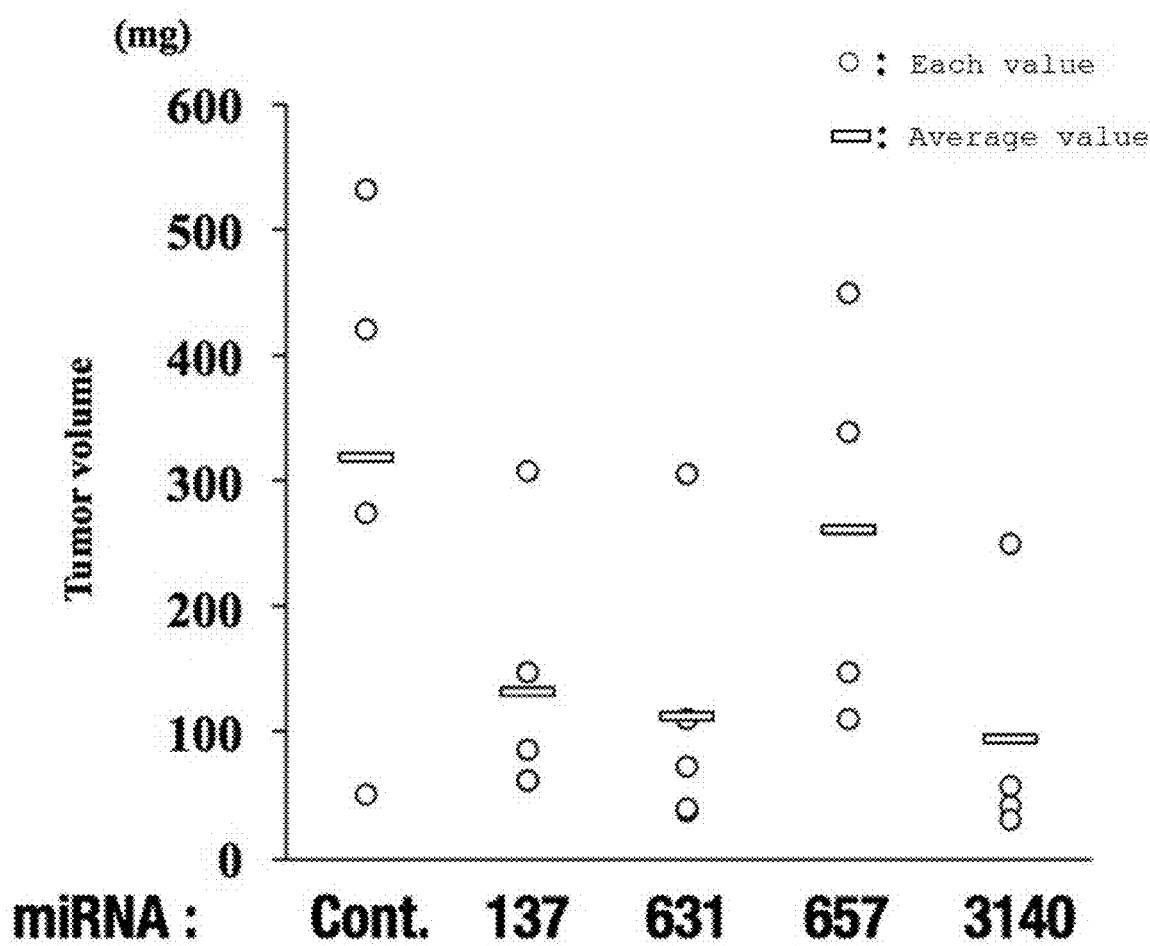
FIG. 18 shows the results of comparing tumor weights at endpoint.

Experiment 6. Antitumor effect of the miRNA of the present invention in vivo (tongue cancer cell) (FIGS. 17 and 18)

(1) Preparation of cells

Tongue cancer cell strain HSC-4 cells were used.

1: The cells on the dish were washed twice with PBS (-).

2: The cells were detached with trypsin.

3: This was suspended in a medium, and cells were counted.

4: Centrifugation at a condition of 1000 rpm for 3 min was performed to pellet down.

5: The cells were resuspended in PBS (-) in order to obtain $2.0 \times 10^7$ cells/mL.

(2) Cell transplantation to mice

Six weeks-old C-B-17/Icr-scid/scid Jcl (SCID mouse) were used as mice. SCID mice were subcutaneously administered 100 µL of the prepared cell suspension, and the cells were allowed to settle.

(3) miRNA administration

Negative control which is the control sequence and miR-3140-3p, miR-137, miR-631 and miR-657 which are the miRNAs of the present invention were employed. A6K (from 3D Matrix) was employed as the nucleic acid delivery reagent. The administration of miRNA to mice was carried out with the following protocol.

1: 100 µM of the nucleic acid (miRNA) was diluted with 10% saline and sterilized water in order to obtain 71.4 µM.

2: 1% A6K solution was sonicated for 5 minutes before use. 3: The diluted nucleic acid and the 1% A6K solution were mixed at a proportion of 1:1 to give the administration nucleic acid.

4: SCID mice were subcutaneously administered (tumor site) 50 µL each of the administration nucleic acid.

(5) Evaluation

The experimental results were evaluated with the following protocol.

1: From three days after transplantation, the nucleic acid was administered every one or two days.

2: A total of 11 administrations were performed, and 28 days after transplantation was set as the endpoint.

3: At 7, 14, 21, and 28 days after transplantation, luciferin was intraperitoneally administered for imaging in order to trace the tumor size.

4: Mice were dissected at the endpoint, and the subcutaneous tumor was resected and weighed.

Imaging analysis results of tumor tissues after tumor cell transplantation are shown in FIG. 17. As shown in FIG. 17, compared to the control group, expansion of the tumor was suppressed in mice in which the miRNA of the present invention was introduced at the tumor site. Moreover, a similar result was shown in FIG. 18 which compares the tumor weight at endpoint.

From the above results, it was shown that the miRNA of the present invention also exerts extremely strong antitumor effect in vivo.

Experiment 7. Antitumor effect of the miRNA of the present invention in vivo (malignant pleural mesothelioma cells) (FIGS. 19-28)

The tumor suppression effect of miR-3140-3p in vivo was investigated with intrathoracic orthotopic transplantation model mouse.

Six weeks-old male mice (C-B-17/Icr-scid/scid Jcl) were used as mice. Malignant pleural mesothelioma cell strain EHMES-10 which expresses the luciferase gene was used as the tumor cell.

The experiment protocol is shown below.

1: Mice were intraperitoneally administered 0.1 mL per 10 g of body weight of a mixed anesthetic drug of medetomidine hydrochloride, midazolam, and butorphanol tartrate.

2: After anesthesia, mouse chest hair was shaved, and an incision was made in the epidermis with scissors.

3: In the mouse pleural cavity 100 µL of tumor cells ($3 \times 10^7$ cells/mL) was transplanted with a 27 G syringe for insulin.

4: Three days after transplantation, imaging of tumor cells was performed with IVIS Spectrum CT In vivo Imaging System.

5: After imaging, grouping was performed with successfully transplanted mice.

6: Mice were intraperitoneally administered 0.1 mL per 10 g of body weight of a mixed anesthetic drug of medetomidine hydrochloride, midazolam, and butorphanol tartrate to anesthetize the mice.

7: After anesthesia, 100 µL of miRNA/A6K mixture was administered in the mouse pleural cavity.

8: Imaging was performed every week from the first imaging, and tumor expansion was observed.

9: The time and date of death of the mice was recorded, and mice survival rate was calculated.

Figure 19:
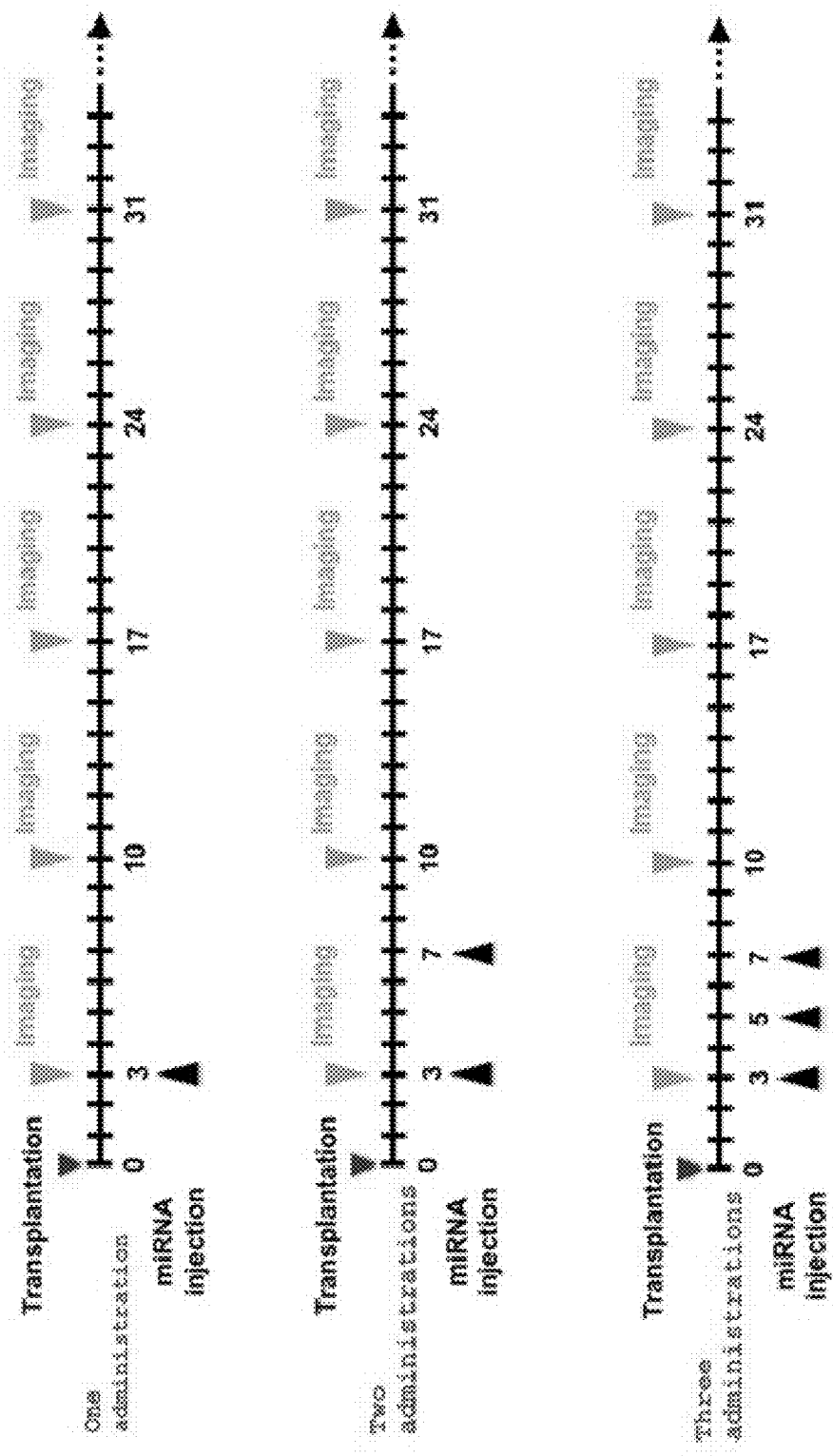
FIG. 19 shows the schedule in Experiment 7.

Administration and imaging schedule is shown in FIG. 19. The mixed anesthetic drug of medetomidine hydrochloride, midazolam, and butorphanol tartrate was prepared as in Table 4 below. The miRNA/A6K mixture was prepared as in Table 5. Moreover, the control group was administered the RNA shown in Table 6 instead of the miRNA of the present invention.

Note that in order to improve expression efficiency, miRNA was administered as a double-strand in combination with a complementary strand comprising partial mismatch.

TABLE 8

| Table 4 Preparation of mixed anesthetic drug | | | |
|---|---|---|---|
| Medetomidine hydrochloride (1 mg/mL) | Midazolam (5 mg/mL) | Butorphanol tartrate (0.5 mg/mL) | Water for injection |
| Required amount of stock solution 0.75 mL | 2 mL | 2.5 mL | 19.75 mL |

TABLE 9

Table 5 Preparation of miRNA/A6K mixture

| | /120 μL |
|---|---|
| 100 μM miRNA | 40 μL |
| 10% saline | 10.8 μL |
| 1% A6K | 50 μL |
| Water for injection | 9.2 μL | miRNA is administered at 3.2 nmol (45 μg) per mouse.

TABLE 10

Table 6 Sequences of control and miR-3140-3p

| | Sequence |
|---|---|
| Control | 5' UUCUCCGAACGUGUCACGU (SEQ ID NO. 30) |
| | 5' ACGUCACACGUUCGGAGAA (SEQ ID NO. 31) |
| miR-3140-3p | 5' AGCUUUUGGGAAUUCAGGUAGU (SEQ ID NO. 2) |
| | 5' UACCUGAAUUCCCAAAAGCUUU (SEQ ID NO. 32) |

Experimental results are shown in FIG. 20 to FIG. 28.

Figure 20:
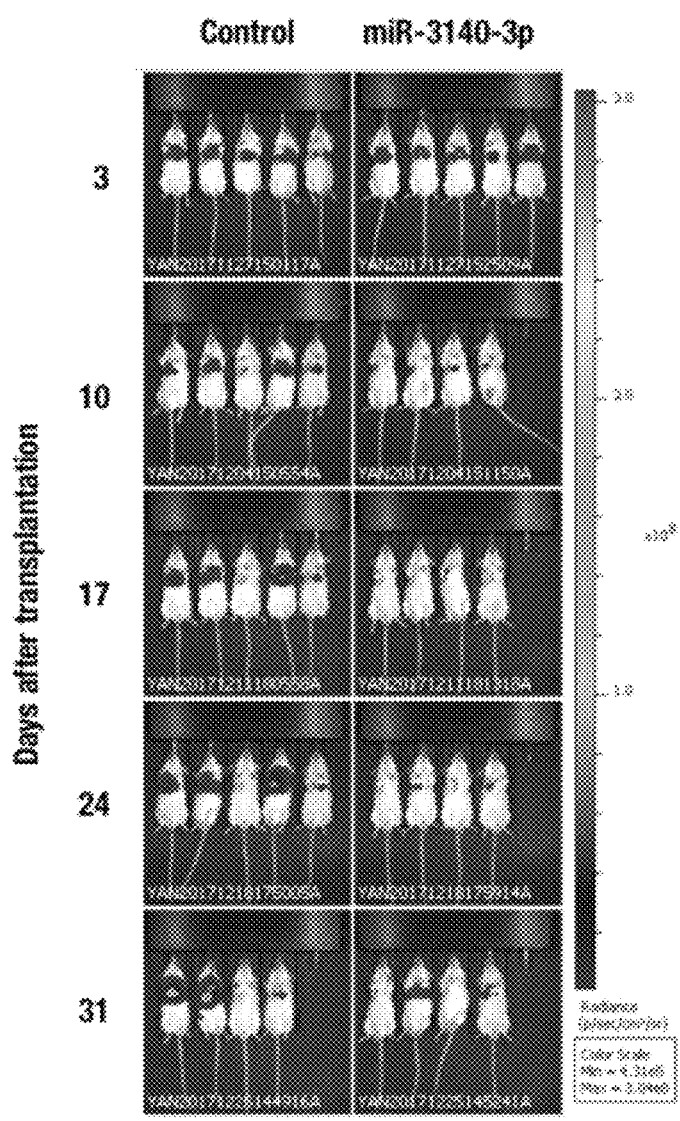
FIG. 20 shows the imaging results when miR-3140-3p is administered once.

In the group with one administration of miR-3140-3p, tumor reduction was seen by the second imaging (Day 10 after transplantation), and the effect had persisted until the fourth imaging (Day 24 after transplantation) (FIG. 20).

Figure 21:
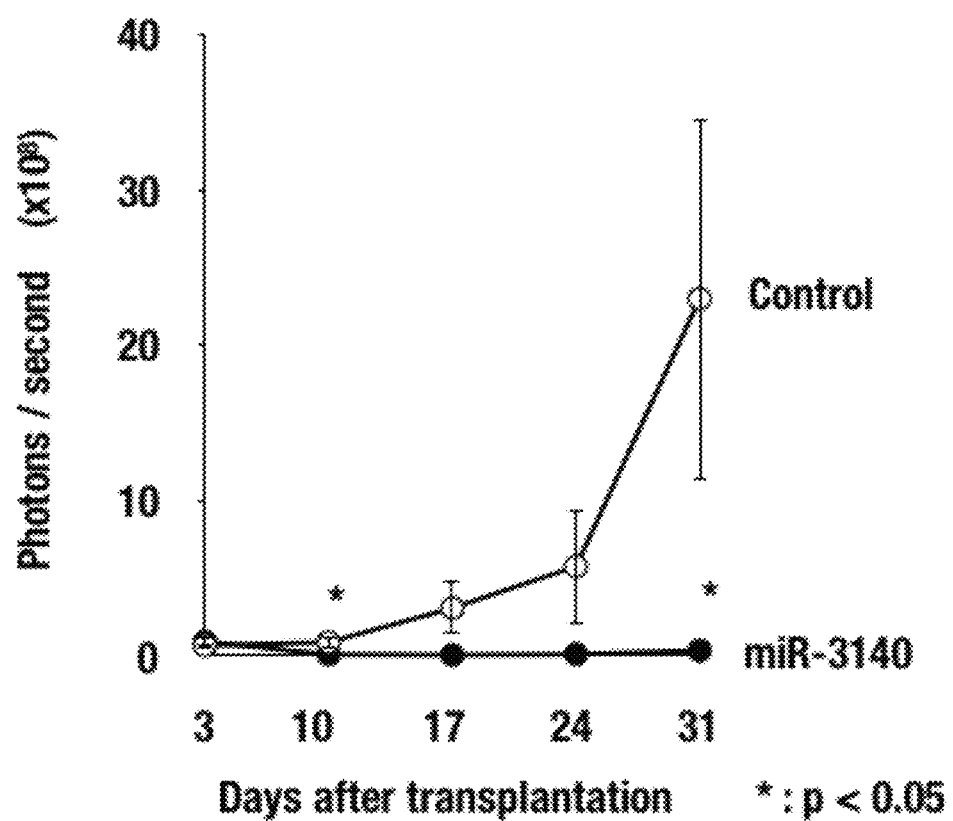
FIG. 21 shows the imaging results when miR-3140-3p is administered once.

The imaging results were digitized and graphed, and it was shown that miR-3140-3p significantly suppressed tumor expansion (FIG. 21).

Figure 22:
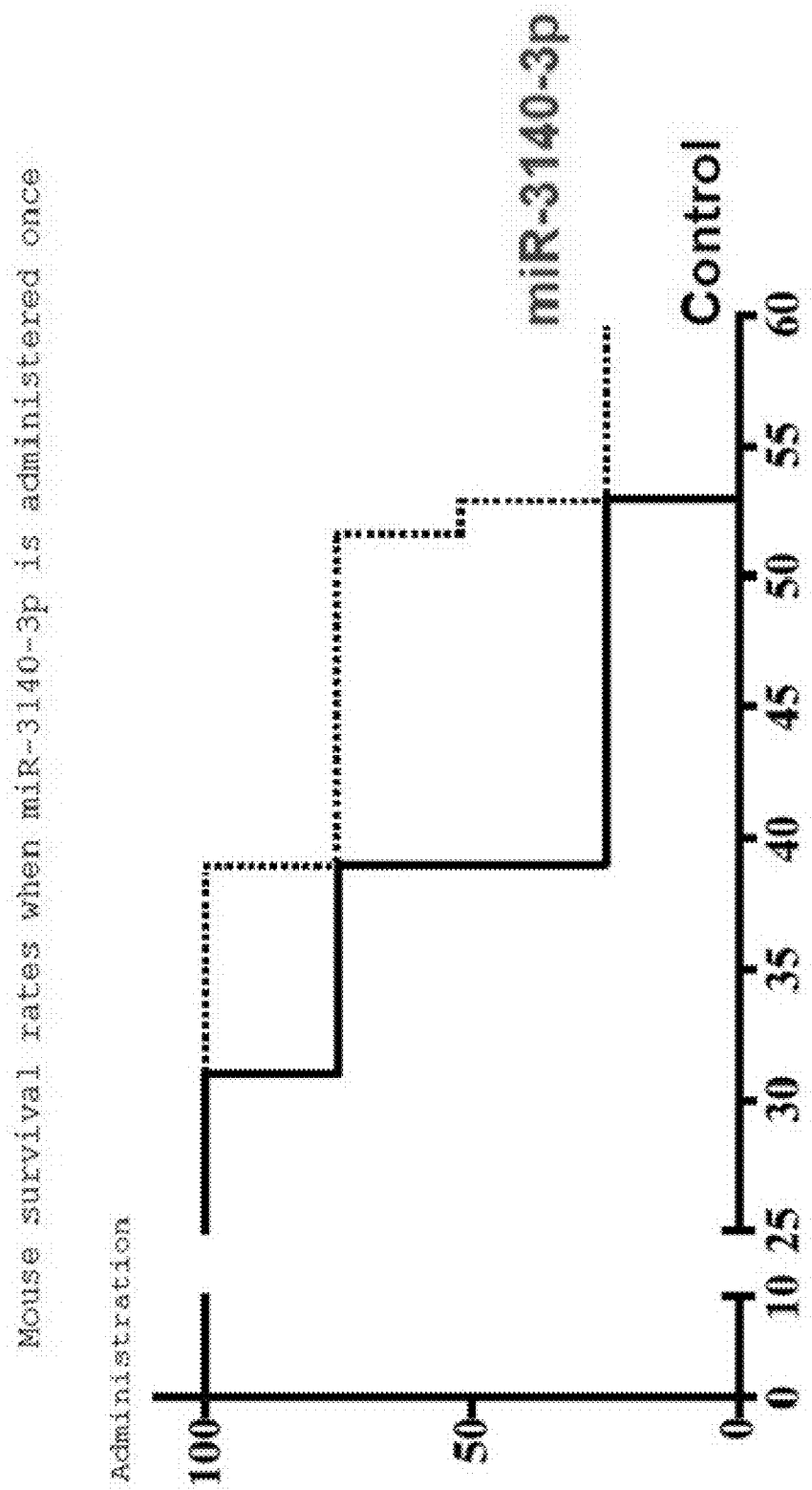
FIG. 22 shows survival rates of mice when miR-3140-3p is administered once.
Figure 23:
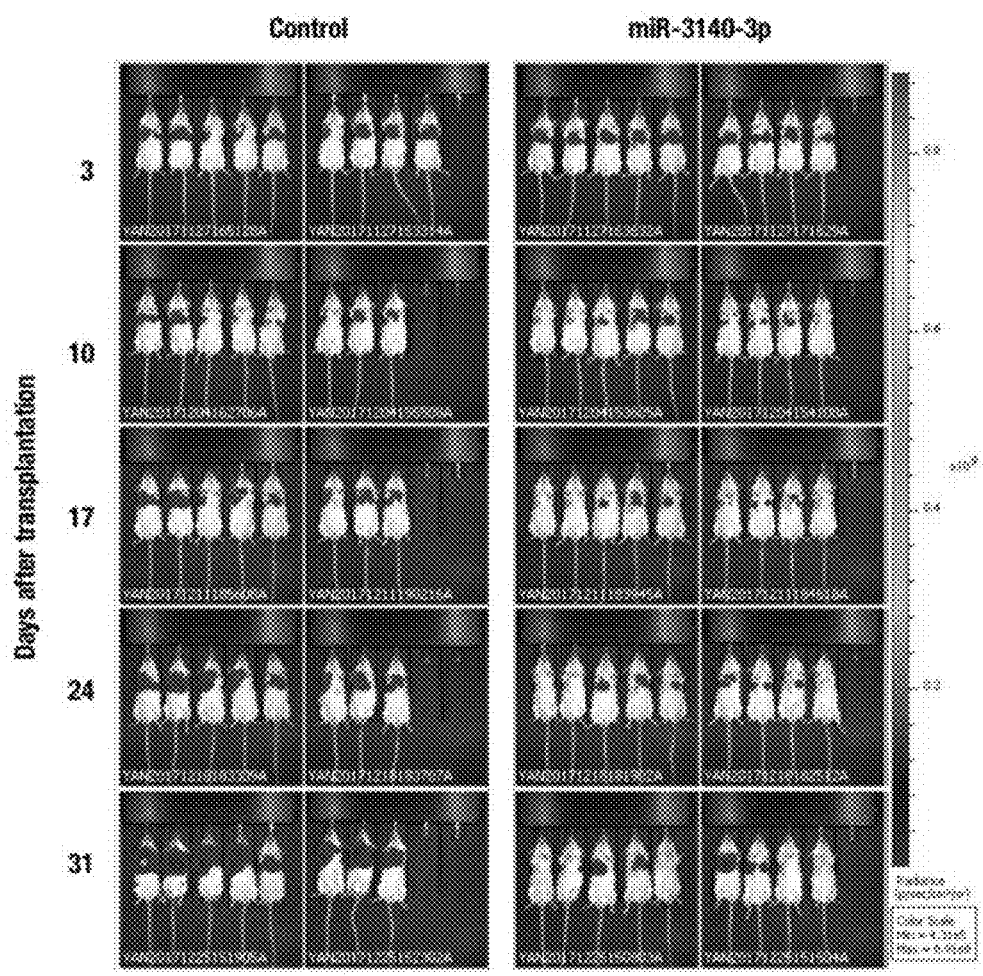
FIG. 23 shows the imaging results when miR-3140-3p is administered twice.
Figure 24:
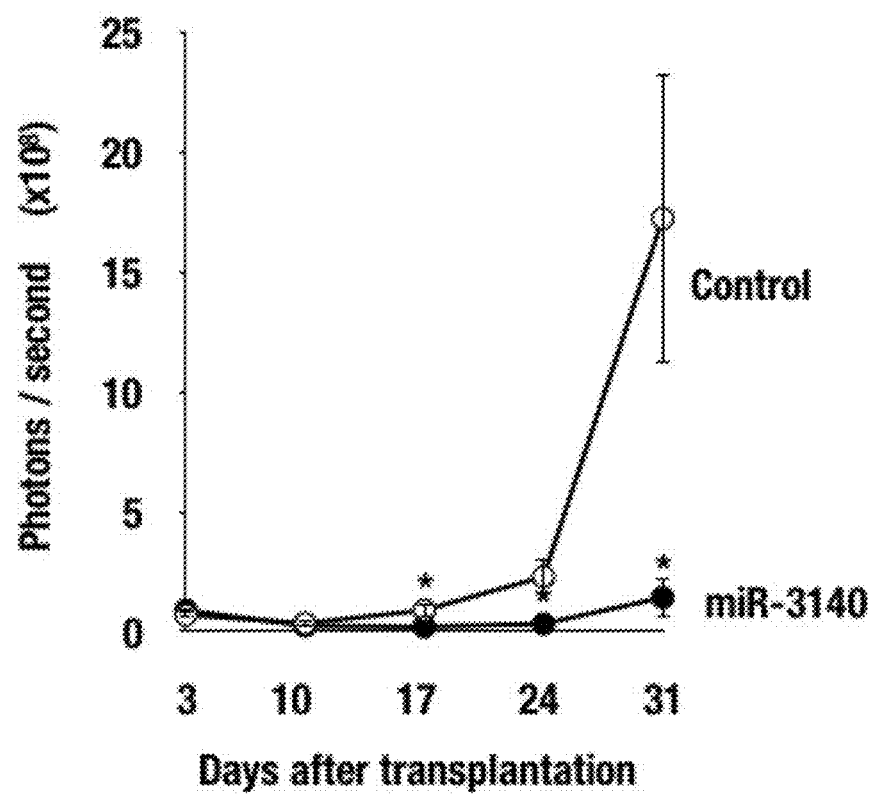
FIG. 24 shows the imaging results when miR-3140-3p is administered twice.
Figure 25:
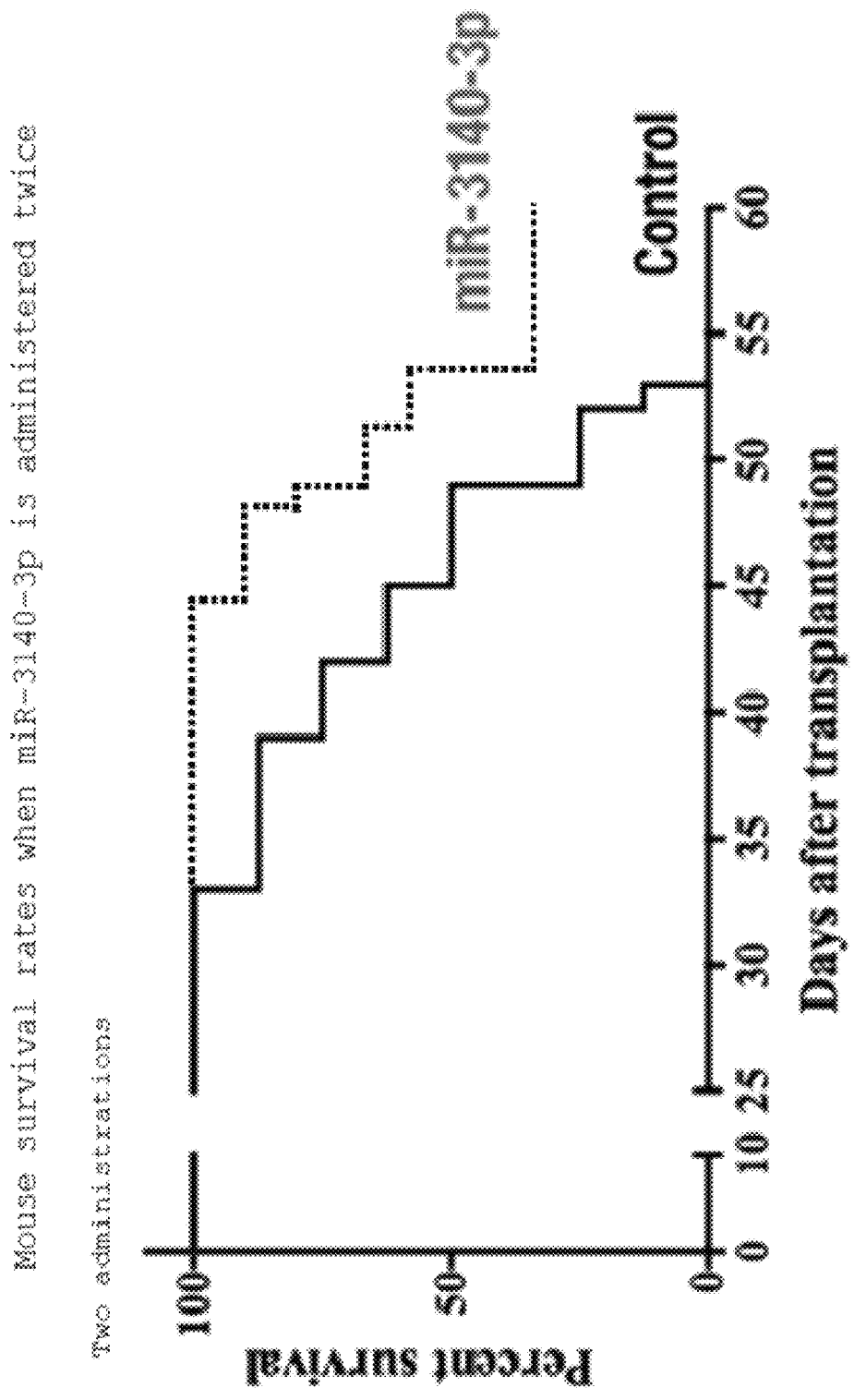
FIG. 25 shows the survival rates of mice when miR-3140-3p is administered twice.
Figure 26:
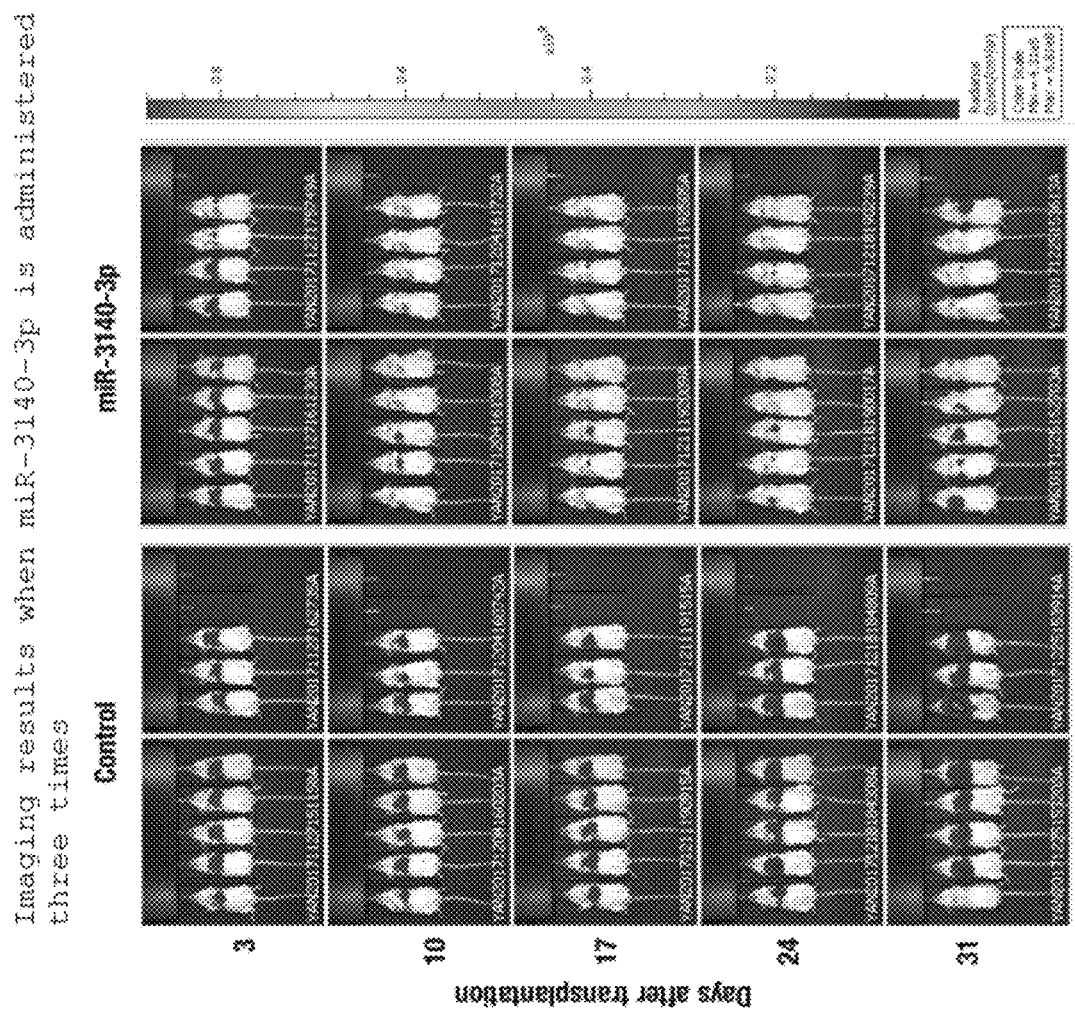
FIG. 26 shows the Imaging results when miR-3140-3p is administered three times.
Figure 27:
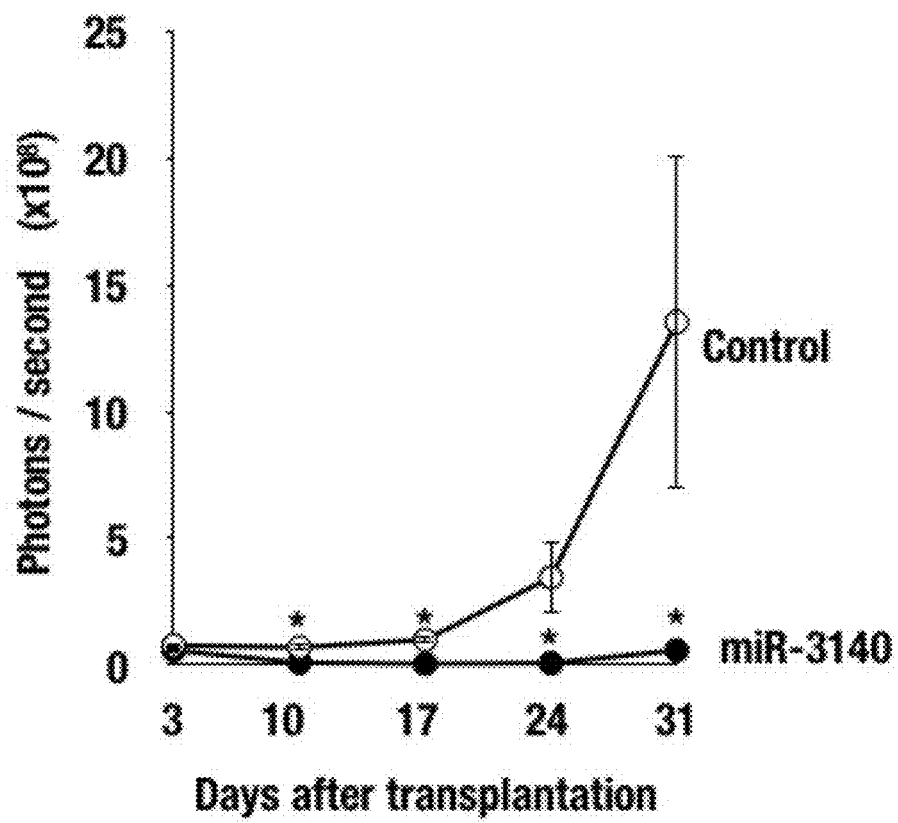
FIG. 27 shows the Imaging results when miR-3140-3p is administered three times.

By comparing the survival rates of mice, it was observed that the survival rates of mice had improved in the miR-3140-3p administration group (FIG. 22).

It was shown that similarly to the group with one administration, miR-3140-3p also significantly suppressed malignant pleural mesothelioma in the groups with two and three administrations of miR-3140-3p (FIGS. 23-28).

Figure 28:
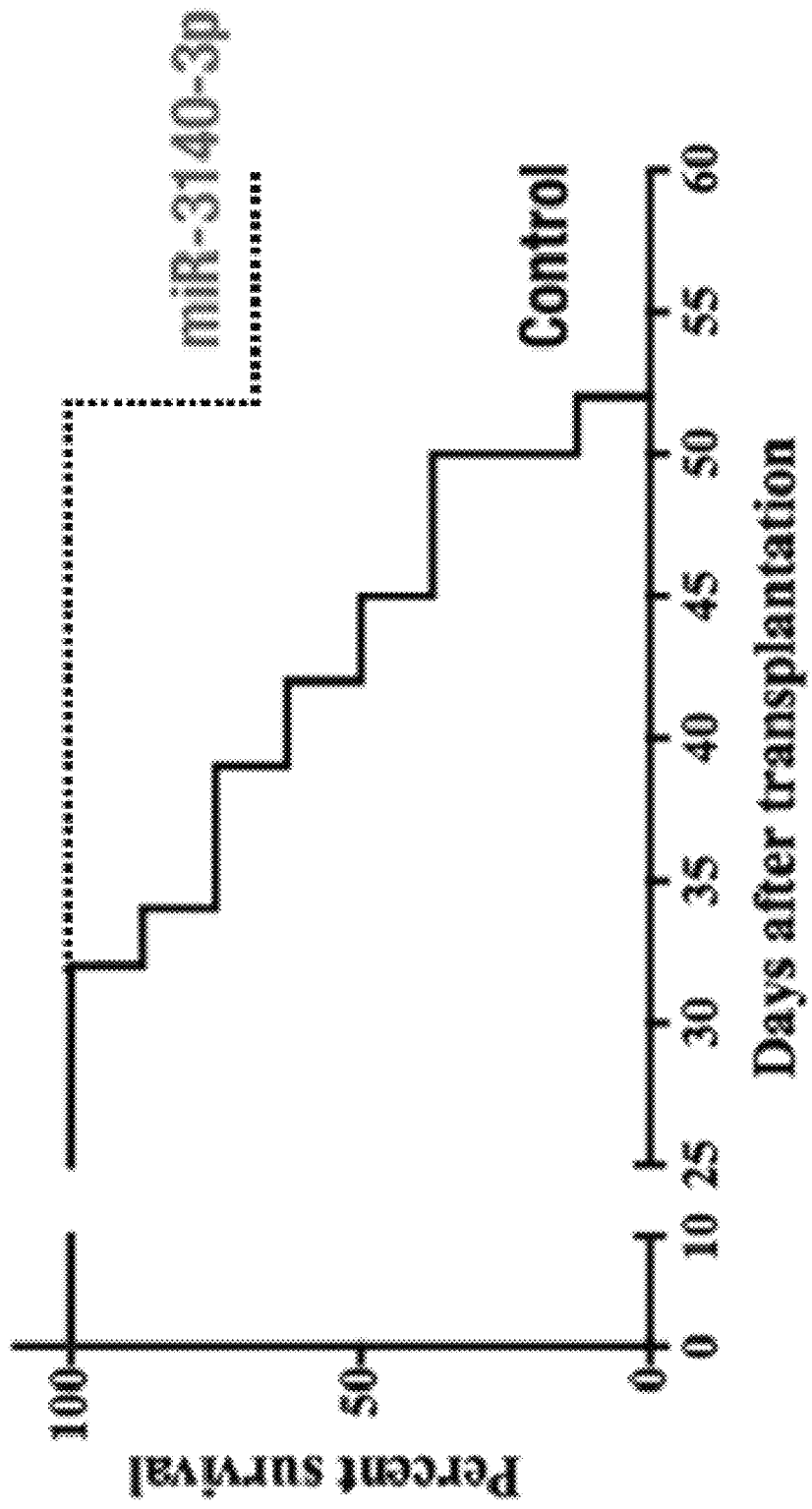
FIG. 28 shows the survival rates of mice when miR-3140-3p is administered three times.

The survival rates of mice were more improved in the group with three administrations of miR-3140-3p (FIG. 28).

Figure 29:
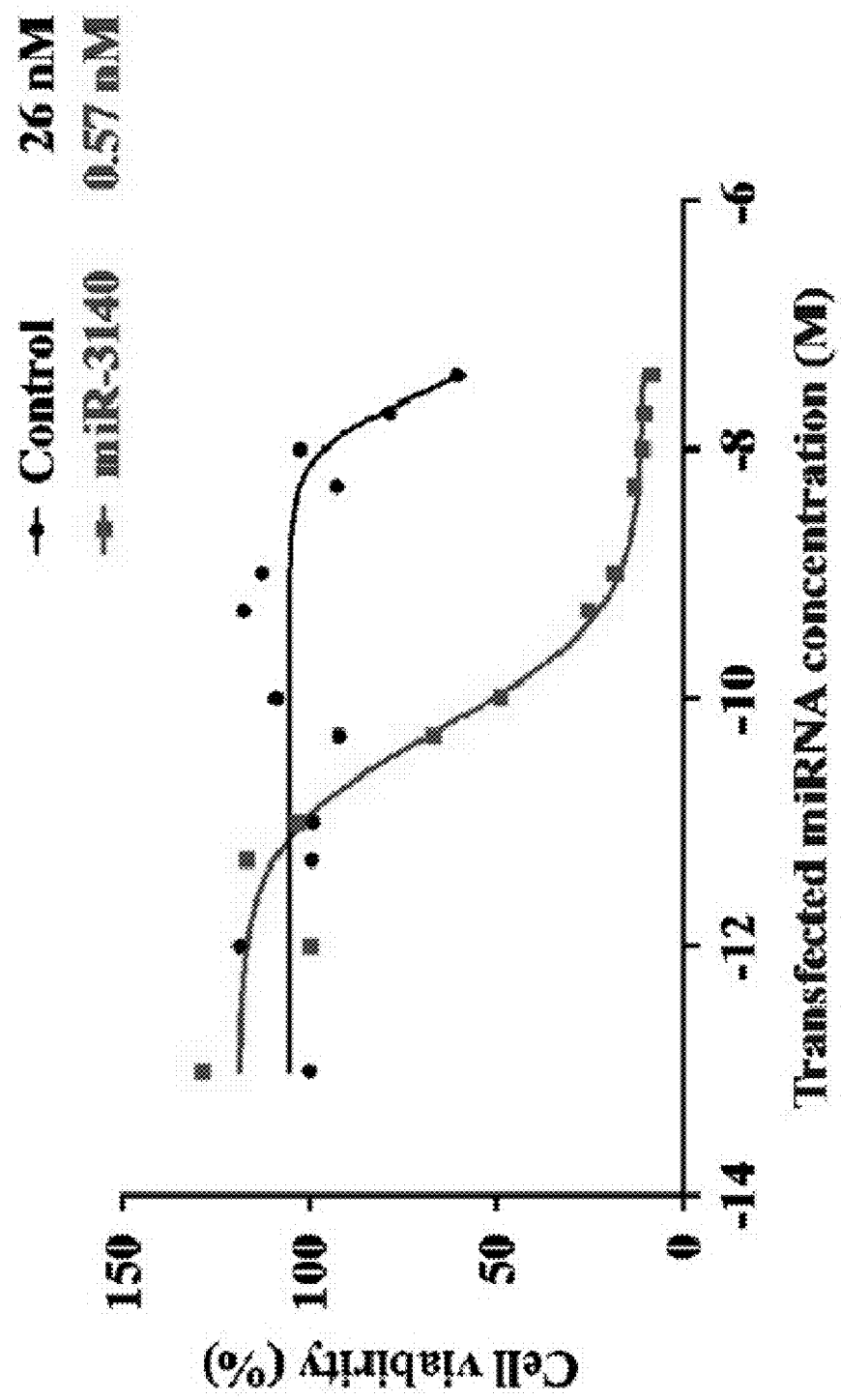
FIG. 29 shows the results of Experiment 8.
Figure 30:
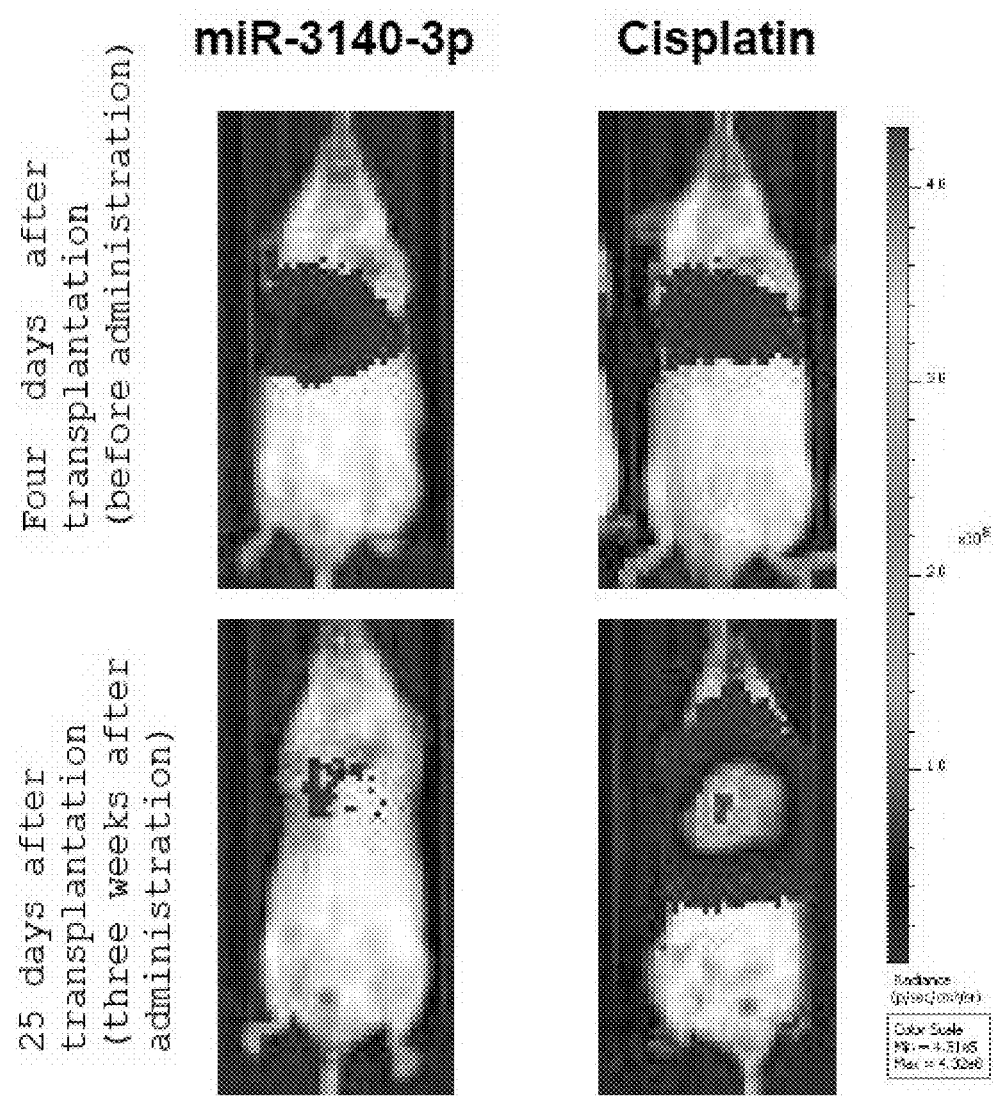
FIG. 30 shows the comparison of tumor suppression effect between miR-3140-3p and cisplatin.
Figure 31:
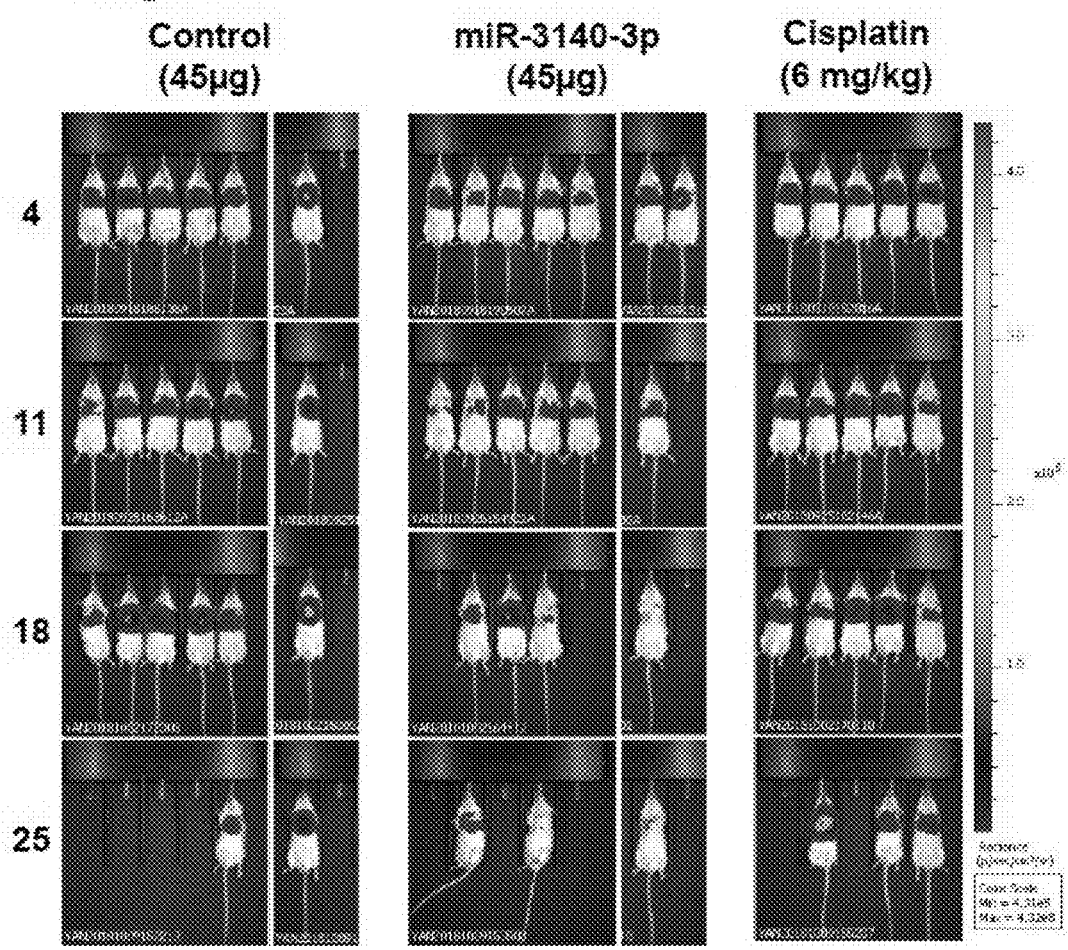
FIG. 31 shows the comparison of tumor suppression effect between miR-3140-3p and cisplatin.
Figure 32:
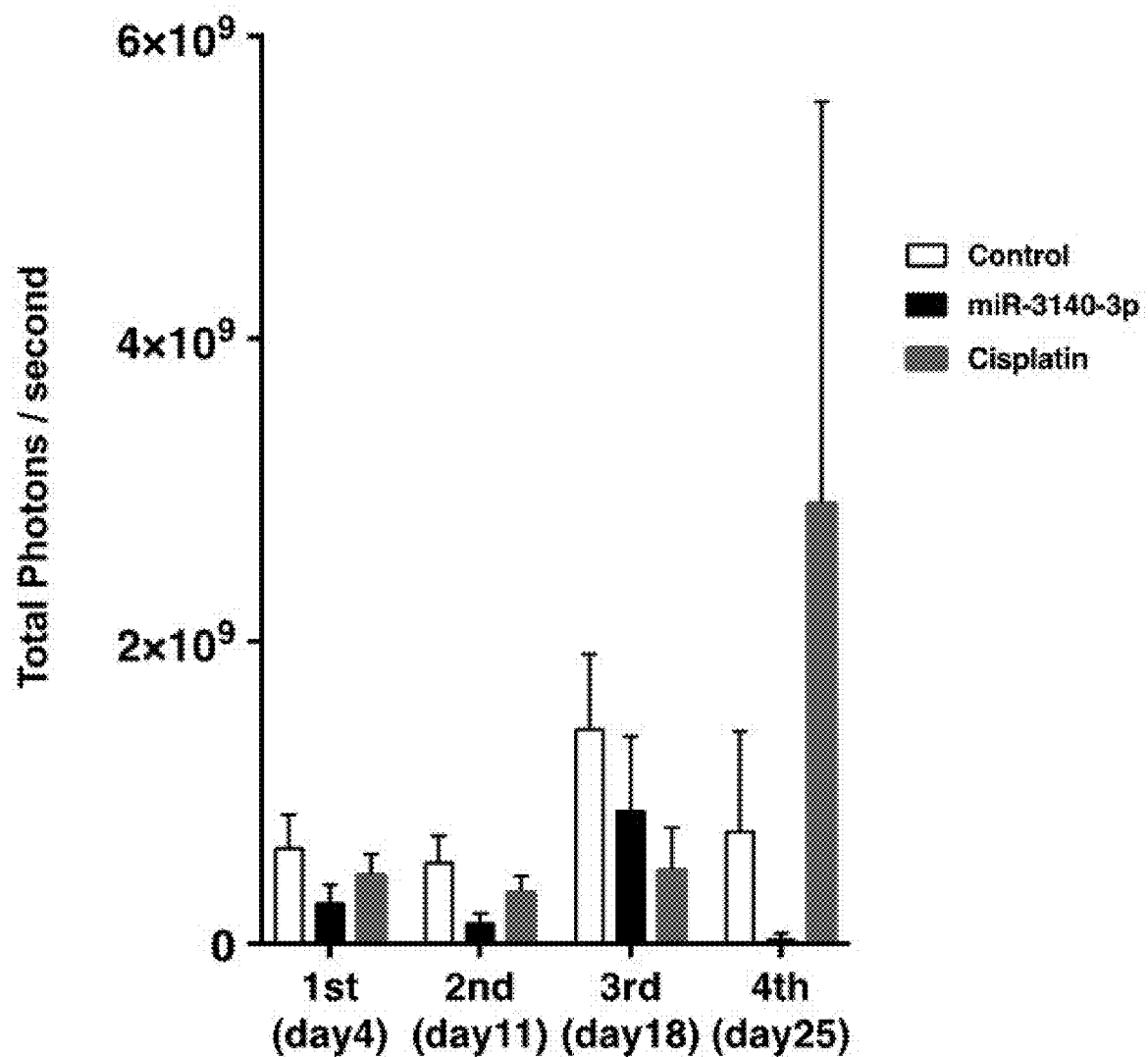
FIG. 32 shows the comparison of tumor suppression effect between miR-3140-3p and cisplatin.
Figure 33:
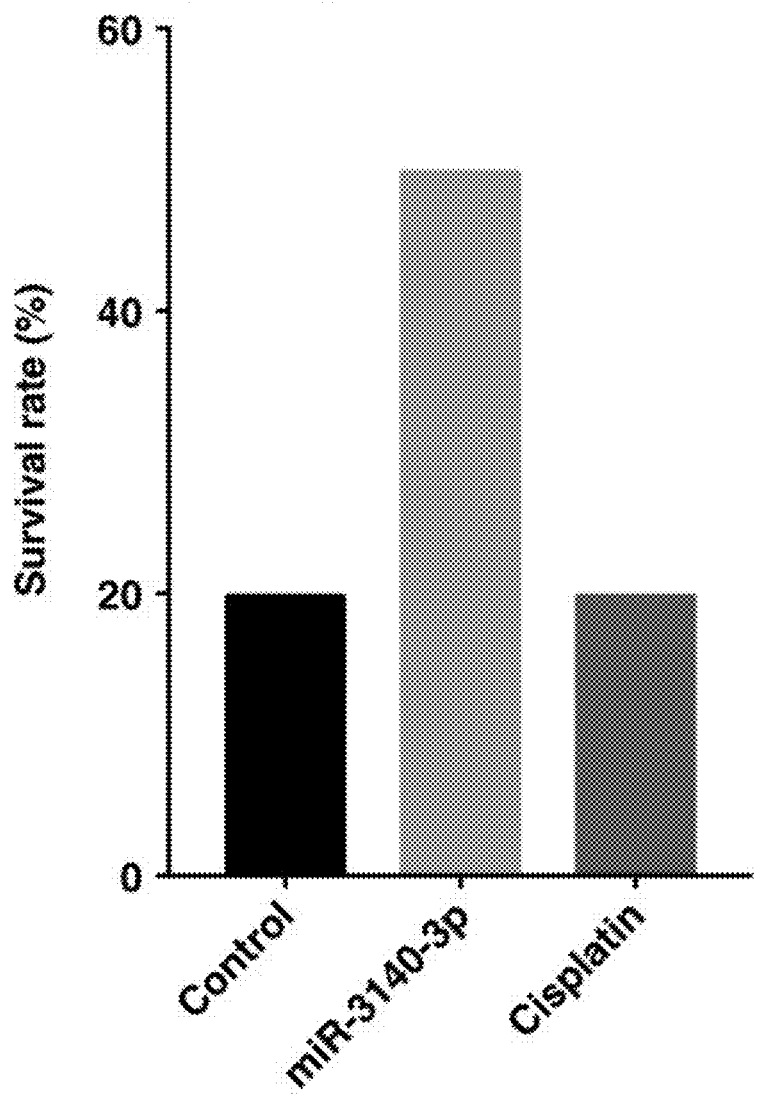
FIG. 33 shows the comparison of survival rates between miR-3140-3p administration group and cisplatin administration group.

Experiment 8. Calculation of $IC_{50}$ value (FIG. 29)

The $IC_{50}$ value of miR-3140-3p was calculated with malignant pleural mesothelioma cell EHMES-10.

The protocol therefor is shown below.

1: To 25 μL of serum free medium (SFM) was added 0.25 μL of RNAiMAX (Invitrogen).

2: miR-Control and miR-3140-3p were serially diluted so that the final concentrations will be 40 nM, 20 nM, 10 nM, 5 nM, 1 nM, 500 pM, 100 pM, 50 pM, 10 pM, 5 pM, and 1 pM, and mixed with SFM/RNAiMAX complex.

3: This was incubated at room temperature for 20 minutes.

4: 75 μL of each of cells at $6.7 \times 10^4$ cells/mL were added to each well.

5: This was incubated at 37° C. under 5% $CO_2$ condition.

6: Five days after transfection, the survival rates of cells were investigated with Cell Counting Kit 8 (DOJINDO). The protocol therefor is shown below.

(i) Cell Counting Kit was diluted 10-folds with a medium.
(ii) 200 μL of each of the diluted Cell Counting Kit was added to each well.
(iii) This was incubated at 37° C. under 5% $CO_2$ condition for 1 hour.
(iv) The values at 450 nm/600 nm were measured with a plate reader.

Note that the same control RNA as that used in Experiment 7 was employed as the control.

Results are shown in FIG. 29. As shown in FIG. 29, it was revealed that miR-3140-3p shows growth inhibition effect against malignant pleural mesothelioma cell strain EHMES-10 even at a very low concentration. Calculation of the $IC_{50}$ value gave a final concentration of 0.57 nM.

Experiment 9. Comparison of antitumor effect with chemotherapy agents (FIGS. 30-33)

In order to investigate the relative superiority of antitumor effect of miR-3140-3p, the tumor suppression effect of cisplatin which is the first-line drug of malignant pleural mesothelioma and the tumor suppression effect of miR-3140-3p were compared in vivo.

Six weeks-old male mice (C-B-17/Icr-scid/scid Jcl) were used as mice. Malignant pleural mesothelioma cell strain EHMES-10 which expresses the luciferase gene was used as the tumor cell.

The protocol is shown below.

1: Mice were intraperitoneally administered 0.1 mL per 10 g of body weight of a mixed anesthetic drug of medetomidine hydrochloride, midazolam, and butorphanol tartrate.

2: After anesthesia, mouse chest hair was shaved, and an incision was made in the epidermis with scissors.

3: In the mouse pleural cavity 100 μL of tumor cells ($3 \times 10^7$ cells/mL) was transplanted with a 27 G syringe for insulin.

4: Four days after transplantation, imaging of tumor cells was performed with IVIS Spectrum CT In vivo Imaging System.

5: After imaging, grouping was performed with successfully transplanted mice.

6: Mice were intraperitoneally administered 0.1 mL per 10 g of body weight of a mixed anesthetic drug of medetomidine hydrochloride, midazolam, and butorphanol tartrate to anesthetize the mice.

7: After anesthesia, 100 μL of the miRNA/A6K mixture was administered in the pleural cavity for the miRNA administration group, and cisplatin (6 mg/kg) was intraperitoneally administered to cisplatin administration group.

8: Imaging was performed every week from the first imaging, and tumor expansion was observed.

The mixed anesthetic drug was prepared as in Table 4 shown above. The miRNA/A6K mixture was prepared as in Tables 5 and 6 shown above. Cisplatin was prepared as in Table 7 below.

TABLE 11

Table 7 Preparation of cisplatin

| | /mL |
|---|---|
| Cisplatin (25 mg/50 mL) | 600 μL |
| DW | 400 μL |

Note that the same control RNA as that used in Experiment 7 was employed as the control.

Experimental results are shown in FIGS. 30-33. As shown in each figure, it was shown that miR-3140-3p may exert an antitumor effect that is equivalent or higher compared to cisplatin which is also the first-line drug of malignant pleural mesothelioma.

The invention claimed is:

1. A cancer therapy method,
the method comprising administering to a cancer patient a therapeutically effective amount of an anti-cancerous pharmaceutical composition comprising an RNA, which functions as a mature-miRNA, wherein the RNA comprises:
(i) a mature-miRNA consisting of the sequence of SEQ ID NO:2,
(ii) an RNA having a substitution, addition, and/or deletion of 1-5 bases to a mature-miRNA consisting of the sequence of SEQ ID NO. 2 and having a cancer therapeutic effect or
(iii) an RNA having 80% or more sequence identity to a mature-miRNA consisting of the sequence of SEQ ID NO. 2 and having a cancer therapeutic effect.

2. The method according to claim 1, wherein said cancer is a solid cancer.

3. The method according to claim 2, wherein said solid cancer is colon cancer, pancreatic cancer, tongue cancer, mesothelioma, uterine sarcoma, osteosarcoma, breast cancer, lung cancer, or head and neck cancer.

4. The method according to claim 1 wherein said RNA is chemically modified.

5. The method according to claim 4, wherein said chemical modification is one or more chemical modifications selected from the group consisting of LNA-tion, BNA-tion, ENA-ation, 2'-0Me modification, phosphorothioation, S-TuD-ation, morpholino modification, peptide addition, glycosylation, aptamer addition, hydrophobic molecule addition, polymer addition, and addition of unmodified DNA.

6. The method according to claim 1, wherein the anti-cancerous pharmaceutical composition further comprises a nucleic acid transfection agent.

7. The method according to claim 6, wherein said transfection agent is a lipid-based transfection agent, a polymer-based transfection agent, a magnetic particle-based transfection agent, an exosome for nucleic acid delivery, or a viral protein for nucleic acid delivery.

8. The method according to claim 6, wherein said transfection agent is a transfection agent comprising a peptide represented by amino acid sequences GGGGDD (G4D2) (SEQ ID NO:14), GGGGGGDD (G6D2) (SEQ ID NO:15), GGGGGGGGDD (G8D2) (SEQ ID NO:16), GGGGGGGGGGDD (G10D2) (SEQ ID NO:17), AAAAAAD (A6D) (SEQ ID NO:18), AAAAAADD (A6D2) (SEQ ID NO:19), AAAAAAK (A6K) (SEQ ID NO:20), AAAAAAKK (A6K2) (SEQ ID NO:21), VVVVVVD (V6D) (SEQ ID NO:22), VVVVVVDD (V6D2) (SEQ ID NO:23), VVVVVVK (V6K) (SEQ ID NO:24), VVVVVVKK (V6K2) (SEQ ID NO:25), LLLLLLD (L6D) (SEQ ID NO:26), LLLLLLDD (L6D2) (SEQ ID NO:27), LLLLLLK (L6K) (SEQ ID NO:28), or LLLLLLKK (L6K2) (SEQ ID NO:29).

9. The method according to claim 1, wherein the composition is for topical administration.

10. The method according to claim 1, wherein the method is used in combination with other anticancer agents.

11. The method according to claim 10, wherein said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

* * * * *

UNITED STATES PATENT AND TRADEMARK OFFICE
CERTIFICATE OF CORRECTION

PATENT NO. : 11,311,568 B2
APPLICATION NO. : 16/760817
DATED : April 26, 2022
INVENTOR(S) : Tahara et al.

It is certified that error appears in the above-identified patent and that said Letters Patent is hereby corrected as shown below:

In the Specification

Column 10, Line 63: Please insert a paragraph break between "1 hour." and "2. The"

In the Claims

Column 137, Line 27, Claim 5: Please correct "2′-0Me" to read --2′-OMe--

Signed and Sealed this
Fourth Day of October, 2022

Katherine Kelly Vidal
*Director of the United States Patent and Trademark Office*